(12) United States Patent
Sommer et al.

(10) Patent No.: US 7,449,561 B1
(45) Date of Patent: Nov. 11, 2008

(54) ALTERATIONS IN THE DYSTROPHIN GENE ASSOCIATED WITH SPORADIC DILATED CARDIOMYOPATHY

(75) Inventors: Steve S. Sommer, Duarte, CA (US); Jinong Feng, Arcadia, CA (US); Carolyn Buzin, Arcadia, CA (US); Jin Yan, Duarte, CA (US); Jeffrey Towbin, Houston, TX (US)

(73) Assignees: City of Hope, Duarte, CA (US); Baylor College of Medicine, Houston, TX (US)

( * ) Notice: Subject to any disclaimer, the term of this patent is extended or adjusted under 35 U.S.C. 154(b) by 400 days.

(21) Appl. No.: 10/371,222

(22) Filed: Feb. 24, 2003

Related U.S. Application Data

(60) Provisional application No. 60/359,324, filed on Feb. 26, 2002.

(51) Int. Cl.
*C07H 21/02* (2006.01)
*C07H 21/04* (2006.01)
*C12Q 1/68* (2006.01)

(52) U.S. Cl. .................. 536/23.1; 435/6; 536/24.33
(58) Field of Classification Search .............. None
See application file for complete search history.

(56) References Cited

U.S. PATENT DOCUMENTS 5,474,796 A * 12/1995 Brennan .................. 427/2.13

OTHER PUBLICATIONS

Arbustini et al., Journal of the American College of Cardiology, 2000, vol. 35, No. 7, pp. 1760-1768.*
Chaturvedi et al., Experimental and Molecular Medicine, 2001, vol. 33, No. 4, pp. 251-256.*
Genbank Accession No. M18533, May 25, 2000.*
Arbustini, E. et al., "Genetics of Idiopathic Dilated Cardiomyopathy," Herz 25(3):156-160, 2000.
Arbustini, E. et al., "Prevalence and Characteristics of Dystrophin Defects in Adult Male Patients With Dilated Cardiomyopathy," Journal of the American College of Cardiology, 35(7):1760-1768, 2000.
Bowles, N.E. et al., "The 'Final Common Pathway' Hypothesis and Inherited Cardiovascular Disease," Herz 25:168-175, 2000.
Gold, R. et al., "Brief Communication: Becker Muscular Dystrophy: Detection of Unusual Disease Courses by Combined Approach to Dystrophin Analysis," Muscle & Nerve 15:214-218, 1992.
Hunsaker, R.H. et al., "Cardiac Function in Duchenne's Muscular Dystrophy, Results of 10-Year Follow-up Study and Noninvasive Tests," The American Journal of Medicine 73:235-238, 1982.
Mendell, J.R. et al., "Diagnosis of Duchenne Dystrophy by Enhanced Detection of Small Muations," Neurology 57:645-650, 2001.
Milasin J. et al., "A Point Mutation in the 5' Splice Site of the Dystrophin Gene First Intron Responsible for X-Linked Dilated Cardiomyopathy," Human Molecular Genetics 5(1):73-79, 1996.
Muntoni, F. et al., "Brief Report: Deletion of the Dystrophin Muscle-Promoter Region Associated with X-Linked Dilated Cardiomyopathy," N. Eng. J. Med. 329(13):921-925, 1993.
Muntoni, F. et al., "A Mutation in the Dystrophin Gene Selectively Affecting Dystrophin Expression in the Heart," J. Clin. Invest. 96:693-699, 1995.
Muntoni, F. et al., "Dystrophin Gene Abnormalities in Two Patients with Idiopathic Dilated Cardiomyopathy," Heart 78:608-612, 1997.
Ortiz-Lopez, R. et al., "Evidence for a Dystrophin Missense Mutation as a Cause of X-Linked Dilated Cardiomyopathy," Circulation 95:2434-2440, 1997.
Perloff, J.K. et al., "The Cardiomyopathy of Progressive Muscular Dystrophy," Circulation 33:625-648, 1996.
Yoshida, K. et al., "Insertional Mutation by Transposable Element, L1, in the *DMD* Gene Results in X-Linked Dilated Cardiomyopathy," Human Molecular Genetics 7(7):1129-1132, 1998.

* cited by examiner

*Primary Examiner*—Juliet C. Switzer
*Assistant Examiner*—Katherine Salmon
(74) *Attorney, Agent, or Firm*—Rothwell, Figg, Ernst & Manbeck p.c.

(57) ABSTRACT

The present invention relates generally to the field of human genetics. Specifically, the present invention relates to methods and materials used to detect a human sporadic DCM predisposing gene, specifically the dystrophin gene, some mutant alleles of which cause susceptibility to sporadic DCM. More specifically, the invention relates to germline mutations in the dystrophin gene and their use in the diagnosis of predisposition to sporadic DCM. The invention also relates to the prophylaxis and/or therapy of sporadic DCM associated with a mutation in the dystrophin gene. The invention further relates to the screening of drugs for sporadic DCM therapy. Finally, the invention relates to the screening of the dystrophin gene for mutations/alterations, which are useful for diagnosing the predisposition to sporadic DCM.

2 Claims, 1 Drawing Sheet

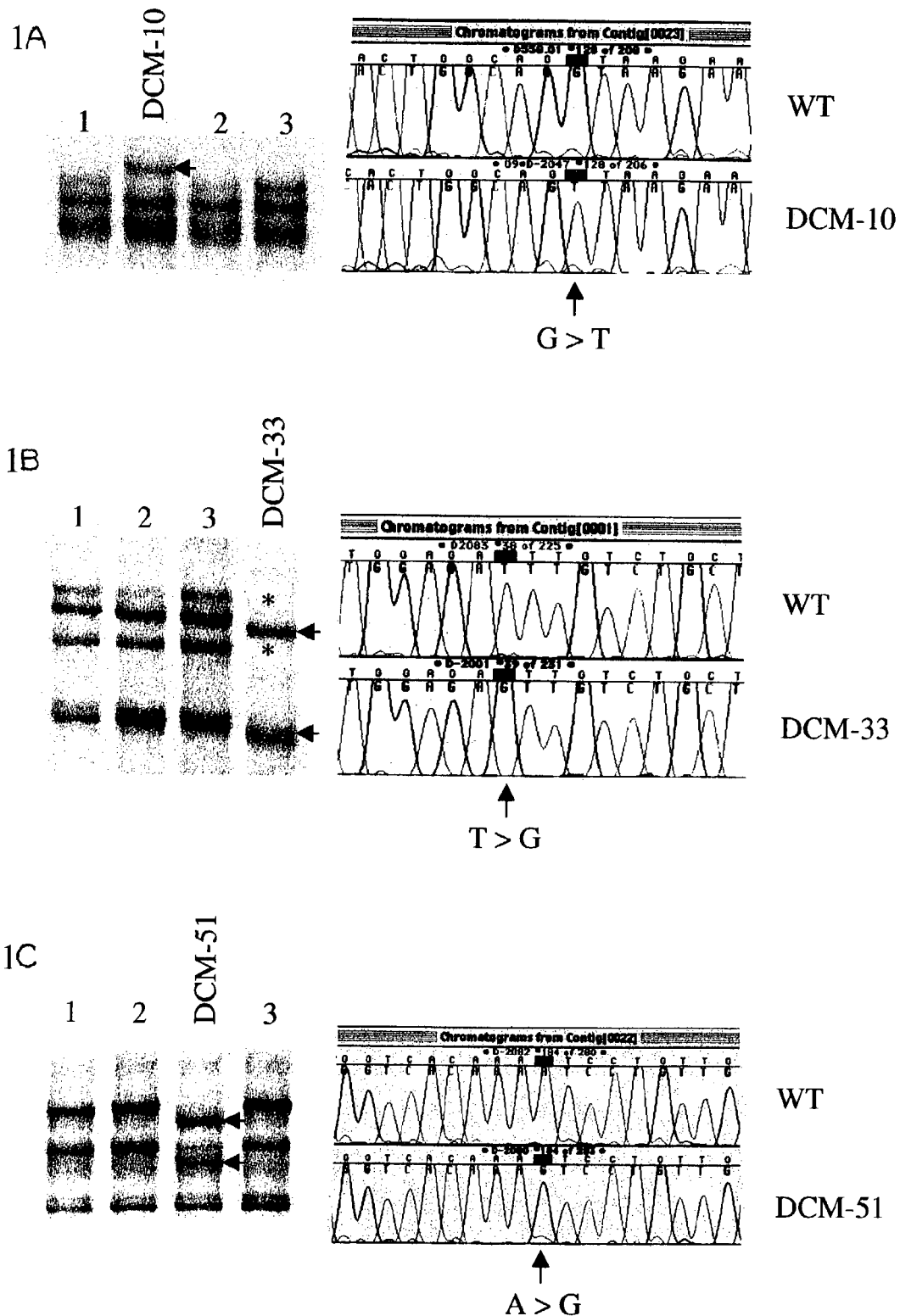

SEQUENCE LISTING

```
<160> NUMBER OF SEQ ID NOS: 87

<210> SEQ ID NO 1
<211> LENGTH: 13957
<212> TYPE: DNA
<213> ORGANISM: Homo sapiens
<220> FEATURE:
<221> NAME/KEY: CDS
<222> LOCATION: (209)..(11266)

<400> SEQUENCE: 1
gggattccct cactttcccc ctacaggact cagatctggg aggcaattac cttcggagaa         60
aaacgaatag gaaaaactga agtgttactt tttttaaagc tgctgaagtt tgttggtttc        120
tcattgtttt taagcctact ggagcaataa agtttgaaga acttttacca ggtttttttt        180
atcgctgcct tgatatacac ttttcaaa atg ctt tgg tgg gaa gaa gta gag          232
                                Met Leu Trp Trp Glu Glu Val Glu
                                1               5 gac tgt tat gaa aga gaa gat gtt caa aag aaa aca ttc aca aaa tgg         280
Asp Cys Tyr Glu Arg Glu Asp Val Gln Lys Lys Thr Phe Thr Lys Trp
        10                  15                  20 gta aat gca caa ttt tct aag ttt ggg aag cag cat att gag aac ctc         328
Val Asn Ala Gln Phe Ser Lys Phe Gly Lys Gln His Ile Glu Asn Leu
25                  30                  35                  40 ttc agt gac cta cag gat ggg agg cgc ctc cta gac ctc ctc gaa ggc         376
Phe Ser Asp Leu Gln Asp Gly Arg Arg Leu Leu Asp Leu Leu Glu Gly
                45                  50                  55 ctg aca ggg caa aaa ctg cca aaa gaa aaa gga tcc aca aga gtt cat         424
Leu Thr Gly Gln Lys Leu Pro Lys Glu Lys Gly Ser Thr Arg Val His
            60                  65                  70 gcc ctg aac aat gtc aac aag gca ctg cgg gtt ttg cag aac aat aat         472
Ala Leu Asn Asn Val Asn Lys Ala Leu Arg Val Leu Gln Asn Asn Asn
        75                  80                  85 gtt gat tta gtg aat att gga agt act gac atc gta gat gga aat cat         520
Val Asp Leu Val Asn Ile Gly Ser Thr Asp Ile Val Asp Gly Asn His
    90                  95                  100 aaa ctg act ctt ggt ttg att tgg aat ata atc ctc cac tgg cag gtc         568
Lys Leu Thr Leu Gly Leu Ile Trp Asn Ile Ile Leu His Trp Gln Val
105                 110                 115                 120
```

```
                                                              -continued
aaa aat gta atg aaa aat atc atg gct gga ttg caa caa acc aac agt         616
Lys Asn Val Met Lys Asn Ile Met Ala Gly Leu Gln Gln Thr Asn Ser
            125                 130                 135 gaa aag att ctc ctg agc tgg gtc cga caa tca act cgt aat tat cca         664
Glu Lys Ile Leu Leu Ser Trp Val Arg Gln Ser Thr Arg Asn Tyr Pro
                140                 145                 150 cag gtt aat gta atc aac ttc acc acc agc tgg tct gat ggc ctg gct         712
Gln Val Asn Val Ile Asn Phe Thr Thr Ser Trp Ser Asp Gly Leu Ala
            155                 160                 165 ttg aat gct ctc atc cat agt cat agg cca gac cta ttt gac tgg aat         760
Leu Asn Ala Leu Ile His Ser His Arg Pro Asp Leu Phe Asp Trp Asn
        170                 175                 180 agt gtg gtt tgc cag cag tca gcc aca caa cga ctg gaa cat gca ttc         808
Ser Val Val Cys Gln Gln Ser Ala Thr Gln Arg Leu Glu His Ala Phe
185                 190                 195                 200 aac atc gcc aga tat caa tta ggc ata gag aaa cta ctc gat cct gaa         856
Asn Ile Ala Arg Tyr Gln Leu Gly Ile Glu Lys Leu Leu Asp Pro Glu
                205                 210                 215 gat gtt gat acc acc tat cca gat aag aag tcc atc tta atg tac atc         904
Asp Val Asp Thr Thr Tyr Pro Asp Lys Lys Ser Ile Leu Met Tyr Ile
            220                 225                 230 aca tca ctc ttc caa gtt ttg cct caa caa gtg agc att gaa gcc atc         952
Thr Ser Leu Phe Gln Val Leu Pro Gln Gln Val Ser Ile Glu Ala Ile
        235                 240                 245 cag gaa gtg gaa atg ttg cca agg cca cct aaa gtg act aaa gaa gaa        1000
Gln Glu Val Glu Met Leu Pro Arg Pro Pro Lys Val Thr Lys Glu Glu
    250                 255                 260 cat ttt cag tta cat cat caa atg cac tat tct caa cag atc acg gtc        1048
His Phe Gln Leu His His Gln Met His Tyr Ser Gln Gln Ile Thr Val
265                 270                 275                 280 agt cta gca cag gga tat gag aga act tct tcc cct aag cct cga ttc        1096
Ser Leu Ala Gln Gly Tyr Glu Arg Thr Ser Ser Pro Lys Pro Arg Phe
                285                 290                 295 aag agc tat gcc tac aca cag gct gct tat gtc acc acc tct gac cct        1144
Lys Ser Tyr Ala Tyr Thr Gln Ala Ala Tyr Val Thr Thr Ser Asp Pro
            300                 305                 310 aca cgg agc cca ttt cct tca cag cat ttg gaa gct cct gaa gac aag        1192
Thr Arg Ser Pro Phe Pro Ser Gln His Leu Glu Ala Pro Glu Asp Lys
        315                 320                 325 tca ttt ggc agt tca ttg atg gag agt gaa gta aac ctg gac cgt tat        1240
Ser Phe Gly Ser Ser Leu Met Glu Ser Glu Val Asn Leu Asp Arg Tyr
    330                 335                 340 caa aca gct tta gaa gaa gta tta tcg tgg ctt ctt tct gct gag gac        1288
Gln Thr Ala Leu Glu Glu Val Leu Ser Trp Leu Leu Ser Ala Glu Asp
345                 350                 355                 360 aca ttg caa gca caa gga gag att tct aat gat gtg gaa gtg gtg aaa        1336
Thr Leu Gln Ala Gln Gly Glu Ile Ser Asn Asp Val Glu Val Val Lys
                365                 370                 375 gac cag ttt cat act cat gag ggg tac atg atg gat ttg aca gcc cat        1384
Asp Gln Phe His Thr His Glu Gly Tyr Met Met Asp Leu Thr Ala His
            380                 385                 390 cag ggc cgg gtt ggt aat att cta caa ttg gga agt aag ctg att gga        1432
Gln Gly Arg Val Gly Asn Ile Leu Gln Leu Gly Ser Lys Leu Ile Gly
        395                 400                 405 aca gga aaa tta tca gaa gat gaa gaa act gaa gta caa gag cag atg        1480
Thr Gly Lys Leu Ser Glu Asp Glu Glu Thr Glu Val Gln Glu Gln Met
    410                 415                 420 aat ctc cta aat tca aga tgg gaa tgc ctc agg gta gct agc atg gaa        1528
Asn Leu Leu Asn Ser Arg Trp Glu Cys Leu Arg Val Ala Ser Met Glu
425                 430                 435                 440
```

```
aaa caa agc aat tta cat aga gtt tta atg gat ctc cag aat cag aaa    1576
Lys Gln Ser Asn Leu His Arg Val Leu Met Asp Leu Gln Asn Gln Lys
                445                 450                 455 ctg aaa gag ttg aat gac tgg cta aca aaa aca gaa gaa aga aca agg    1624
Leu Lys Glu Leu Asn Asp Trp Leu Thr Lys Thr Glu Glu Arg Thr Arg
        460                 465                 470 aaa atg gag gaa gag cct ctt gga cct gat ctt gaa gac cta aaa cgc    1672
Lys Met Glu Glu Glu Pro Leu Gly Pro Asp Leu Glu Asp Leu Lys Arg
            475                 480                 485 caa gta caa caa cat aag gtg ctt caa gaa gat cta gaa caa gaa caa    1720
Gln Val Gln Gln His Lys Val Leu Gln Glu Asp Leu Glu Gln Glu Gln
        490                 495                 500 gtc agg gtc aat tct ctc act cac atg gtg gtg gta gtt gat gaa tct    1768
Val Arg Val Asn Ser Leu Thr His Met Val Val Val Asp Glu Ser
505                 510                 515                 520 agt gga gat cac gca act gct gct ttg gaa gaa caa ctt aag gta ttg    1816
Ser Gly Asp His Ala Thr Ala Ala Leu Glu Glu Gln Leu Lys Val Leu
                525                 530                 535 gga gat cga tgg gca aac atc tgt aga tgg aca gaa gac cgc tgg gtt    1864
Gly Asp Arg Trp Ala Asn Ile Cys Arg Trp Thr Glu Asp Arg Trp Val
        540                 545                 550 ctt tta caa gac atc ctt ctc aaa tgg caa cgt ctt act gaa gaa cag    1912
Leu Leu Gln Asp Ile Leu Leu Lys Trp Gln Arg Leu Thr Glu Glu Gln
            555                 560                 565 tgc ctt ttt agt gca tgg ctt tca gaa aaa gaa gat gca gtg aac aag    1960
Cys Leu Phe Ser Ala Trp Leu Ser Glu Lys Glu Asp Ala Val Asn Lys
        570                 575                 580 att cac aca act ggc ttt aaa gat caa aat gaa atg tta tca agt ctt    2008
Ile His Thr Thr Gly Phe Lys Asp Gln Asn Glu Met Leu Ser Ser Leu
585                 590                 595                 600 caa aaa ctg gcc gtt tta aaa gcg gat cta gaa aag aaa aag caa tcc    2056
Gln Lys Leu Ala Val Leu Lys Ala Asp Leu Glu Lys Lys Lys Gln Ser
                605                 610                 615 atg ggc aaa ctg tat tca ctc aaa caa gat ctt ctt tca aca ctg aag    2104
Met Gly Lys Leu Tyr Ser Leu Lys Gln Asp Leu Leu Ser Thr Leu Lys
        620                 625                 630 aat aag tca gtg acc cag aag acg gaa gca tgg ctg gat aac ttt gcc    2152
Asn Lys Ser Val Thr Gln Lys Thr Glu Ala Trp Leu Asp Asn Phe Ala
            635                 640                 645 cgg tgt tgg gat aat tta gtc caa aaa ctt gaa aag agt aca gca cag    2200
Arg Cys Trp Asp Asn Leu Val Gln Lys Leu Glu Lys Ser Thr Ala Gln
        650                 655                 660 att tca cag gct gtc acc acc act cag cca tca cta aca cag aca act    2248
Ile Ser Gln Ala Val Thr Thr Thr Gln Pro Ser Leu Thr Gln Thr Thr
665                 670                 675                 680 gta atg gaa aca gta act acg gtg acc aca agg gaa cag atc ctg gta    2296
Val Met Glu Thr Val Thr Thr Val Thr Thr Arg Glu Gln Ile Leu Val
                685                 690                 695 aag cat gct caa gag gaa ctt cca cca cca cct ccc caa aag aag agg    2344
Lys His Ala Gln Glu Glu Leu Pro Pro Pro Pro Pro Gln Lys Lys Arg
        700                 705                 710 cag att act gtg gat tct gaa att agg aaa agg ttg gat gtt gat ata    2392
Gln Ile Thr Val Asp Ser Glu Ile Arg Lys Arg Leu Asp Val Asp Ile
            715                 720                 725 act gaa ctt cac agc tgg att act cgc tca gaa gct gtg ttg cag agt    2440
Thr Glu Leu His Ser Trp Ile Thr Arg Ser Glu Ala Val Leu Gln Ser
        730                 735                 740 cct gaa ttt gca atc ttt cgg aag gaa ggc aac ttc tca gac tta aaa    2488
Pro Glu Phe Ala Ile Phe Arg Lys Glu Gly Asn Phe Ser Asp Leu Lys
```

-continued

```
        745                 750                 755                 760
gaa aaa gtc aat gcc ata gag cga gaa aaa gct gag aag ttc aga aaa       2536
Glu Lys Val Asn Ala Ile Glu Arg Glu Lys Ala Glu Lys Phe Arg Lys
                765                 770                 775 ctg caa gat gcc agc aga tca gct cag gcc ctg gtg gaa cag atg gtg       2584
Leu Gln Asp Ala Ser Arg Ser Ala Gln Ala Leu Val Glu Gln Met Val
                780                 785                 790 aat gag ggt gtt aat gca gat agc atc aaa caa gcc tca gaa caa ctg       2632
Asn Glu Gly Val Asn Ala Asp Ser Ile Lys Gln Ala Ser Glu Gln Leu
            795                 800                 805 aac agc cgg tgg atc gaa ttc tgc cag ttg cta agt gag aga ctt aac       2680
Asn Ser Arg Trp Ile Glu Phe Cys Gln Leu Leu Ser Glu Arg Leu Asn
        810                 815                 820 tgg ctg gag tat cag aac aac atc atc gct ttc tat aat cag cta caa       2728
Trp Leu Glu Tyr Gln Asn Asn Ile Ile Ala Phe Tyr Asn Gln Leu Gln
825                 830                 835                 840 caa ttg gag cag atg aca act act gct gaa aac tgg ttg aaa atc caa       2776
Gln Leu Glu Gln Met Thr Thr Thr Ala Glu Asn Trp Leu Lys Ile Gln
                845                 850                 855 ccc acc acc cca tca gag cca aca gca att aaa agt cag tta aaa att       2824
Pro Thr Thr Pro Ser Glu Pro Thr Ala Ile Lys Ser Gln Leu Lys Ile
                860                 865                 870 tgt aag gat gaa gtc aac cgg cta tca ggt ctt caa cct caa att gaa       2872
Cys Lys Asp Glu Val Asn Arg Leu Ser Gly Leu Gln Pro Gln Ile Glu
            875                 880                 885 cga tta aaa att caa agc ata gcc ctg aaa gag aaa gga caa gga ccc       2920
Arg Leu Lys Ile Gln Ser Ile Ala Leu Lys Glu Lys Gly Gln Gly Pro
        890                 895                 900 atg ttc ctg gat gca gac ttt gtg gcc ttt aca aat cat ttt aag caa       2968
Met Phe Leu Asp Ala Asp Phe Val Ala Phe Thr Asn His Phe Lys Gln
905                 910                 915                 920 gtc ttt tct gat gtg cag gcc aga gag aaa gag cta cag aca att ttt       3016
Val Phe Ser Asp Val Gln Ala Arg Glu Lys Glu Leu Gln Thr Ile Phe
                925                 930                 935 gac act ttg cca cca atg cgc tat cag gag acc atg agt gcc atc agg       3064
Asp Thr Leu Pro Pro Met Arg Tyr Gln Glu Thr Met Ser Ala Ile Arg
                940                 945                 950 aca tgg gtc cag cag tca gaa acc aaa ctc tcc ata cct caa ctt agt       3112
Thr Trp Val Gln Gln Ser Glu Thr Lys Leu Ser Ile Pro Gln Leu Ser
            955                 960                 965 gtc acc gac tat gaa atc atg gag cag aga ctc ggg gaa ttg cag gct       3160
Val Thr Asp Tyr Glu Ile Met Glu Gln Arg Leu Gly Glu Leu Gln Ala
        970                 975                 980 tta caa agt tct ctg caa gag caa caa agt ggc cta tac tat ctc agc       3208
Leu Gln Ser Ser Leu Gln Glu Gln Gln Ser Gly Leu Tyr Tyr Leu Ser
985                 990                 995                 1000 acc act gtg aaa gag  atg tcg aag aaa gcg  ccc tct gaa att agc        3253
Thr Thr Val Lys Glu  Met Ser Lys Lys Ala  Pro Ser Glu Ile Ser
                1005                1010                1015 cgg aaa tat caa tca  gaa ttt gaa gaa att  gag gga cgc tgg aag        3298
Arg Lys Tyr Gln Ser  Glu Phe Glu Glu Ile  Glu Gly Arg Trp Lys
                1020                1025                1030 aag ctc tcc tcc cag  ctg gtt gag cat tgt  caa aag cta gag gag        3343
Lys Leu Ser Ser Gln  Leu Val Glu His Cys  Gln Lys Leu Glu Glu
                1035                1040                1045 caa atg aat aaa ctc  cga aaa att cag aat  cac ata caa acc ctg        3388
Gln Met Asn Lys Leu  Arg Lys Ile Gln Asn  His Ile Gln Thr Leu
                1050                1055                1060 aag aaa tgg atg gct  gaa gtt gat gtt ttt  ctg aag gag gaa tgg        3433
```

```
Lys Lys Trp Met Ala Glu Val Asp Val Phe Leu Lys Glu Glu Trp
            1065            1070            1075 cct gcc ctt ggg gat tca gaa att cta aaa aag cag ctg aaa cag         3478
Pro Ala Leu Gly Asp Ser Glu Ile Leu Lys Lys Gln Leu Lys Gln
            1080            1085            1090 tgc aga ctt tta gtc agt gat att cag aca att cag ccc agt cta         3523
Cys Arg Leu Leu Val Ser Asp Ile Gln Thr Ile Gln Pro Ser Leu
            1095            1100            1105 aac agt gtc aat gaa ggt ggg cag aag ata aag aat gaa gca gag         3568
Asn Ser Val Asn Glu Gly Gly Gln Lys Ile Lys Asn Glu Ala Glu
            1110            1115            1120 cca gag ttt gct tcg aga ctt gag aca gaa ctc aaa gaa ctt aac         3613
Pro Glu Phe Ala Ser Arg Leu Glu Thr Glu Leu Lys Glu Leu Asn
            1125            1130            1135 act cag tgg gat cac atg tgc caa cag gtc tat gcc aga aag gag         3658
Thr Gln Trp Asp His Met Cys Gln Gln Val Tyr Ala Arg Lys Glu
            1140            1145            1150 gcc ttg aag gga ggt ttg gag aaa act gta agc ctc cag aaa gat         3703
Ala Leu Lys Gly Gly Leu Glu Lys Thr Val Ser Leu Gln Lys Asp
            1155            1160            1165 cta tca gag atg cac gaa tgg atg aca caa gct gaa gaa gag tat         3748
Leu Ser Glu Met His Glu Trp Met Thr Gln Ala Glu Glu Glu Tyr
            1170            1175            1180 ctt gag aga gat ttt gaa tat aaa act cca gat gaa tta cag aaa         3793
Leu Glu Arg Asp Phe Glu Tyr Lys Thr Pro Asp Glu Leu Gln Lys
            1185            1190            1195 gca gtt gaa gag atg aag aga gct aaa gaa gag gcc caa caa aaa         3838
Ala Val Glu Glu Met Lys Arg Ala Lys Glu Glu Ala Gln Gln Lys
            1200            1205            1210 gaa gcg aaa gtg aaa ctc ctt act gag tct gta aat agt gtc ata         3883
Glu Ala Lys Val Lys Leu Leu Thr Glu Ser Val Asn Ser Val Ile
            1215            1220            1225 gct caa gct cca cct gta gca caa gag gcc tta aaa aag gaa ctt         3928
Ala Gln Ala Pro Pro Val Ala Gln Glu Ala Leu Lys Lys Glu Leu
            1230            1235            1240 gaa act cta acc acc aac tac cag tgg ctc tgc act agg ctg aat         3973
Glu Thr Leu Thr Thr Asn Tyr Gln Trp Leu Cys Thr Arg Leu Asn
            1245            1250            1255 ggg aaa tgc aag act ttg gaa gaa gtt tgg gca tgt tgg cat gag         4018
Gly Lys Cys Lys Thr Leu Glu Glu Val Trp Ala Cys Trp His Glu
            1260            1265            1270 tta ttg tca tac ttg gag aaa gca aac aag tgg cta aat gaa gta         4063
Leu Leu Ser Tyr Leu Glu Lys Ala Asn Lys Trp Leu Asn Glu Val
            1275            1280            1285 gaa ttt aaa ctt aaa acc act gaa aac att cct ggc gga gct gag         4108
Glu Phe Lys Leu Lys Thr Thr Glu Asn Ile Pro Gly Gly Ala Glu
            1290            1295            1300 gaa atc tct gag gtg cta gat tca ctt gaa aat ttg atg cga cat         4153
Glu Ile Ser Glu Val Leu Asp Ser Leu Glu Asn Leu Met Arg His
            1305            1310            1315 tca gag gat aac cca aat cag att cgc ata ttg gca cag acc cta         4198
Ser Glu Asp Asn Pro Asn Gln Ile Arg Ile Leu Ala Gln Thr Leu
            1320            1325            1330 aca gat ggc gga gtc atg gat gag cta atc aat gag gaa ctt gag         4243
Thr Asp Gly Gly Val Met Asp Glu Leu Ile Asn Glu Glu Leu Glu
            1335            1340            1345 aca ttt aat tct cgt tgg agg gaa cta cat gaa gag gct gta agg         4288
Thr Phe Asn Ser Arg Trp Arg Glu Leu His Glu Glu Ala Val Arg
            1350            1355            1360
```

```
agg caa aag ttg ctt  gaa cag agc atc cag  tct gcc cag gag act       4333
Arg Gln Lys Leu Leu  Glu Gln Ser Ile Gln  Ser Ala Gln Glu Thr
             1365                 1370                 1375 gaa aaa tcc tta cac  tta atc cag gag tcc  ctc aca ttc att gac       4378
Glu Lys Ser Leu His  Leu Ile Gln Glu Ser  Leu Thr Phe Ile Asp
             1380                 1385                 1390 aag cag ttg gca gct  tat att gca gac aag  gtg gac gca gct caa       4423
Lys Gln Leu Ala Ala  Tyr Ile Ala Asp Lys  Val Asp Ala Ala Gln
             1395                 1400                 1405 atg cct cag gaa gcc  cag aaa atc caa tct  gat ttg aca agt cat       4468
Met Pro Gln Glu Ala  Gln Lys Ile Gln Ser  Asp Leu Thr Ser His
             1410                 1415                 1420 gag atc agt tta gaa  gaa atg aag aaa cat  aat cag ggg aag gag       4513
Glu Ile Ser Leu Glu  Glu Met Lys Lys His  Asn Gln Gly Lys Glu
             1425                 1430                 1435 gct gcc caa aga gtc  ctg tct cag att gat  gtt gca cag aaa aaa       4558
Ala Ala Gln Arg Val  Leu Ser Gln Ile Asp  Val Ala Gln Lys Lys
             1440                 1445                 1450 tta caa gat gtc tcc  atg aag ttt cga tta  ttc cag aaa cca gcc       4603
Leu Gln Asp Val Ser  Met Lys Phe Arg Leu  Phe Gln Lys Pro Ala
             1455                 1460                 1465 aat ttt gag ctg cgt  cta caa gaa agt aag  atg att tta gat gaa       4648
Asn Phe Glu Leu Arg  Leu Gln Glu Ser Lys  Met Ile Leu Asp Glu
             1470                 1475                 1480 gtg aag atg cac ttg  cct gca ttg gaa aca  aag agt gtg gaa cag       4693
Val Lys Met His Leu  Pro Ala Leu Glu Thr  Lys Ser Val Glu Gln
             1485                 1490                 1495 gaa gta gta cag tca  cag cta aat cat tgt  gtg aac ttg tat aaa       4738
Glu Val Val Gln Ser  Gln Leu Asn His Cys  Val Asn Leu Tyr Lys
             1500                 1505                 1510 agt ctg agt gaa gtg  aag tct gaa gtg gaa  atg gtg ata aag act       4783
Ser Leu Ser Glu Val  Lys Ser Glu Val Glu  Met Val Ile Lys Thr
             1515                 1520                 1525 gga cgt cag att gta  cag aaa aag cag acg  gaa aat ccc aaa gaa       4828
Gly Arg Gln Ile Val  Gln Lys Lys Gln Thr  Glu Asn Pro Lys Glu
             1530                 1535                 1540 ctt gat gaa aga gta  aca gct ttg aaa ttg  cat tat aat gag ctg       4873
Leu Asp Glu Arg Val  Thr Ala Leu Lys Leu  His Tyr Asn Glu Leu
             1545                 1550                 1555 gga gca aag gta aca  gaa aga aag caa cag  ttg gag aaa tgc ttg       4918
Gly Ala Lys Val Thr  Glu Arg Lys Gln Gln  Leu Glu Lys Cys Leu
             1560                 1565                 1570 aaa ttg tcc cgt aag  atg cga aag gaa atg  aat gtc ttg aca gaa       4963
Lys Leu Ser Arg Lys  Met Arg Lys Glu Met  Asn Val Leu Thr Glu
             1575                 1580                 1585 tgg ctg gca gct aca  gat atg gaa ttg aca  aag aga tca gca gtt       5008
Trp Leu Ala Ala Thr  Asp Met Glu Leu Thr  Lys Arg Ser Ala Val
             1590                 1595                 1600 gaa gga atg cct agt  aat ttg gat tct gaa  gtt gcc tgg gga aag       5053
Glu Gly Met Pro Ser  Asn Leu Asp Ser Glu  Val Ala Trp Gly Lys
             1605                 1610                 1615 gct act caa aaa gag  att gag aaa cag aag  gtg cac ctg aag agt       5098
Ala Thr Gln Lys Glu  Ile Glu Lys Gln Lys  Val His Leu Lys Ser
             1620                 1625                 1630 atc aca gag gta gga  gag gcc ttg aaa aca  gtt ttg ggc aag aag       5143
Ile Thr Glu Val Gly  Glu Ala Leu Lys Thr  Val Leu Gly Lys Lys
             1635                 1640                 1645 gag acg ttg gtg gaa  gat aaa ctc agt ctt  ctg aat agt aac tgg       5188
Glu Thr Leu Val Glu  Asp Lys Leu Ser Leu  Leu Asn Ser Asn Trp
             1650                 1655                 1660
```

| | | | | | | | | | | | |
|---|---|---|---|---|---|---|---|---|---|---|---|
| ata | gct | gtc | acc | tcc | cga | gca | gaa | gag | tgg | tta | aat ctt ttg ttg | 5233 |
| Ile | Ala | Val | Thr | Ser | Arg | Ala | Glu | Glu | Trp | Leu | Asn Leu Leu Leu |
| | | | 1665 | | | | 1670 | | | | 1675 |

| gaa tac cag aaa cac atg gaa act ttt gac cag aat gtg gac cac | 5278 |
| Glu Tyr Gln Lys His Met Glu Thr Phe Asp Gln Asn Val Asp His |
| 1680 1685 1690 |

| atc aca aag tgg atc att cag gct gac aca ctt ttg gat gaa tca | 5323 |
| Ile Thr Lys Trp Ile Ile Gln Ala Asp Thr Leu Leu Asp Glu Ser |
| 1695 1700 1705 |

| gag aaa aag aaa ccc cag caa aaa gaa gac gtg ctt aag cgt tta | 5368 |
| Glu Lys Lys Lys Pro Gln Gln Lys Glu Asp Val Leu Lys Arg Leu |
| 1710 1715 1720 |

| aag gca gaa ctg aat gac ata cgc cca aag gtg gac tct aca cgt | 5413 |
| Lys Ala Glu Leu Asn Asp Ile Arg Pro Lys Val Asp Ser Thr Arg |
| 1725 1730 1735 |

| gac caa gca gca aac ttg atg gca aac cgc ggt gac cac tgc agg | 5458 |
| Asp Gln Ala Ala Asn Leu Met Ala Asn Arg Gly Asp His Cys Arg |
| 1740 1745 1750 |

| aaa tta gta gag ccc caa atc tca gag ctc aac cat cga ttt gca | 5503 |
| Lys Leu Val Glu Pro Gln Ile Ser Glu Leu Asn His Arg Phe Ala |
| 1755 1760 1765 |

| gcc att tca cac aga att aag act gga aag gcc tcc att cct ttg | 5548 |
| Ala Ile Ser His Arg Ile Lys Thr Gly Lys Ala Ser Ile Pro Leu |
| 1770 1775 1780 |

| aag gaa ttg gag cag ttt aac tca gat ata caa aaa ttg ctt gaa | 5593 |
| Lys Glu Leu Glu Gln Phe Asn Ser Asp Ile Gln Lys Leu Leu Glu |
| 1785 1790 1795 |

| cca ctg gag gct gaa att cag cag ggg gtg aat ctg aaa gag gaa | 5638 |
| Pro Leu Glu Ala Glu Ile Gln Gln Gly Val Asn Leu Lys Glu Glu |
| 1800 1805 1810 |

| gac ttc aat aaa gat atg aat gaa gac aat gag ggt act gta aaa | 5683 |
| Asp Phe Asn Lys Asp Met Asn Glu Asp Asn Glu Gly Thr Val Lys |
| 1815 1820 1825 |

| gaa ttg ttg caa aga gga gac aac tta caa caa aga atc aca gat | 5728 |
| Glu Leu Leu Gln Arg Gly Asp Asn Leu Gln Gln Arg Ile Thr Asp |
| 1830 1835 1840 |

| gag aga aag aga gag gaa ata aag ata aaa cag cag ctg tta cag | 5773 |
| Glu Arg Lys Arg Glu Glu Ile Lys Ile Lys Gln Gln Leu Leu Gln |
| 1845 1850 1855 |

| aca aaa cat aat gct ctc aag gat ttg agg tct caa aga aga aaa | 5818 |
| Thr Lys His Asn Ala Leu Lys Asp Leu Arg Ser Gln Arg Arg Lys |
| 1860 1865 1870 |

| aag gct cta gaa att tct cat cag tgg tat cag tac aag agg cag | 5863 |
| Lys Ala Leu Glu Ile Ser His Gln Trp Tyr Gln Tyr Lys Arg Gln |
| 1875 1880 1885 |

| gct gat gat ctc ctg aaa tgc ttg gat gac att gaa aaa aaa tta | 5908 |
| Ala Asp Asp Leu Leu Lys Cys Leu Asp Asp Ile Glu Lys Lys Leu |
| 1890 1895 1900 |

| gcc agc cta cct gag ccc aga gat gaa agg aaa ata aag gaa att | 5953 |
| Ala Ser Leu Pro Glu Pro Arg Asp Glu Arg Lys Ile Lys Glu Ile |
| 1905 1910 1915 |

| gat cgg gaa ttg cag aag aag aaa gag gag ctg aat gca gtg cgt | 5998 |
| Asp Arg Glu Leu Gln Lys Lys Lys Glu Glu Leu Asn Ala Val Arg |
| 1920 1925 1930 |

| agg caa gct gag ggc ttg tct gag gat ggg gcc gca atg gca gtg | 6043 |
| Arg Gln Ala Glu Gly Leu Ser Glu Asp Gly Ala Ala Met Ala Val |
| 1935 1940 1945 |

| gag cca act cag atc cag ctc agc aag cgc tgg cgg gaa att gag | 6088 |
| Glu Pro Thr Gln Ile Gln Leu Ser Lys Arg Trp Arg Glu Ile Glu |

-continued

|  |  |  |  |  |
|---|---|---|---|---|
| | 1950 | 1955 | 1960 | |
| agc aaa ttt gct cag<br>Ser Lys Phe Ala Gln<br>1965 | ttt cga aga ctc aac<br>Phe Arg Arg Leu Asn<br>1970 | ttt gca caa att cac<br>Phe Ala Gln Ile His<br>1975 | | 6133 |
| act gtc cgt gaa gaa<br>Thr Val Arg Glu Glu<br>1980 | acg atg atg gtg atg<br>Thr Met Met Val Met<br>1985 | act gaa gac atg cct<br>Thr Glu Asp Met Pro<br>1990 | | 6178 |
| ttg gaa att tct tat<br>Leu Glu Ile Ser Tyr<br>1995 | gtg cct tct act tat<br>Val Pro Ser Thr Tyr<br>2000 | ttg act gaa atc act<br>Leu Thr Glu Ile Thr<br>2005 | | 6223 |
| cat gtc tca caa gcc<br>His Val Ser Gln Ala<br>2010 | cta tta gaa gtg gaa<br>Leu Leu Glu Val Glu<br>2015 | caa ctt ctc aat gct<br>Gln Leu Leu Asn Ala<br>2020 | | 6268 |
| cct gac ctc tgt gct<br>Pro Asp Leu Cys Ala<br>2025 | aag gac ttt gaa gat<br>Lys Asp Phe Glu Asp<br>2030 | ctc ttt aag caa gag<br>Leu Phe Lys Gln Glu<br>2035 | | 6313 |
| gag tct ctg aag aat<br>Glu Ser Leu Lys Asn<br>2040 | ata aaa gat agt cta<br>Ile Lys Asp Ser Leu<br>2045 | caa caa agc tca ggt<br>Gln Gln Ser Ser Gly<br>2050 | | 6358 |
| cgg att gac att att<br>Arg Ile Asp Ile Ile<br>2055 | cat agc aag aag aca<br>His Ser Lys Lys Thr<br>2060 | gca gca ttg caa agt<br>Ala Ala Leu Gln Ser<br>2065 | | 6403 |
| gca acg cct gtg gaa<br>Ala Thr Pro Val Glu<br>2070 | agg gtg aag cta cag<br>Arg Val Lys Leu Gln<br>2075 | gaa gct ctc tcc cag<br>Glu Ala Leu Ser Gln<br>2080 | | 6448 |
| ctt gat ttc caa tgg<br>Leu Asp Phe Gln Trp<br>2085 | gaa aaa gtt aac aaa<br>Glu Lys Val Asn Lys<br>2090 | atg tac aag gac cga<br>Met Tyr Lys Asp Arg<br>2095 | | 6493 |
| caa ggg cga ttt gac<br>Gln Gly Arg Phe Asp<br>2100 | aga tct gtt gag aaa<br>Arg Ser Val Glu Lys<br>2105 | tgg cgg cgt ttt cat<br>Trp Arg Arg Phe His<br>2110 | | 6538 |
| tat gat ata aag ata<br>Tyr Asp Ile Lys Ile<br>2115 | ttt aat cag tgg cta<br>Phe Asn Gln Trp Leu<br>2120 | aca gaa gct gaa cag<br>Thr Glu Ala Glu Gln<br>2125 | | 6583 |
| ttt ctc aga aag aca<br>Phe Leu Arg Lys Thr<br>2130 | caa att cct gag aat<br>Gln Ile Pro Glu Asn<br>2135 | tgg gaa cat gct aaa<br>Trp Glu His Ala Lys<br>2140 | | 6628 |
| tac aaa tgg tat ctt<br>Tyr Lys Trp Tyr Leu<br>2145 | aag gaa ctc cag gat<br>Lys Glu Leu Gln Asp<br>2150 | ggc att ggg cag cgg<br>Gly Ile Gly Gln Arg<br>2155 | | 6673 |
| caa act gtt gtc aga<br>Gln Thr Val Val Arg<br>2160 | aca ttg aat gca act<br>Thr Leu Asn Ala Thr<br>2165 | ggg gaa gaa ata att<br>Gly Glu Glu Ile Ile<br>2170 | | 6718 |
| cag caa tcc tca aaa<br>Gln Gln Ser Ser Lys<br>2175 | aca gat gcc agt att<br>Thr Asp Ala Ser Ile<br>2180 | cta cag gaa aaa ttg<br>Leu Gln Glu Lys Leu<br>2185 | | 6763 |
| gga agc ctg aat ctg<br>Gly Ser Leu Asn Leu<br>2190 | cgg tgg cag gag gtc<br>Arg Trp Gln Glu Val<br>2195 | tgc aaa cag ctg tca<br>Cys Lys Gln Leu Ser<br>2200 | | 6808 |
| gac aga aaa aag agg<br>Asp Arg Lys Lys Arg<br>2205 | cta gaa gaa caa aag<br>Leu Glu Glu Gln Lys<br>2210 | aat atc ttg tca gaa<br>Asn Ile Leu Ser Glu<br>2215 | | 6853 |
| ttt caa aga gat tta<br>Phe Gln Arg Asp Leu<br>2220 | aat gaa ttt gtt tta<br>Asn Glu Phe Val Leu<br>2225 | tgg ttg gag gaa gca<br>Trp Leu Glu Glu Ala<br>2230 | | 6898 |
| gat aac att gct agt<br>Asp Asn Ile Ala Ser<br>2235 | atc cca ctt gaa cct<br>Ile Pro Leu Glu Pro<br>2240 | gga aaa gag cag caa<br>Gly Lys Glu Gln Gln<br>2245 | | 6943 |
| cta aaa gaa aag ctt<br> | gag caa gtc aag tta<br> | ctg gtg gaa gag ttg<br> | | 6988 |

```
                Leu Lys Glu Lys Leu    Glu Gln Val Lys Leu    Leu Val Glu Glu Leu
                            2250                   2255                   2260 ccc ctg cgc cag gga    att ctc aaa caa tta    aat gaa act gga gga                    7033
Pro Leu Arg Gln Gly    Ile Leu Lys Gln Leu    Asn Glu Thr Gly Gly
            2265                   2270                   2275 ccc gtg ctt gta agt    gct ccc ata agc cca    gaa gag caa gat aaa                    7078
Pro Val Leu Val Ser    Ala Pro Ile Ser Pro    Glu Glu Gln Asp Lys
            2280                   2285                   2290 ctt gaa aat aag ctc    aag cag aca aat ctc    cag tgg ata aag gtt                    7123
Leu Glu Asn Lys Leu    Lys Gln Thr Asn Leu    Gln Trp Ile Lys Val
            2295                   2300                   2305 tcc aga gct tta cct    gag aaa caa gga gaa    att gaa gct caa ata                    7168
Ser Arg Ala Leu Pro    Glu Lys Gln Gly Glu    Ile Glu Ala Gln Ile
            2310                   2315                   2320 aaa gac ctt ggg cag    ctt gaa aaa aag ctt    gaa gac ctt gaa gag                    7213
Lys Asp Leu Gly Gln    Leu Glu Lys Lys Leu    Glu Asp Leu Glu Glu
            2325                   2330                   2335 cag tta aat cat ctg    ctg ctg tgg tta tct    cct att agg aat cag                    7258
Gln Leu Asn His Leu    Leu Leu Trp Leu Ser    Pro Ile Arg Asn Gln
            2340                   2345                   2350 ttg gaa att tat aac    caa cca aac caa gaa    gga cca ttt gac gtt                    7303
Leu Glu Ile Tyr Asn    Gln Pro Asn Gln Glu    Gly Pro Phe Asp Val
            2355                   2360                   2365 aag gaa act gaa ata    gca gtt caa gct aaa    caa ccg gat gtg gaa                    7348
Lys Glu Thr Glu Ile    Ala Val Gln Ala Lys    Gln Pro Asp Val Glu
            2370                   2375                   2380 gag att ttg tct aaa    ggg cag cat ttg tac    aag gaa aaa cca gcc                    7393
Glu Ile Leu Ser Lys    Gly Gln His Leu Tyr    Lys Glu Lys Pro Ala
            2385                   2390                   2395 act cag cca gtg aag    agg aag tta gaa gat    ctg agc tct gag tgg                    7438
Thr Gln Pro Val Lys    Arg Lys Leu Glu Asp    Leu Ser Ser Glu Trp
            2400                   2405                   2410 aag gcg gta aac cgt    tta ctt caa gag ctg    agg gca aag cag cct                    7483
Lys Ala Val Asn Arg    Leu Leu Gln Glu Leu    Arg Ala Lys Gln Pro
            2415                   2420                   2425 gac cta gct cct gga    ctg acc act att gga    gcc tct cct act cag                    7528
Asp Leu Ala Pro Gly    Leu Thr Thr Ile Gly    Ala Ser Pro Thr Gln
            2430                   2435                   2440 act gtt act ctg gtg    aca caa cct gtg gtt    act aag gaa act gcc                    7573
Thr Val Thr Leu Val    Thr Gln Pro Val Val    Thr Lys Glu Thr Ala
            2445                   2450                   2455 atc tcc aaa cta gaa    atg cca tct tcc ttg    atg ttg gag gta cct                    7618
Ile Ser Lys Leu Glu    Met Pro Ser Ser Leu    Met Leu Glu Val Pro
            2460                   2465                   2470 gct ctg gca gat ttc    aac cgg gct tgg aca    gaa ctt acc gac tgg                    7663
Ala Leu Ala Asp Phe    Asn Arg Ala Trp Thr    Glu Leu Thr Asp Trp
            2475                   2480                   2485 ctt tct ctg ctt gat    caa gtt ata aaa tca    cag agg gtg atg gtg                    7708
Leu Ser Leu Leu Asp    Gln Val Ile Lys Ser    Gln Arg Val Met Val
            2490                   2495                   2500 ggt gac ctt gag gat    atc aac gag atg atc    atc aag cag aag gca                    7753
Gly Asp Leu Glu Asp    Ile Asn Glu Met Ile    Ile Lys Gln Lys Ala
            2505                   2510                   2515 aca atg cag gat ttg    gaa cag agg cgt ccc    cag ttg gaa gaa ctc                    7798
Thr Met Gln Asp Leu    Glu Gln Arg Arg Pro    Gln Leu Glu Glu Leu
            2520                   2525                   2530 att acc gct gcc caa    aat ttg aaa aac aag    acc agc aat caa gag                    7843
Ile Thr Ala Ala Gln    Asn Leu Lys Asn Lys    Thr Ser Asn Gln Glu
            2535                   2540                   2545
```

-continued

```
gct aga aca atc att acg gat cga att gaa aga att cag aat cag        7888
Ala Arg Thr Ile Ile Thr Asp Arg Ile Glu Arg Ile Gln Asn Gln
            2550                2555                2560 tgg gat gaa gta caa gaa cac ctt cag aac cgg agg caa cag ttg        7933
Trp Asp Glu Val Gln Glu His Leu Gln Asn Arg Arg Gln Gln Leu
            2565                2570                2575 aat gaa atg tta aag gat tca aca caa tgg ctg gaa gct aag gaa        7978
Asn Glu Met Leu Lys Asp Ser Thr Gln Trp Leu Glu Ala Lys Glu
            2580                2585                2590 gaa gct gag cag gtc tta gga cag gcc aga gcc aag ctt gag tca        8023
Glu Ala Glu Gln Val Leu Gly Gln Ala Arg Ala Lys Leu Glu Ser
            2595                2600                2605 tgg aag gag ggt ccc tat aca gta gat gca atc caa aag aaa atc        8068
Trp Lys Glu Gly Pro Tyr Thr Val Asp Ala Ile Gln Lys Lys Ile
            2610                2615                2620 aca gaa acc aag cag ttg gcc aaa gac ctc cgc cag tgg cag aca        8113
Thr Glu Thr Lys Gln Leu Ala Lys Asp Leu Arg Gln Trp Gln Thr
            2625                2630                2635 aat gta gat gtg gca aat gac ttg gcc ctg aaa ctt ctc cgg gat        8158
Asn Val Asp Val Ala Asn Asp Leu Ala Leu Lys Leu Leu Arg Asp
            2640                2645                2650 tat tct gca gat gat acc aga aaa gtc cac atg ata aca gag aat        8203
Tyr Ser Ala Asp Asp Thr Arg Lys Val His Met Ile Thr Glu Asn
            2655                2660                2665 atc aat gcc tct tgg aga agc att cat aaa agg gtg agt gag cga        8248
Ile Asn Ala Ser Trp Arg Ser Ile His Lys Arg Val Ser Glu Arg
            2670                2675                2680 gag gct gct ttg gaa gaa act cat aga tta ctg caa cag ttc ccc        8293
Glu Ala Ala Leu Glu Glu Thr His Arg Leu Leu Gln Gln Phe Pro
            2685                2690                2695 ctg gac ctg gaa aag ttt ctt gcc tgg ctt aca gaa gct gaa aca        8338
Leu Asp Leu Glu Lys Phe Leu Ala Trp Leu Thr Glu Ala Glu Thr
            2700                2705                2710 act gcc aat gtc cta cag gat gct acc cgt aag gaa agg ctc cta        8383
Thr Ala Asn Val Leu Gln Asp Ala Thr Arg Lys Glu Arg Leu Leu
            2715                2720                2725 gaa gac tcc aag gga gta aaa gag ctg atg aaa caa tgg caa gac        8428
Glu Asp Ser Lys Gly Val Lys Glu Leu Met Lys Gln Trp Gln Asp
            2730                2735                2740 ctc caa ggt gaa att gaa gct cac aca gat gtt tat cac aac ctg        8473
Leu Gln Gly Glu Ile Glu Ala His Thr Asp Val Tyr His Asn Leu
            2745                2750                2755 gat gaa aac agc caa aaa atc ctg aga tcc ctg gaa ggt tcc gat        8518
Asp Glu Asn Ser Gln Lys Ile Leu Arg Ser Leu Glu Gly Ser Asp
            2760                2765                2770 gat gca gtc ctg tta caa aga cgt ttg gat aac atg aac ttc aag        8563
Asp Ala Val Leu Leu Gln Arg Arg Leu Asp Asn Met Asn Phe Lys
            2775                2780                2785 tgg agt gaa ctt cgg aaa aag tct ctc aac att agg tcc cat ttg        8608
Trp Ser Glu Leu Arg Lys Lys Ser Leu Asn Ile Arg Ser His Leu
            2790                2795                2800 gaa gcc agt tct gac cag tgg aag cgt ctg cac ctt tct ctg cag        8653
Glu Ala Ser Ser Asp Gln Trp Lys Arg Leu His Leu Ser Leu Gln
            2805                2810                2815 gaa ctt ctg gtg tgg cta cag ctg aaa gat gat gaa tta agc cgg        8698
Glu Leu Leu Val Trp Leu Gln Leu Lys Asp Asp Glu Leu Ser Arg
            2820                2825                2830 cag gca cct att gga ggc gac ttt cca gca gtt cag aag cag aac        8743
Gln Ala Pro Ile Gly Gly Asp Phe Pro Ala Val Gln Lys Gln Asn
            2835                2840                2845
```

|  |  |
|---|---|
| gat gta cat agg gcc ttc aag agg gaa ttg aaa act aaa gaa cct<br>Asp Val His Arg Ala Phe Lys Arg Glu Leu Lys Thr Lys Glu Pro<br>                           2850                            2855                       2860 | 8788 |
| gta atc atg agt act ctt gag act gta cga ata ttt ctg aca gag<br>Val Ile Met Ser Thr Leu Glu Thr Val Arg Ile Phe Leu Thr Glu<br>                           2865                            2870                       2875 | 8833 |
| cag cct ttg gaa gga cta gag aaa ctc tac cag gag ccc aga gag<br>Gln Pro Leu Glu Gly Leu Glu Lys Leu Tyr Gln Glu Pro Arg Glu<br>                           2880                            2885                       2890 | 8878 |
| ctg cct cct gag gag aga gcc cag aat gtc act cgg ctt cta cga<br>Leu Pro Pro Glu Glu Arg Ala Gln Asn Val Thr Arg Leu Leu Arg<br>                           2895                            2900                       2905 | 8923 |
| aag cag gct gag gag gtc aat act gag tgg gaa aaa ttg aac ctg<br>Lys Gln Ala Glu Glu Val Asn Thr Glu Trp Glu Lys Leu Asn Leu<br>                           2910                            2915                       2920 | 8968 |
| cac tcc gct gac tgg cag aga aaa ata gat gag acc ctt gaa aga<br>His Ser Ala Asp Trp Gln Arg Lys Ile Asp Glu Thr Leu Glu Arg<br>                           2925                            2930                       2935 | 9013 |
| ctc cag gaa ctt caa gag gcc acg gat gag ctg gac ctc aag ctg<br>Leu Gln Glu Leu Gln Glu Ala Thr Asp Glu Leu Asp Leu Lys Leu<br>                           2940                            2945                       2950 | 9058 |
| cgc caa gct gag gtg atc aag gga tcc tgg cag ccc gtg ggc gat<br>Arg Gln Ala Glu Val Ile Lys Gly Ser Trp Gln Pro Val Gly Asp<br>                           2955                            2960                       2965 | 9103 |
| ctc ctc att gac tct ctc caa gat cac ctc gag aaa gtc aag gca<br>Leu Leu Ile Asp Ser Leu Gln Asp His Leu Glu Lys Val Lys Ala<br>                           2970                            2975                       2980 | 9148 |
| ctt cga gga gaa att gcg cct ctg aaa gag aac gtg agc cac gtc<br>Leu Arg Gly Glu Ile Ala Pro Leu Lys Glu Asn Val Ser His Val<br>                           2985                            2990                       2995 | 9193 |
| aat gac ctt gct cgc cag ctt acc act ttg ggc att cag ctc tca<br>Asn Asp Leu Ala Arg Gln Leu Thr Thr Leu Gly Ile Gln Leu Ser<br>                           3000                            3005                       3010 | 9238 |
| ccg tat aac ctc agc act ctg gaa gac ctg aac acc aga tgg aag<br>Pro Tyr Asn Leu Ser Thr Leu Glu Asp Leu Asn Thr Arg Trp Lys<br>                           3015                            3020                       3025 | 9283 |
| ctt ctg cag gtg gcc gtc gag gac cga gtc agg cag ctg cat gaa<br>Leu Leu Gln Val Ala Val Glu Asp Arg Val Arg Gln Leu His Glu<br>                           3030                            3035                       3040 | 9328 |
| gcc cac agg gac ttt ggt cca gca tct cag cac ttt ctt tcc acg<br>Ala His Arg Asp Phe Gly Pro Ala Ser Gln His Phe Leu Ser Thr<br>                           3045                            3050                       3055 | 9373 |
| tct gtc cag ggt ccc tgg gag aga gcc atc tcg cca aac aaa gtg<br>Ser Val Gln Gly Pro Trp Glu Arg Ala Ile Ser Pro Asn Lys Val<br>                           3060                            3065                       3070 | 9418 |
| ccc tac tat atc aac cac gag act caa aca act tgc tgg gac cat<br>Pro Tyr Tyr Ile Asn His Glu Thr Gln Thr Thr Cys Trp Asp His<br>                           3075                            3080                       3085 | 9463 |
| ccc aaa atg aca gag ctc tac cag tct tta gct gac ctg aat aat<br>Pro Lys Met Thr Glu Leu Tyr Gln Ser Leu Ala Asp Leu Asn Asn<br>                           3090                            3095                       3100 | 9508 |
| gtc aga ttc tca gct tat agg act gcc atg aaa ctc cga aga ctg<br>Val Arg Phe Ser Ala Tyr Arg Thr Ala Met Lys Leu Arg Arg Leu<br>                           3105                            3110                       3115 | 9553 |
| cag aag gcc ctt tgc ttg gat ctc ttg agc ctg tca gct gca tgt<br>Gln Lys Ala Leu Cys Leu Asp Leu Leu Ser Leu Ser Ala Ala Cys<br>                           3120                            3125                       3130 | 9598 |
| gat gcc ttg gac cag cac aac ctc aag caa aat gac cag ccc atg<br>Asp Ala Leu Asp Gln His Asn Leu Lys Gln Asn Asp Gln Pro Met | 9643 |

-continued

| | | | | | | | | | | | | | | |
|---|---|---|---|---|---|---|---|---|---|---|---|---|---|---|
| | | 3135 | | | | 3140 | | | | | 3145 | | | |
| gat | atc | ctg | cag | att | att | aat | tgt | ttg | acc | act | att | tat | gac | cgc | 9688 |
| Asp | Ile | Leu | Gln | Ile | Ile | Asn | Cys | Leu | Thr | Thr | Ile | Tyr | Asp | Arg | |
| | | 3150 | | | | 3155 | | | | | 3160 | | | | |
| ctg | gag | caa | gag | cac | aac | aat | ttg | gtc | aac | gtc | cct | ctc | tgc | gtg | 9733 |
| Leu | Glu | Gln | Glu | His | Asn | Asn | Leu | Val | Asn | Val | Pro | Leu | Cys | Val | |
| | | 3165 | | | | 3170 | | | | | 3175 | | | | |
| gat | atg | tgt | ctg | aac | tgg | ctg | ctg | aat | gtt | tat | gat | acg | gga | cga | 9778 |
| Asp | Met | Cys | Leu | Asn | Trp | Leu | Leu | Asn | Val | Tyr | Asp | Thr | Gly | Arg | |
| | | 3180 | | | | 3185 | | | | | 3190 | | | | |
| aca | ggg | agg | atc | cgt | gtc | ctg | tct | ttt | aaa | act | ggc | atc | att | tcc | 9823 |
| Thr | Gly | Arg | Ile | Arg | Val | Leu | Ser | Phe | Lys | Thr | Gly | Ile | Ile | Ser | |
| | | 3195 | | | | 3200 | | | | | 3205 | | | | |
| ctg | tgt | aaa | gca | cat | ttg | gaa | gac | aag | tac | aga | tac | ctt | ttc | aag | 9868 |
| Leu | Cys | Lys | Ala | His | Leu | Glu | Asp | Lys | Tyr | Arg | Tyr | Leu | Phe | Lys | |
| | | 3210 | | | | 3215 | | | | | 3220 | | | | |
| caa | gtg | gca | agt | tca | aca | gga | ttt | tgt | gac | cag | cgc | agg | ctg | ggc | 9913 |
| Gln | Val | Ala | Ser | Ser | Thr | Gly | Phe | Cys | Asp | Gln | Arg | Arg | Leu | Gly | |
| | | 3225 | | | | 3230 | | | | | 3235 | | | | |
| ctc | ctt | ctg | cat | gat | tct | atc | caa | att | cca | aga | cag | ttg | ggt | gaa | 9958 |
| Leu | Leu | Leu | His | Asp | Ser | Ile | Gln | Ile | Pro | Arg | Gln | Leu | Gly | Glu | |
| | | 3240 | | | | 3245 | | | | | 3250 | | | | |
| gtt | gca | tcc | ttt | ggg | ggc | agt | aac | att | gag | cca | agt | gtc | cgg | agc | 10003 |
| Val | Ala | Ser | Phe | Gly | Gly | Ser | Asn | Ile | Glu | Pro | Ser | Val | Arg | Ser | |
| | | 3255 | | | | 3260 | | | | | 3265 | | | | |
| tgc | ttc | caa | ttt | gct | aat | aat | aag | cca | gag | atc | gaa | gcg | gcc | ctc | 10048 |
| Cys | Phe | Gln | Phe | Ala | Asn | Asn | Lys | Pro | Glu | Ile | Glu | Ala | Ala | Leu | |
| | | 3270 | | | | 3275 | | | | | 3280 | | | | |
| ttc | cta | gac | tgg | atg | aga | ctg | gaa | ccc | cag | tcc | atg | gtg | tgg | ctg | 10093 |
| Phe | Leu | Asp | Trp | Met | Arg | Leu | Glu | Pro | Gln | Ser | Met | Val | Trp | Leu | |
| | | 3285 | | | | 3290 | | | | | 3295 | | | | |
| ccc | gtc | ctg | cac | aga | gtg | gct | gct | gca | gaa | act | gcc | aag | cat | cag | 10138 |
| Pro | Val | Leu | His | Arg | Val | Ala | Ala | Ala | Glu | Thr | Ala | Lys | His | Gln | |
| | | 3300 | | | | 3305 | | | | | 3310 | | | | |
| gcc | aaa | tgt | aac | atc | tgc | aaa | gag | tgt | cca | atc | att | gga | ttc | agg | 10183 |
| Ala | Lys | Cys | Asn | Ile | Cys | Lys | Glu | Cys | Pro | Ile | Ile | Gly | Phe | Arg | |
| | | 3315 | | | | 3320 | | | | | 3325 | | | | |
| tac | agg | agt | cta | aag | cac | ttt | aat | tat | gac | atc | tgc | caa | agc | tgc | 10228 |
| Tyr | Arg | Ser | Leu | Lys | His | Phe | Asn | Tyr | Asp | Ile | Cys | Gln | Ser | Cys | |
| | | 3330 | | | | 3335 | | | | | 3340 | | | | |
| ttt | ttt | tct | ggt | cga | gtt | gca | aaa | ggc | cat | aaa | atg | cac | tat | ccc | 10273 |
| Phe | Phe | Ser | Gly | Arg | Val | Ala | Lys | Gly | His | Lys | Met | His | Tyr | Pro | |
| | | 3345 | | | | 3350 | | | | | 3355 | | | | |
| atg | gtg | gaa | tat | tgc | act | ccg | act | aca | tca | gga | gaa | gat | gtt | cga | 10318 |
| Met | Val | Glu | Tyr | Cys | Thr | Pro | Thr | Thr | Ser | Gly | Glu | Asp | Val | Arg | |
| | | 3360 | | | | 3365 | | | | | 3370 | | | | |
| gac | ttt | gcc | aag | gta | cta | aaa | aac | aaa | ttt | cga | acc | aaa | agg | tat | 10363 |
| Asp | Phe | Ala | Lys | Val | Leu | Lys | Asn | Lys | Phe | Arg | Thr | Lys | Arg | Tyr | |
| | | 3375 | | | | 3380 | | | | | 3385 | | | | |
| ttt | gcg | aag | cat | ccc | cga | atg | ggc | tac | ctg | cca | gtg | cag | act | gtc | 10408 |
| Phe | Ala | Lys | His | Pro | Arg | Met | Gly | Tyr | Leu | Pro | Val | Gln | Thr | Val | |
| | | 3390 | | | | 3395 | | | | | 3400 | | | | |
| tta | gag | ggg | gac | aac | atg | gaa | act | ccc | gtt | act | ctg | atc | aac | ttc | 10453 |
| Leu | Glu | Gly | Asp | Asn | Met | Glu | Thr | Pro | Val | Thr | Leu | Ile | Asn | Phe | |
| | | 3405 | | | | 3410 | | | | | 3415 | | | | |
| tgg | cca | gta | gat | tct | gcg | cct | gcc | tcg | tcc | cct | cag | ctt | tca | cac | 10498 |
| Trp | Pro | Val | Asp | Ser | Ala | Pro | Ala | Ser | Ser | Pro | Gln | Leu | Ser | His | |
| | | 3420 | | | | 3425 | | | | | 3430 | | | | |
| gat | gat | act | cat | tca | cgc | att | gaa | cat | tat | gct | agc | agg | cta | gca | 10543 |

```
Asp Asp Thr His Ser  Arg Ile Glu His Tyr  Ala Ser Arg Leu Ala
            3435                3440                3445 gaa atg gaa aac agc  aat gga tct tat cta  aat gat agc atc tct       10588
Glu Met Glu Asn Ser  Asn Gly Ser Tyr Leu  Asn Asp Ser Ile Ser
            3450                3455                3460 cct aat gag agc ata  gat gat gaa cat ttg  tta atc cag cat tac       10633
Pro Asn Glu Ser Ile  Asp Asp Glu His Leu  Leu Ile Gln His Tyr
            3465                3470                3475 tgc caa agt ttg aac  cag gac tcc ccc ctg  agc cag cct cgt agt       10678
Cys Gln Ser Leu Asn  Gln Asp Ser Pro Leu  Ser Gln Pro Arg Ser
            3480                3485                3490 cct gcc cag atc ttg  att tcc tta gag agt  gag gaa aga ggg gag       10723
Pro Ala Gln Ile Leu  Ile Ser Leu Glu Ser  Glu Glu Arg Gly Glu
            3495                3500                3505 cta gag aga atc cta  gca gat ctt gag gaa  gaa aac agg aat ctg       10768
Leu Glu Arg Ile Leu  Ala Asp Leu Glu Glu  Glu Asn Arg Asn Leu
            3510                3515                3520 caa gca gaa tat gac  cgt cta aag cag cag  cac gaa cat aaa ggc       10813
Gln Ala Glu Tyr Asp  Arg Leu Lys Gln Gln  His Glu His Lys Gly
            3525                3530                3535 ctg tcc cca ctg ccg  tcc cct cct gaa atg  atg ccc acc tct ccc       10858
Leu Ser Pro Leu Pro  Ser Pro Pro Glu Met  Met Pro Thr Ser Pro
            3540                3545                3550 cag agt ccc cgg gat  gct gag ctc att gct  gag gcc aag cta ctg       10903
Gln Ser Pro Arg Asp  Ala Glu Leu Ile Ala  Glu Ala Lys Leu Leu
            3555                3560                3565 cgt caa cac aaa ggc  cgc ctg gaa gcc agg  atg caa atc ctg gaa       10948
Arg Gln His Lys Gly  Arg Leu Glu Ala Arg  Met Gln Ile Leu Glu
            3570                3575                3580 gac cac aat aaa cag  ctg gag tca cag tta  cac agg cta agg cag       10993
Asp His Asn Lys Gln  Leu Glu Ser Gln Leu  His Arg Leu Arg Gln
            3585                3590                3595 ctg ctg gag caa ccc  cag gca gag gcc aaa  gtg aat ggc aca acg       11038
Leu Leu Glu Gln Pro  Gln Ala Glu Ala Lys  Val Asn Gly Thr Thr
            3600                3605                3610 gtg tcc tct cct tct  acc tct cta cag agg  tcc gac agc agt cag       11083
Val Ser Ser Pro Ser  Thr Ser Leu Gln Arg  Ser Asp Ser Ser Gln
            3615                3620                3625 cct atg ctg ctc cga  gtg gtt ggc agt caa  act tcg gac tcc atg       11128
Pro Met Leu Leu Arg  Val Val Gly Ser Gln  Thr Ser Asp Ser Met
            3630                3635                3640 ggt gag gaa gat ctt  ctc agt cct ccc cag  gac aca agc aca ggg       11173
Gly Glu Glu Asp Leu  Leu Ser Pro Pro Gln  Asp Thr Ser Thr Gly
            3645                3650                3655 tta gag gag gtg atg  gag caa ctc aac aac  tcc ttc cct agt tca       11218
Leu Glu Glu Val Met  Glu Gln Leu Asn Asn  Ser Phe Pro Ser Ser
            3660                3665                3670 aga gga aga aat acc  cct gga aag cca atg  aga gag gac aca atg       11263
Arg Gly Arg Asn Thr  Pro Gly Lys Pro Met  Arg Glu Asp Thr Met
            3675                3680                3685 tag gaagtctttt ccacatggca gatgatttgg gcagagcgat ggagtcctta          11316
gtatcagtca tgacagatga agaaggagca gaataaatgt tttacaactc ctgattcccg   11376
catggttttt ataatattca tacaacaaag aggattagac agtaagagtt tacaagaaat   11436
aaatctatat ttttgtgaag ggtagtggta ttatactgta gatttcagta gtttctaagt   11496
ctgttattgt tttgttaaca atggcaggtt ttacacgtct atgcaattgt acaaaaaagt   11556
tataagaaaa ctacatgtaa aatcttgata gctaaataac ttgccatttc tttatatgga   11616
```

-continued

```
acgcattttg ggttgtttaa aaatttataa cagttataaa gaaagattgt aaactaaagt    11676
gtgctttata aaaaaaagtt gtttataaaa acccctaaaa acaaaacaaa cacacacaca    11736
cacacataca cacacacaca caaaactttg aggcagcgca ttgttttgca tccttttggc    11796
gtgatatcca tatgaaattc atggctttt ctttttttgc atattaaaga taagacttcc     11856
tctaccacca caccaaatga ctactacaca ctgctcattt gagaactgtc agctgagtgg    11916
ggcaggcttg agttttcatt tcatatatct atatgtctat aagtatataa atactatagt    11976
tatatagata aagagatacg aatttctata gactgacttt ttccattttt taaatgttca    12036
tgtcacatcc taatagaaag aaattacttc tagtcagtca tccaggctta cctgcttggt    12096
ctagaatgga ttttcccgg agccggaagc caggaggaaa ctacaccaca ctaaaacatt     12156
gtctacagct ccagatgttt ctcatttta acaactttcc actgacaacg aaagtaaagt     12216
aaagtattgg attttttaa agggaacatg tgaatgaata cacaggactt attatatcag     12276
agtgagtaat cggttggttg gttgattgat tgattgattg atacattcag cttcctgctg    12336
ctagcaatgc cacgatttag atttaatgat gcttcagtgg aaatcaatca gaaggtattc    12396
tgaccttgtg aacatcagaa ggtattttt aactcccaag cagtagcagg acgatgatag     12456
ggctggaggg ctatggattc ccagcccatc cctgtgaagg agtaggccac tctttaagtg    12516
aaggattgga tgattgttca taatacataa agttctctgt aattacaact aaattattat    12576
gccctcttct cacagtcaaa aggaactggg tggtttggtt tttgttgctt ttttagattt    12636
attgtcccat gtgggatgag tttttaaatg ccacaagaca taatttaaaa taaataaact    12696
ttgggaaaag gtgtaagaca gtagccccat cacatttgtg atactgacag gtatcaaccc    12756
agaagcccat gaactgtgtt tccatccttt gcatttctct gcgagtagtt ccacacaggt    12816
ttgtaagtaa gtaagaaaga aggcaaattg attcaaatgt tacaaaaaaa cccttcttgg    12876
tggattagac aggttaaata tataaacaaa caaacaaaaa ttgctcaaaa aagaggagaa    12936
aagctcaaga ggaaaagcta aggactggta ggaaaaagct ttactctttc atgccatttt    12996 atttctttt gatttttaaa tcattcattc aatagatacc accgtgtgac ctataattt     13056 gcaaatctgt tacctctgac atcaagtgta attagctttt ggagagtggg ctgacatcaa    13116
gtgtaattag cttttggaga gtgggttttg tccattatta ataattaatt aattaacatc    13176
aaacacggct tctcatgcta tttctacctc actttggttt tggggtgttc ctgataattg    13236
tgcacacctg agttcacagc ttcaccactt gtccattgcg ttattttctt tttcctttat    13296
aattctttct ttttccttca taattttcaa agaaaaccc aaagctctaa ggtaacaaat     13356
taccaaatta catgaagatt tggttttgt cttgcatttt tttccttat gtgacgctgg      13416 acctttctt tacccaagga tttttaaaac tcagatttaa aacaaggggt tactttacat     13476
cctactaaga agtttaagta agtaagtttc attctaaaat cagaggtaaa tagagtgcat    13536
aaataatttt gttttaatct ttttgttttt cttttagaca cattagctct ggagtgagtc    13596
tgtcataata tttgaacaaa aattgagagc tttattgctg cattttaagc ataattaatt    13656
tggacattat ttcgtgttgt gttctttata accaccgagt attaaactgt aaatcataat    13716
gtaactgaag cataaacatc acatggcatg ttttgtcatt gttttcaggt actgagttct    13776
tacttgagta tcataatata ttgtgtttta acaccaacac tgtaacattt acgaattatt    13836
tttttaaact tcagttttac tgcattttca caacatatca gacttcacca aatatatgcc    13896
ttactattgt attatagtac tgctttactg tgtatctcaa taaagcacgc agttatgtta    13956
c                                                                   13957
```

<210> SEQ ID NO 2
<211> LENGTH: 3685
<212> TYPE: PRT
<213> ORGANISM: Homo sapiens

<400> SEQUENCE: 2

```
Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
    290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly
```

-continued

```
            370                 375                 380
Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Arg Val
                435                 440                 445

Leu Met Asp Leu Gln Asn Gln Lys Leu Lys Glu Leu Asn Asp Trp Leu
450                 455                 460

Thr Lys Thr Glu Glu Arg Thr Arg Lys Met Glu Glu Pro Leu Gly
465                 470                 475                 480

Pro Asp Leu Glu Asp Leu Lys Arg Gln Val Gln Gln His Lys Val Leu
                485                 490                 495

Gln Glu Asp Leu Glu Gln Glu Gln Val Arg Val Asn Ser Leu Thr His
                500                 505                 510

Met Val Val Val Asp Glu Ser Ser Gly Asp His Ala Thr Ala Ala
            515                 520                 525

Leu Glu Glu Gln Leu Lys Val Leu Gly Asp Arg Trp Ala Asn Ile Cys
530                 535                 540

Arg Trp Thr Glu Asp Arg Trp Val Leu Leu Gln Asp Ile Leu Leu Lys
545                 550                 555                 560

Trp Gln Arg Leu Thr Glu Glu Gln Cys Leu Phe Ser Ala Trp Leu Ser
                565                 570                 575

Glu Lys Glu Asp Ala Val Asn Lys Ile His Thr Thr Gly Phe Lys Asp
                580                 585                 590

Gln Asn Glu Met Leu Ser Ser Leu Gln Lys Leu Ala Val Leu Lys Ala
            595                 600                 605

Asp Leu Glu Lys Lys Lys Gln Ser Met Gly Lys Leu Tyr Ser Leu Lys
                610                 615                 620

Gln Asp Leu Leu Ser Thr Leu Lys Asn Lys Ser Val Thr Gln Lys Thr
625                 630                 635                 640

Glu Ala Trp Leu Asp Asn Phe Ala Arg Cys Trp Asp Asn Leu Val Gln
                645                 650                 655

Lys Leu Glu Lys Ser Thr Ala Gln Ile Ser Gln Ala Val Thr Thr Thr
            660                 665                 670

Gln Pro Ser Leu Thr Gln Thr Thr Val Met Glu Thr Val Thr Thr Val
            675                 680                 685

Thr Thr Arg Glu Gln Ile Leu Val Lys His Ala Gln Glu Glu Leu Pro
690                 695                 700

Pro Pro Pro Pro Gln Lys Lys Arg Gln Ile Thr Val Asp Ser Glu Ile
705                 710                 715                 720

Arg Lys Arg Leu Asp Val Asp Ile Thr Glu Leu His Ser Trp Ile Thr
                725                 730                 735

Arg Ser Glu Ala Val Leu Gln Ser Pro Glu Phe Ala Ile Phe Arg Lys
            740                 745                 750

Glu Gly Asn Phe Ser Asp Leu Lys Glu Lys Val Asn Ala Ile Glu Arg
            755                 760                 765

Glu Lys Ala Glu Lys Phe Arg Lys Leu Gln Asp Ala Ser Arg Ser Ala
            770                 775                 780

Gln Ala Leu Val Glu Gln Met Val Asn Glu Gly Val Asn Ala Asp Ser
785                 790                 795                 800
```

Ile Lys Gln Ala Ser Glu Gln Leu Asn Ser Arg Trp Ile Glu Phe Cys
          805                 810                 815

Gln Leu Leu Ser Glu Arg Leu Asn Trp Leu Glu Tyr Gln Asn Asn Ile
          820                 825                 830

Ile Ala Phe Tyr Asn Gln Leu Gln Gln Leu Glu Gln Met Thr Thr Thr
          835                 840                 845

Ala Glu Asn Trp Leu Lys Ile Gln Pro Thr Thr Pro Ser Glu Pro Thr
          850                 855                 860

Ala Ile Lys Ser Gln Leu Lys Ile Cys Lys Asp Glu Val Asn Arg Leu
865                 870                 875                 880

Ser Gly Leu Gln Pro Gln Ile Glu Arg Leu Lys Ile Gln Ser Ile Ala
              885                 890                 895

Leu Lys Glu Lys Gly Gln Gly Pro Met Phe Leu Asp Ala Asp Phe Val
              900                 905                 910

Ala Phe Thr Asn His Phe Lys Gln Val Phe Ser Asp Val Gln Ala Arg
          915                 920                 925

Glu Lys Glu Leu Gln Thr Ile Phe Asp Thr Leu Pro Pro Met Arg Tyr
930                 935                 940

Gln Glu Thr Met Ser Ala Ile Arg Thr Trp Val Gln Gln Ser Glu Thr
945                 950                 955                 960

Lys Leu Ser Ile Pro Gln Leu Ser Val Thr Asp Tyr Glu Ile Met Glu
              965                 970                 975

Gln Arg Leu Gly Glu Leu Gln Ala Leu Gln Ser Ser Leu Gln Glu Gln
              980                 985                 990

Gln Ser Gly Leu Tyr Tyr Leu Ser Thr Thr Val Lys Glu Met Ser Lys
          995                 1000                1005

Lys Ala Pro Ser Glu Ile Ser Arg Lys Tyr Gln Ser Glu Phe Glu
          1010                1015                1020

Glu Ile Glu Gly Arg Trp Lys Lys Leu Ser Ser Gln Leu Val Glu
          1025                1030                1035

His Cys Gln Lys Leu Glu Glu Gln Met Asn Lys Leu Arg Lys Ile
          1040                1045                1050

Gln Asn His Ile Gln Thr Leu Lys Lys Trp Met Ala Glu Val Asp
          1055                1060                1065

Val Phe Leu Lys Glu Glu Trp Pro Ala Leu Gly Asp Ser Glu Ile
          1070                1075                1080

Leu Lys Lys Gln Leu Lys Gln Cys Arg Leu Leu Val Ser Asp Ile
          1085                1090                1095

Gln Thr Ile Gln Pro Ser Leu Asn Ser Val Asn Glu Gly Gly Gln
          1100                1105                1110

Lys Ile Lys Asn Glu Ala Glu Pro Glu Phe Ala Ser Arg Leu Glu
          1115                1120                1125

Thr Glu Leu Lys Glu Leu Asn Thr Gln Trp Asp His Met Cys Gln
          1130                1135                1140

Gln Val Tyr Ala Arg Lys Glu Ala Leu Lys Gly Gly Leu Glu Lys
          1145                1150                1155

Thr Val Ser Leu Gln Lys Asp Leu Ser Glu Met His Glu Trp Met
          1160                1165                1170

Thr Gln Ala Glu Glu Glu Tyr Leu Glu Arg Asp Phe Glu Tyr Lys
          1175                1180                1185

Thr Pro Asp Glu Leu Gln Lys Ala Val Glu Glu Met Lys Arg Ala
          1190                1195                1200

-continued

```
Lys Glu Glu Ala Gln Gln Lys Glu Ala Lys Val Lys Leu Leu Thr
1205                1210                1215

Glu Ser Val Asn Ser Val Ile Ala Gln Ala Pro Pro Val Ala Gln
1220                1225                1230

Glu Ala Leu Lys Lys Glu Leu Glu Thr Leu Thr Thr Asn Tyr Gln
1235                1240                1245

Trp Leu Cys Thr Arg Leu Asn Gly Lys Cys Lys Thr Leu Glu Glu
1250                1255                1260

Val Trp Ala Cys Trp His Glu Leu Leu Ser Tyr Leu Glu Lys Ala
1265                1270                1275

Asn Lys Trp Leu Asn Glu Val Glu Phe Lys Leu Lys Thr Thr Glu
1280                1285                1290

Asn Ile Pro Gly Gly Ala Glu Glu Ile Ser Glu Val Leu Asp Ser
1295                1300                1305

Leu Glu Asn Leu Met Arg His Ser Glu Asp Asn Pro Asn Gln Ile
1310                1315                1320

Arg Ile Leu Ala Gln Thr Leu Thr Asp Gly Gly Val Met Asp Glu
1325                1330                1335

Leu Ile Asn Glu Glu Leu Glu Thr Phe Asn Ser Arg Trp Arg Glu
1340                1345                1350

Leu His Glu Glu Ala Val Arg Arg Gln Lys Leu Leu Glu Gln Ser
1355                1360                1365

Ile Gln Ser Ala Gln Glu Thr Glu Lys Ser Leu His Leu Ile Gln
1370                1375                1380

Glu Ser Leu Thr Phe Ile Asp Lys Gln Leu Ala Ala Tyr Ile Ala
1385                1390                1395

Asp Lys Val Asp Ala Ala Gln Met Pro Gln Glu Ala Gln Lys Ile
1400                1405                1410

Gln Ser Asp Leu Thr Ser His Glu Ile Ser Leu Glu Glu Met Lys
1415                1420                1425

Lys His Asn Gln Gly Lys Glu Ala Ala Gln Arg Val Leu Ser Gln
1430                1435                1440

Ile Asp Val Ala Gln Lys Lys Leu Gln Asp Val Ser Met Lys Phe
1445                1450                1455

Arg Leu Phe Gln Lys Pro Ala Asn Phe Glu Leu Arg Leu Gln Glu
1460                1465                1470

Ser Lys Met Ile Leu Asp Glu Val Lys Met His Leu Pro Ala Leu
1475                1480                1485

Glu Thr Lys Ser Val Glu Gln Glu Val Val Gln Ser Gln Leu Asn
1490                1495                1500

His Cys Val Asn Leu Tyr Lys Ser Leu Ser Glu Val Lys Ser Glu
1505                1510                1515

Val Glu Met Val Ile Lys Thr Gly Arg Gln Ile Val Gln Lys Lys
1520                1525                1530

Gln Thr Glu Asn Pro Lys Glu Leu Asp Glu Arg Val Thr Ala Leu
1535                1540                1545

Lys Leu His Tyr Asn Glu Leu Gly Ala Lys Val Thr Glu Arg Lys
1550                1555                1560

Gln Gln Leu Glu Lys Cys Leu Lys Leu Ser Arg Lys Met Arg Lys
1565                1570                1575

Glu Met Asn Val Leu Thr Glu Trp Leu Ala Ala Thr Asp Met Glu
1580                1585                1590

Leu Thr Lys Arg Ser Ala Val Glu Gly Met Pro Ser Asn Leu Asp
```

```
            1595                1600                1605

Ser Glu Val Ala Trp Gly Lys Ala Thr Gln Lys Glu Ile Glu Lys
    1610                1615                1620

Gln Lys Val His Leu Lys Ser Ile Thr Glu Val Gly Glu Ala Leu
    1625                1630                1635

Lys Thr Val Leu Gly Lys Lys Glu Thr Leu Val Glu Asp Lys Leu
    1640                1645                1650

Ser Leu Leu Asn Ser Asn Trp Ile Ala Val Thr Ser Arg Ala Glu
    1655                1660                1665

Glu Trp Leu Asn Leu Leu Glu Tyr Gln Lys His Met Glu Thr
    1670                1675                1680

Phe Asp Gln Asn Val Asp His Ile Thr Lys Trp Ile Ile Gln Ala
    1685                1690                1695

Asp Thr Leu Leu Asp Glu Ser Glu Lys Lys Lys Pro Gln Gln Lys
    1700                1705                1710

Glu Asp Val Leu Lys Arg Leu Lys Ala Glu Leu Asn Asp Ile Arg
    1715                1720                1725

Pro Lys Val Asp Ser Thr Arg Asp Gln Ala Ala Asn Leu Met Ala
    1730                1735                1740

Asn Arg Gly Asp His Cys Arg Lys Leu Val Glu Pro Gln Ile Ser
    1745                1750                1755

Glu Leu Asn His Arg Phe Ala Ala Ile Ser His Arg Ile Lys Thr
    1760                1765                1770

Gly Lys Ala Ser Ile Pro Leu Lys Glu Leu Glu Gln Phe Asn Ser
    1775                1780                1785

Asp Ile Gln Lys Leu Leu Glu Pro Leu Glu Ala Glu Ile Gln Gln
    1790                1795                1800

Gly Val Asn Leu Lys Glu Glu Asp Phe Asn Lys Asp Met Asn Glu
    1805                1810                1815

Asp Asn Glu Gly Thr Val Lys Glu Leu Leu Gln Arg Gly Asp Asn
    1820                1825                1830

Leu Gln Gln Arg Ile Thr Asp Glu Arg Lys Arg Glu Glu Ile Lys
    1835                1840                1845

Ile Lys Gln Gln Leu Leu Gln Thr Lys His Asn Ala Leu Lys Asp
    1850                1855                1860

Leu Arg Ser Gln Arg Arg Lys Lys Ala Leu Glu Ile Ser His Gln
    1865                1870                1875

Trp Tyr Gln Tyr Lys Arg Gln Ala Asp Asp Leu Leu Lys Cys Leu
    1880                1885                1890

Asp Asp Ile Glu Lys Lys Leu Ala Ser Leu Pro Glu Pro Arg Asp
    1895                1900                1905

Glu Arg Lys Ile Lys Glu Ile Asp Arg Glu Leu Gln Lys Lys Lys
    1910                1915                1920

Glu Glu Leu Asn Ala Val Arg Arg Gln Ala Glu Gly Leu Ser Glu
    1925                1930                1935

Asp Gly Ala Ala Met Ala Val Glu Pro Thr Gln Ile Gln Leu Ser
    1940                1945                1950

Lys Arg Trp Arg Glu Ile Glu Ser Lys Phe Ala Gln Phe Arg Arg
    1955                1960                1965

Leu Asn Phe Ala Gln Ile His Thr Val Arg Glu Glu Thr Met Met
    1970                1975                1980

Val Met Thr Glu Asp Met Pro Leu Glu Ile Ser Tyr Val Pro Ser
    1985                1990                1995
```

-continued

Thr Tyr Leu Thr Glu Ile Thr His Val Ser Gln Ala Leu Leu Glu
2000              2005              2010

Val Glu Gln Leu Leu Asn Ala Pro Asp Leu Cys Ala Lys Asp Phe
2015              2020              2025

Glu Asp Leu Phe Lys Gln Glu Glu Ser Leu Lys Asn Ile Lys Asp
2030              2035              2040

Ser Leu Gln Gln Ser Ser Gly Arg Ile Asp Ile Ile His Ser Lys
2045              2050              2055

Lys Thr Ala Ala Leu Gln Ser Ala Thr Pro Val Glu Arg Val Lys
2060              2065              2070

Leu Gln Glu Ala Leu Ser Gln Leu Asp Phe Gln Trp Glu Lys Val
2075              2080              2085

Asn Lys Met Tyr Lys Asp Arg Gln Gly Arg Phe Asp Arg Ser Val
2090              2095              2100

Glu Lys Trp Arg Arg Phe His Tyr Asp Ile Lys Ile Phe Asn Gln
2105              2110              2115

Trp Leu Thr Glu Ala Glu Gln Phe Leu Arg Lys Thr Gln Ile Pro
2120              2125              2130

Glu Asn Trp Glu His Ala Lys Tyr Lys Trp Tyr Leu Lys Glu Leu
2135              2140              2145

Gln Asp Gly Ile Gly Gln Arg Gln Thr Val Val Arg Thr Leu Asn
2150              2155              2160

Ala Thr Gly Glu Glu Ile Ile Gln Gln Ser Ser Lys Thr Asp Ala
2165              2170              2175

Ser Ile Leu Gln Glu Lys Leu Gly Ser Leu Asn Leu Arg Trp Gln
2180              2185              2190

Glu Val Cys Lys Gln Leu Ser Asp Arg Lys Lys Arg Leu Glu Glu
2195              2200              2205

Gln Lys Asn Ile Leu Ser Glu Phe Gln Arg Asp Leu Asn Glu Phe
2210              2215              2220

Val Leu Trp Leu Glu Glu Ala Asp Asn Ile Ala Ser Ile Pro Leu
2225              2230              2235

Glu Pro Gly Lys Glu Gln Gln Leu Lys Glu Lys Leu Glu Gln Val
2240              2245              2250

Lys Leu Leu Val Glu Glu Leu Pro Leu Arg Gln Gly Ile Leu Lys
2255              2260              2265

Gln Leu Asn Glu Thr Gly Gly Pro Val Leu Val Ser Ala Pro Ile
2270              2275              2280

Ser Pro Glu Glu Gln Asp Lys Leu Glu Asn Lys Leu Lys Gln Thr
2285              2290              2295

Asn Leu Gln Trp Ile Lys Val Ser Arg Ala Leu Pro Glu Lys Gln
2300              2305              2310

Gly Glu Ile Glu Ala Gln Ile Lys Asp Leu Gly Gln Leu Glu Lys
2315              2320              2325

Lys Leu Glu Asp Leu Glu Glu Gln Leu Asn His Leu Leu Leu Trp
2330              2335              2340

Leu Ser Pro Ile Arg Asn Gln Leu Glu Ile Tyr Asn Gln Pro Asn
2345              2350              2355

Gln Glu Gly Pro Phe Asp Val Lys Glu Thr Glu Ile Ala Val Gln
2360              2365              2370

Ala Lys Gln Pro Asp Val Glu Glu Ile Leu Ser Lys Gly Gln His
2375              2380              2385

-continued

Leu Tyr Lys Glu Lys Pro Ala Thr Gln Pro Val Lys Arg Lys Leu
     2390                2395                2400

Glu Asp Leu Ser Ser Glu Trp Lys Ala Val Asn Arg Leu Leu Gln
     2405                2410                2415

Glu Leu Arg Ala Lys Gln Pro Asp Leu Ala Pro Gly Leu Thr Thr
     2420                2425                2430

Ile Gly Ala Ser Pro Thr Gln Thr Val Thr Leu Val Thr Gln Pro
     2435                2440                2445

Val Val Thr Lys Glu Thr Ala Ile Ser Lys Leu Glu Met Pro Ser
     2450                2455                2460

Ser Leu Met Leu Glu Val Pro Ala Leu Ala Asp Phe Asn Arg Ala
     2465                2470                2475

Trp Thr Glu Leu Thr Asp Trp Leu Ser Leu Leu Asp Gln Val Ile
     2480                2485                2490

Lys Ser Gln Arg Val Met Val Gly Asp Leu Glu Asp Ile Asn Glu
     2495                2500                2505

Met Ile Ile Lys Gln Lys Ala Thr Met Gln Asp Leu Glu Gln Arg
     2510                2515                2520

Arg Pro Gln Leu Glu Glu Leu Ile Thr Ala Ala Gln Asn Leu Lys
     2525                2530                2535

Asn Lys Thr Ser Asn Gln Glu Ala Arg Thr Ile Ile Thr Asp Arg
     2540                2545                2550

Ile Glu Arg Ile Gln Asn Gln Trp Asp Glu Val Gln Glu His Leu
     2555                2560                2565

Gln Asn Arg Arg Gln Gln Leu Asn Glu Met Leu Lys Asp Ser Thr
     2570                2575                2580

Gln Trp Leu Glu Ala Lys Glu Glu Ala Glu Gln Val Leu Gly Gln
     2585                2590                2595

Ala Arg Ala Lys Leu Glu Ser Trp Lys Glu Gly Pro Tyr Thr Val
     2600                2605                2610

Asp Ala Ile Gln Lys Lys Ile Thr Glu Thr Lys Gln Leu Ala Lys
     2615                2620                2625

Asp Leu Arg Gln Trp Gln Thr Asn Val Asp Val Ala Asn Asp Leu
     2630                2635                2640

Ala Leu Lys Leu Leu Arg Asp Tyr Ser Ala Asp Asp Thr Arg Lys
     2645                2650                2655

Val His Met Ile Thr Glu Asn Ile Asn Ala Ser Trp Arg Ser Ile
     2660                2665                2670

His Lys Arg Val Ser Glu Arg Glu Ala Ala Leu Glu Glu Thr His
     2675                2680                2685

Arg Leu Leu Gln Gln Phe Pro Leu Asp Leu Glu Lys Phe Leu Ala
     2690                2695                2700

Trp Leu Thr Glu Ala Glu Thr Thr Ala Asn Val Leu Gln Asp Ala
     2705                2710                2715

Thr Arg Lys Glu Arg Leu Leu Glu Asp Ser Lys Gly Val Lys Glu
     2720                2725                2730

Leu Met Lys Gln Trp Gln Asp Leu Gln Gly Glu Ile Glu Ala His
     2735                2740                2745

Thr Asp Val Tyr His Asn Leu Asp Glu Asn Ser Gln Lys Ile Leu
     2750                2755                2760

Arg Ser Leu Glu Gly Ser Asp Asp Ala Val Leu Leu Gln Arg Arg
     2765                2770                2775

Leu Asp Asn Met Asn Phe Lys Trp Ser Glu Leu Arg Lys Lys Ser

-continued

```
            2780                2785                2790
Leu Asn  Ile Arg Ser His  Leu Glu Ala Ser  Ser Asp Gln Trp  Lys
     2795                2800                2805

Arg Leu  His Leu Ser Leu  Gln Glu Leu Leu  Val Trp Leu Gln  Leu
     2810                2815                2820

Lys Asp  Asp Glu Leu Ser  Arg Gln Ala Pro  Ile Gly Gly Asp  Phe
     2825                2830                2835

Pro Ala  Val Gln Lys Gln  Asn Asp Val His  Arg Ala Phe Lys  Arg
     2840                2845                2850

Glu Leu  Lys Thr Lys Glu  Pro Val Ile Met  Ser Thr Leu Glu  Thr
     2855                2860                2865

Val Arg  Ile Phe Leu Thr  Glu Gln Pro Leu  Glu Gly Leu Glu  Lys
     2870                2875                2880

Leu Tyr  Gln Glu Pro Arg  Glu Leu Pro Pro  Glu Glu Arg Ala  Gln
     2885                2890                2895

Asn Val  Thr Arg Leu Leu  Arg Lys Gln Ala  Glu Glu Val Asn  Thr
     2900                2905                2910

Glu Trp  Glu Lys Leu Asn  Leu His Ser Ala  Asp Trp Gln Arg  Lys
     2915                2920                2925

Ile Asp  Glu Thr Leu Glu  Arg Leu Gln Glu  Leu Gln Glu Ala  Thr
     2930                2935                2940

Asp Glu  Leu Asp Leu Lys  Leu Arg Gln Ala  Glu Val Ile Lys  Gly
     2945                2950                2955

Ser Trp  Gln Pro Val Gly  Asp Leu Leu Ile  Asp Ser Leu Gln  Asp
     2960                2965                2970

His Leu  Glu Lys Val Lys  Ala Leu Arg Gly  Glu Ile Ala Pro  Leu
     2975                2980                2985

Lys Glu  Asn Val Ser His  Val Asn Asp Leu  Ala Arg Gln Leu  Thr
     2990                2995                3000

Thr Leu  Gly Ile Gln Leu  Ser Pro Tyr Asn  Leu Ser Thr Leu  Glu
     3005                3010                3015

Asp Leu  Asn Thr Arg Trp  Lys Leu Leu Gln  Val Ala Val Glu  Asp
     3020                3025                3030

Arg Val  Arg Gln Leu His  Glu Ala His Arg  Asp Phe Gly Pro  Ala
     3035                3040                3045

Ser Gln  His Phe Leu Ser  Thr Ser Val Gln  Gly Pro Trp Glu  Arg
     3050                3055                3060

Ala Ile  Ser Pro Asn Lys  Val Pro Tyr Tyr  Ile Asn His Glu  Thr
     3065                3070                3075

Gln Thr  Thr Cys Trp Asp  His Pro Lys Met  Thr Glu Leu Tyr  Gln
     3080                3085                3090

Ser Leu  Ala Asp Leu Asn  Asn Val Arg Phe  Ser Ala Tyr Arg  Thr
     3095                3100                3105

Ala Met  Lys Leu Arg Arg  Leu Gln Lys Ala  Leu Cys Leu Asp  Leu
     3110                3115                3120

Leu Ser  Leu Ser Ala Ala  Cys Asp Ala Leu  Asp Gln His Asn  Leu
     3125                3130                3135

Lys Gln  Asn Asp Gln Pro  Met Asp Ile Leu  Gln Ile Ile Asn  Cys
     3140                3145                3150

Leu Thr  Thr Ile Tyr Asp  Arg Leu Glu Gln  Glu His Asn Asn  Leu
     3155                3160                3165

Val Asn  Val Pro Leu Cys  Val Asp Met Cys  Leu Asn Trp Leu  Leu
     3170                3175                3180
```

-continued

```
Asn Val Tyr Asp Thr Gly Arg Thr Gly Arg Ile Arg Val Leu Ser
    3185                3190                3195
Phe Lys Thr Gly Ile Ile Ser Leu Cys Lys Ala His Leu Glu Asp
    3200                3205                3210
Lys Tyr Arg Tyr Leu Phe Lys Gln Val Ala Ser Ser Thr Gly Phe
    3215                3220                3225
Cys Asp Gln Arg Arg Leu Gly Leu Leu Leu His Asp Ser Ile Gln
    3230                3235                3240
Ile Pro Arg Gln Leu Gly Glu Val Ala Ser Phe Gly Gly Ser Asn
    3245                3250                3255
Ile Glu Pro Ser Val Arg Ser Cys Phe Gln Phe Ala Asn Asn Lys
    3260                3265                3270
Pro Glu Ile Glu Ala Ala Leu Phe Leu Asp Trp Met Arg Leu Glu
    3275                3280                3285
Pro Gln Ser Met Val Trp Leu Pro Val Leu His Arg Val Ala Ala
    3290                3295                3300
Ala Glu Thr Ala Lys His Gln Ala Lys Cys Asn Ile Cys Lys Glu
    3305                3310                3315
Cys Pro Ile Ile Gly Phe Arg Tyr Arg Ser Leu Lys His Phe Asn
    3320                3325                3330
Tyr Asp Ile Cys Gln Ser Cys Phe Phe Ser Gly Arg Val Ala Lys
    3335                3340                3345
Gly His Lys Met His Tyr Pro Met Val Glu Tyr Cys Thr Pro Thr
    3350                3355                3360
Thr Ser Gly Glu Asp Val Arg Asp Phe Ala Lys Val Leu Lys Asn
    3365                3370                3375
Lys Phe Arg Thr Lys Arg Tyr Phe Ala Lys His Pro Arg Met Gly
    3380                3385                3390
Tyr Leu Pro Val Gln Thr Val Leu Glu Gly Asp Asn Met Glu Thr
    3395                3400                3405
Pro Val Thr Leu Ile Asn Phe Trp Pro Val Asp Ser Ala Pro Ala
    3410                3415                3420
Ser Ser Pro Gln Leu Ser His Asp Asp Thr His Ser Arg Ile Glu
    3425                3430                3435
His Tyr Ala Ser Arg Leu Ala Glu Met Glu Asn Ser Asn Gly Ser
    3440                3445                3450
Tyr Leu Asn Asp Ser Ile Ser Pro Asn Glu Ser Ile Asp Asp Glu
    3455                3460                3465
His Leu Leu Ile Gln His Tyr Cys Gln Ser Leu Asn Gln Asp Ser
    3470                3475                3480
Pro Leu Ser Gln Pro Arg Ser Pro Ala Gln Ile Leu Ile Ser Leu
    3485                3490                3495
Glu Ser Glu Glu Arg Gly Glu Leu Glu Arg Ile Leu Ala Asp Leu
    3500                3505                3510
Glu Glu Glu Asn Arg Asn Leu Gln Ala Glu Tyr Asp Arg Leu Lys
    3515                3520                3525
Gln Gln His Glu His Lys Gly Leu Ser Pro Leu Pro Ser Pro Pro
    3530                3535                3540
Glu Met Met Pro Thr Ser Pro Gln Ser Pro Arg Asp Ala Glu Leu
    3545                3550                3555
Ile Ala Glu Ala Lys Leu Leu Arg Gln His Lys Gly Arg Leu Glu
    3560                3565                3570
```

```
Ala Arg Met Gln Ile Leu Glu Asp His Asn Lys Gln Leu Glu Ser
    3575                3580                3585

Gln Leu His Arg Leu Arg Gln Leu Leu Glu Gln Pro Gln Ala Glu
    3590                3595                3600

Ala Lys Val Asn Gly Thr Thr Val Ser Ser Pro Ser Thr Ser Leu
    3605                3610                3615

Gln Arg Ser Asp Ser Ser Gln Pro Met Leu Leu Arg Val Val Gly
    3620                3625                3630

Ser Gln Thr Ser Asp Ser Met Gly Glu Glu Asp Leu Leu Ser Pro
    3635                3640                3645

Pro Gln Asp Thr Ser Thr Gly Leu Glu Glu Val Met Glu Gln Leu
    3650                3655                3660

Asn Asn Ser Phe Pro Ser Ser Arg Gly Arg Asn Thr Pro Gly Lys
    3665                3670                3675

Pro Met Arg Glu Asp Thr Met
    3680                3685

<210> SEQ ID NO 3
<211> LENGTH: 400
<212> TYPE: DNA
<213> ORGANISM: Homo sapiens

<400> SEQUENCE: 3
tattacaaaa gagtcaagaa attaaaaaag caaaagttta taaataaaaa gttacagtaa     60
gctaaattta tttcattatt gaaaaaacaa aatgttttgc atatttagta tagcctaagt    120
gtacagtgtt cataaaatct ataggagtgt acaaaaatgt tctaggcctt cctatccatt    180
caccactcac tcactgacac atagagtaac ttctagttct ccaagctcta ctcatggtaa    240
gtgccttata caggtgtacc attttttaatc ttttatactt tatttttatt gtctattttc    300
tatggttaac tatggttaga taccattgtg ttagaatctc tgacagtatt cagtacaata    360
aaaacgataa ggtttgtagc ctagcagcca taggctatac                          400

<210> SEQ ID NO 4
<211> LENGTH: 1794
<212> TYPE: DNA
<213> ORGANISM: Homo sapiens

<400> SEQUENCE: 4 ttttttacaaa aaattaattt tcacaagcct caagacagac ttatgaatag atgaaacaga     60
atacggaaaa tatctgaaac aggaaggagt ccagcatttt agaagaaaaa atagaagtcc    120
attgtggctg aataaagta taagaggaa gagaggcaag agtttaagct ggagaggcta     180
gtagaagcca agaatacaac aaaaaaaaac acatggcatt tatctattct caatctctaa    240
aatagatatg ctaatcaccg aagacttttt atgtaaaata gcagtaattg atataccagt    300
attttcagag ttgtgtggaa tgatatgtat attattttag agaaatcttg gtggattcat    360
atggactcaa cttatctttc aggttttattt cttgcattta taaattatat ctaataaact    420
ataagttact gattgttgtg tatatcttga tatataggga ttatttgtgt ttgttataca    480
aaaatcaaat ggaagtagaa tagctaaaat gtatgagtac ttgcacacaa agcacacaca    540
cacacacaca cacacacaca ccataacccc ttaggaaaac actatttcag aatagcgata    600
ttggcatatt tcacatatgc taaatgagtt attccttata gtttcataat gtaactatga    660
aaccagctgt ctgtttactt tttgtggtag gggggatagc tttcctaaca aactaaatac    720
ctaatacaaa tctgagagga aacatatgat tttattaatt tttgtcatga aaacacttaa    780
```

```
actttcttgt gttataattt caaacaataa gtgcccccaa gacaggcaaa cttggaagtt      840
tagagaaaat tatacggtat aattgataac aattacagtt tcttttaaca aatactgatt      900
cacgattagt attttaaaa tacaaaatgc attttcctga atagcattta tttacttgtt       960
aaagaagttg tgtaacacat tcagctaatc taatttctta ctttgtgaag aaatcactca     1020
tctaaagtca aaatatcaag tataaagtct acccttggga gaagcataca gggtgccaga     1080 cttaaatat ctccagtgtg caaataaat aatattttct tgaaatatcc tcttatttga      1140
aaatttgcta tagagtcaca agaggcaaat tccatttgag aaagtgcatg ctatatttta     1200
caacgcagaa atgtggagct gagcacacaa catcttattg caaaagtaca attcagaaga     1260 gagttttac ccttaaaagg ctgtgaagat aagtaaaaat cagccaaaat ttcagtgtga      1320
ataatatgat gtttggcgag gaactctact attgttacac ttaggaaaat aatctaatcc     1380
aaaggctttg catctgtaca gaagagcgag tagatactga aagagatttg cagatccact     1440 gtttttagg caggaagaat gctcgttaaa tgcaaacgct gctctggctc atgtgtttgc      1500
tccgaggtat aggttttgtt cgactgacgt atcagatagt cagagtggtt accacaccga     1560
cgttgtagca gctgcataat aaatgactga agaatcatg ttaggcatgc ccacctaacc      1620
taacttgaat catgcgaaag gggagctgtt ggaattcaaa tagactttct ggttcccagc     1680
agtcggcagt aatagaatgc tttcaggaag atgacagaat caggagaaag atgctgtttt     1740
gcactatctt gatttgttac agcagccaac ttattggcat gatggagtga cagg           1794

<210> SEQ ID NO 5
<211> LENGTH: 1385
<212> TYPE: DNA
<213> ORGANISM: Homo sapiens

<400> SEQUENCE: 5
aagctttcta ttggcaaaga atgatttaca tgctgaatga cataatacaa ctgtattcac        60
ttaatacaga aaacaagcct ctattcagaa ccattaaatg atcattaact caatgtctaa       120
aaaaatggtg ttttaagaat tggcaccaga gaaatggaag aaagaataat ttgttagtaa       180
agaagtttta gcataattca caactgaaat ttaggatttg agaaaaattt ctttcctgca       240
ttataagagt attctttatt ttagcaggaa acatgtccc atgagaccta tacacacaca        300
cattctgcct tcagaattca gctgctgcat tctgctgctg cttctcttat tcagactgtt       360
ggcatcatca atacataact tttgattgaa tcccaaggga aaaaaataac tttggtagac       420
agtggataca taacaaatgc atggattatt ctgggcattc ctttttattt ggtagagtga       480 aattttggt gttgttgaga ggataaaaaa ggcatttaaa agtcaatttt gaatccggat        540
tttctgctct gttaataaat tcacatgaaa gttacagaaa gtattgttat gcttttgtac       600
tgaatagttt ttgtgtttag aaggctttaa aagcaagtac tatgtccact gtgctattct       660
ggtttggata ttaatcagaa cacagttgag cattgtttga attcacagag cttgccatgc       720
tggaagcaca accttatatg tagtgaccat ggacagtcct attatgggaa accaacttga       780
gagagaaggc gggtcacttg cttgtgcgca ggtcctggaa tttgaaatat ccgggggcct       840
ctacagaatc ctggcatcag ttactgtgtt gactcactca gtgttgggat cactcacttt       900 cccctacag gactcagatc tgggaggcaa ttaccttcgg agaaaacga ataggaaaaa        960 ctgaagtgtt acttttttta aagctgctga agtttgttgg tttctcattg ttttttaagcc     1020 tactggagca ataaagtttg aagaactttt accaggtttt tttatcgct gccttgatat      1080
```

```
acactttttca aaatgctttg gtgggaagaa gtagaggact gttgtaagta caaagtaact     1140
aaaaatatat tttactgtgg cataacgttt agtttgtgac aagctcacta attaggtaga     1200
ttgattttaa attatcacag tagttttgcaa agaagcataa atgttatata tactgcatat     1260
atatatgtat ttattcagga atatatattt ttcattggga aaacttttca acagaaatgg     1320
agtgtaaaag tttttctttg cgatagaact aaacacatga tttcttgatt aacaaaccac     1380
tgcag                                                                  1385

<210> SEQ ID NO 6
<211> LENGTH: 366
<212> TYPE: DNA
<213> ORGANISM: Homo sapiens

<400> SEQUENCE: 6
atgctgtctg tgaagctgaa tctgtgagaa cacctcacta ttcacggcaa ccggagtgga       60
agaaacaggt gcaaaaagat tgtgtgtttg tctgcttttg tgaggctggt cagagattct      120
gtgcctgctt tatctgtgct tggctatgac tctacctcca ggtttaccat accccataga      180
atgtgtaaga gaaaagtacc aacagggaaa tcagcaaaaa gctttcctat gaaggtgtgt      240
agccagcctc cgcagaattt gaaatgtctg aggtttcttc tggtgagtaa agctgcaga       300 taatcaacag ccattcagaa gaatgataaa tgccacaagc atttggaaac aggcttccct      360
aaaggt                                                                 366

<210> SEQ ID NO 7
<211> LENGTH: 761
<212> TYPE: DNA
<213> ORGANISM: Homo sapiens

<400> SEQUENCE: 7
aaacaatcta taattctaat ataatttact attaataata ataattatta tgtaaaataa       60
tagtgtgtgc cacggaagta accaaaatta ctgatcaata gtagctttat atggctgtag      120
atttagtcat ccacagatta tcttgctttg tccttttcaa aaggcagtta ataatcggat      180
ataatactct gagtgcaggt cttagataac tttaaaaatt atgctcttgg aatagaggga      240
aaaaacatct aaatgtggca aactgatgtg ttaaacattg ctaatccttt tgttttcaga      300
gtcaacataa cttatttctt tagagctatt tgccactttt accgagtgag taaaatacac      360
tcagtgacaa attttggagc aaatttgttt ctctctacct gatttctcta gaatttggaa      420
accatttgtg agtattctca atttatgaca gaatagtaa ttgcatatgt gcaataagaa       480
tctgttttct ttagtaacag gacaccattg gagaaattgg tcattttacc aaggctttga      540
ctggaatggc atgcttcctt taagaatca agttgactt atagagccat ttaaagcccg        600
ttggggaatc tggcctcata ccttgtccac acagagtccc tgtacaaggt tcctgacctg     660
tggtaagtaa agaatgtcac tttctaacag gcccaggaac cccaagttat cttgggacct     720
caagaggaga ggactttggt caactcatag gtatttgagg g                          761

<210> SEQ ID NO 8
<211> LENGTH: 322
<212> TYPE: DNA
<213> ORGANISM: Homo sapiens

<400> SEQUENCE: 8
atcaatgaat gtaatactaa atgtaaaaaa acactaacac atcataatgg aaagttactt       60
tggttgtaaa atatgaatta tatttaaagt tgcttcctaa ctttttatttt tttatttgc      120
```

```
attttagatg aaagagaaga tgttcaaaag aaaacattca caaaatgggt aaatgcacaa        180
ttttctaagg taagaatggt tgttactttt acttttaaga tctaagttgt gaaattttca        240
aaatggacta tgtacctgtg tatcttaaaa atccgtttta tttctctcat agtgtcattt        300
tattttagct gtgcaaatct gg                                                 322
```

<210> SEQ ID NO 9
<211> LENGTH: 523
<212> TYPE: DNA
<213> ORGANISM: Homo sapiens

<400> SEQUENCE: 9

```
ggtataaatc tcttactctt gctattcaaa ctaattcaaa tagacttgac ctatgataaa         60 attttaaat ttttttgtc atttgttctt tccttttttc atccatcatc ttcggcagat          120
taattatgct cactaattat ccttaaatat aggctttagt tttcaaaagg ggataatcgt        180
gaaaatgtat gcattggaag tgtgctttgt taaattgagt gtatttttt taatttcagt        240 ttgggaagca gcatattgag aacctcttca gtgacctaca ggatgggagg cgcctcctag       300
acctcctcga aggcctgaca gggcaaaaac tggtatgtga cttattttta agaaagttaa       360
ctttaaactt agtagaattt cagaccagaa actgacaaca tagttttatg acatctagta       420
gaatgactag gtactgattg aaacagcaat acctattcct tagtaaagca acctcgtatg       480
attttcattt ggcatactct accgcctgca gaaaaagtaa aaa                         523
```

<210> SEQ ID NO 10
<211> LENGTH: 327
<212> TYPE: DNA
<213> ORGANISM: Homo sapiens

<400> SEQUENCE: 10

```
aagcttaata gtgaaattat aaatggtttc atttctagta gattgtcggt ctctctgctg         60
gtcagtgaac actcttttgt tttgttctca gccaaaagaa aaaggatcca caagagttca        120
tgccctgaac aatgtcaaca aggcactgcg ggttttgcag aacaataatg taagtagtac        180
cctggacaag gtctggatgc tgtgacacac gatccttcat gtttgagtga gggctttggc        240
cccaaatgca gagaaagtat ttcaaattct cttgtaaatc agaccagttc ttactgagag        300
catatgttgt aattcgtgta tgcctga                                           327
```

<210> SEQ ID NO 11
<211> LENGTH: 408
<212> TYPE: DNA
<213> ORGANISM: Homo sapiens

<400> SEQUENCE: 11

```
gcttcaatgc taagtctctg aaaatagcta aatgcaatta ccttcacgtt tttattatta         60
ttattattgc aactaggcat ttggtctctt accttcaaat gttttacccc tttctttaac        120
aggttgattt agtgaatatt ggaagtactg acatcgtaga tggaaatcat aaactgactc        180
ttggtttgat ttggaatata atcctccact ggcaggtaag aatcctgatg aatggaaacc        240
aaaagggtaa cattaatctt gttttttaat ttttacccct gacgtgtgaa acaaatgtgt        300
atttctaaca ataacaaacc ctgctccata gtgctgcttt ttaaattgac actaccatgt        360
cgtctgaaat gttaaggatc atcacggtat aaaataggtc ctggtaca                    408
```

<210> SEQ ID NO 12

<211> LENGTH: 502
<212> TYPE: DNA
<213> ORGANISM: Homo sapiens

<400> SEQUENCE: 12

| | | | | | |
|---|---|---|---|---|---|
| ccaggagtaa | tagtgaacac | attcagtaaa | tggtatggca | tagataccaa | tgaatcagaa | 60 |
| tagactccta | gccttgagaa | gagacttaac | ttctggtaga | atctattatg | tctcattact | 120 |
| aattggccct | aaaatttcta | tttatcactg | aagatcaagg | acattcatat | ttaagtttgc | 180 |
| atggttcttg | ctcaaggaat | gcattttctt | atgaaaattt | atttccacat | gtaggtcaaa | 240 |
| aatgtaatga | aaaatatcat | ggctggattg | caacaaacca | acagtgaaaa | gattctcctg | 300 |
| agctgggtcc | gacaatcaac | tcgtaattat | ccacaggtta | atgtaatcaa | cttcaccacc | 360 |
| agctggtctg | atggcctggc | tttgaatgct | ctcatccata | gtcataggta | agaagattac | 420 |
| tgagacatta | aataacttgt | aaaagtggtg | atttagactc | tgatgacata | ttttccccca | 480 |
| gtatggttcc | agatccgttg | ac | | | | 502 |

<210> SEQ ID NO 13
<211> LENGTH: 449
<212> TYPE: DNA
<213> ORGANISM: Homo sapiens

<400> SEQUENCE: 13

| | | | | | |
|---|---|---|---|---|---|
| ttacttgttt | aaatagaaat | attttaaagg | gtaaatgaat | tacactcaag | acttaaggac | 60 |
| tatgggcatt | ggttgtcaat | gaaaattaag | catggaagta | atctcatgg | aacattctag | 120 |
| cattgattta | tatttgtctt | tgtgtatgtg | tgtatgtgta | tgtgttttag | gccagaccta | 180 |
| tttgactgga | atagtgtggt | ttgccagcag | tcagccacac | aacgactgga | acatgcattc | 240 |
| aacatcgcca | gatatcaatt | aggcatagag | aaactactcg | atcctgaagg | ttggtaaatt | 300 |
| tctggactac | cactgctttt | agtatggtag | agtttaatgt | tttcatctga | gacttgtcat | 360 |
| ttctacacaa | aatacaaaac | tacatatctt | aagttttcca | atactgtaga | tatatttaaa | 420 |
| atgttcagcc | ttcctgcact | atattatga | | | | 449 |

<210> SEQ ID NO 14
<211> LENGTH: 1249
<212> TYPE: DNA
<213> ORGANISM: Homo sapiens

<400> SEQUENCE: 14

| | | | | | |
|---|---|---|---|---|---|
| gttaacattt | ctagtactaa | tgacatactt | cacataaagg | attactttac | atcttggttc | 60 |
| actggaatga | gtgcagtaag | taaattttaa | tgccaagtag | caaatgaatc | ttttgaagga | 120 |
| gctgccactt | tatatgtgtt | attacaaagt | attattgact | ttaaatgctg | cgtttcattc | 180 |
| actttctgga | tgtggcaaag | gatatgaagt | cagatcaact | taatgtgcgg | gacttttaca | 240 |
| tttgtctcta | atgtctgaga | aggaaagtga | tattctactt | tatcccatgc | accacaatgt | 300 |
| aaacaaatat | ttttaacata | cacggaatag | taaaaatcat | tatatggtat | ttttctgttt | 360 |
| aatttatatt | gtggatacat | gactctcatt | tcagcagaga | cttatttagc | tctctgcata | 420 |
| ctttaatatc | agcaacattc | agttaaaagg | tatcaggttt | ctttactgag | aaccaaagcg | 480 |
| gtaaaccatt | ttgtgtattt | gtttaattac | cagtgcacca | tttgaattga | catgttaata | 540 |
| taactttcca | ttggagggaa | aatgtaatct | tttattttg | tttcttatct | aatgaaagct | 600 |
| actctgttag | atgggctagt | ttggcaattt | gacttaggaa | aaagtaatat | ggaatgaagt | 660 |
| ttttatatga | acaaggaaaa | taaattaact | ttactgctca | tctcattggt | ctgccaaatt | 720 |

-continued

```
ggaaagacat tttaggcctc attctcatgt tctaattagt ctctggagga cattcatgga      780
caattcactg ttcattaatc tatcgtcttc ctttaacttt gatttgttca ttatccttt       840 agagtctcaa atatagaaac caaaaattga tgtgtagtgt taatgtgctt acagatgttg      900
ataccaccta tccagataag aagtccatct taatgtacat cacatcactc ttccaagttt      960
tgcctcaaca agtgagcatt gaagccatcc aggaagtgga aatgttgcca aggccaccta     1020
aagtgactaa agaagaacat tttcagttac atcatcaaat gcactattct caacaggtaa     1080
agtgtgtaaa ggacagctac tattcaagat gttttctgtt ttatatgcat tttaggtat      1140 tacgtgcaca tatatatata acttatatgt atatacacgt gtatatatac aaagcctaat     1200
gtatgtatat gtacaaaaac agagacagac taaacctttt caattttgc                 1249
```

<210> SEQ ID NO 15
<211> LENGTH: 334
<212> TYPE: DNA
<213> ORGANISM: Homo sapiens

<400> SEQUENCE: 15

```
tatccactcc cccaaacccct tctctgcaga tcacggtcag tctagcacag ggatatgaga    60
gaacttcttc ccctaagcct cgattcaaga gctatgccta cacacaggct gcttatgtca    120
ccacctctga ccctacacgg agcccatttc cttcacaggt ctgtcaacat ttactctctg    180
ttgtacaaac cagagaactg cttccaagat aatctaacac tgcttttact tgcttgaatt    240
tttcagtgcc ttttatctcc tcgtgaagag ctggtttgtt tttcgaagtt ttattgattc    300
cctcatgtga ttctgctttg ttattgagtc ttct                                 334
```

<210> SEQ ID NO 16
<211> LENGTH: 645
<212> TYPE: DNA
<213> ORGANISM: Homo sapiens
<220> FEATURE:
<221> NAME/KEY: misc_feature
<222> LOCATION: (1)..(645)
<223> OTHER INFORMATION: n is unknown

<400> SEQUENCE: 16

```
tctagaagag ctttaataca atattaattt ggtgtggatt ttgaccgcta tttgaaaatt     60
gatgtatgca tgaggaagtt aaaatgaaaa ctccctattg tctgtatctg ctgttcctgt    120
gtttgataat gccagtggac agtcctagca ttttaaatat ttcattcgat tcatcattta    180
atgtactgga acaatctgca aagacattaa ttgtgtaaca cccaatttat tttattgtgc    240
agcatttgga agctcctgaa gacaagtcat tggcagttc attgatggag agtgaagtaa    300
acctggaccg ttatcaaaca gctttagaag aagtattatc gtggcttctt tctgctgagg    360
acacattgca agcacaagga gagatttcta tgatgtgga agtggtgaaa gaccagtttc     420
atactcatga ggtaaactaa aacgttaatt tacaaaacaa aacatatgac ttgttataat    480
ggcaagtcat cctttttcct caattactct ctcacatcct tgtatttttgg aaatttagtt    540 actatgatgt gcttgggatt ccaacagtca gattttgnnn ttttcttttg gagagcaacc    600
attgaaggca tttctacttg atcggccaac aggaatacga agccc                    645
```

<210> SEQ ID NO 17
<211> LENGTH: 525
<212> TYPE: DNA
<213> ORGANISM: Homo sapiens

```
<400> SEQUENCE: 17
tccgtccatc ttcaactcct tgcggaactt cctgggagct cttccttaat aaatcacttg    60
cactgaagtc cttatctcgg ggcctgcttc tgaagaactt gacttaagat aattttcctt   120
aattcatatt aaaagtggtt ttgggattct gcaaatacag gttaaattcc ttttactggg   180
aatataaatc taaatgggcc acaagtttaa aactgcaaac aaaataaaac tcaaaaacca   240
caccgattta cctagagttc taattacacc tgttaacttc cttctttgtc aggggtacat   300
gatggatttg acagcccatc agggccgggt tggtaatatt ctacaattgg gaagtaagct   360
gattggaaca ggaaaattat cagaagatga agaaactgaa gtacaagagc agatgaatct   420
cctaaattca agatgggaat gcctcagggt agctagcatg gaaaaacaaa gcaagtaagt   480
ccttatttgt ttttaattaa gaagactaac aagttttgga agctt              525

<210> SEQ ID NO 18
<211> LENGTH: 812
<212> TYPE: DNA
<213> ORGANISM: Homo sapiens

<400> SEQUENCE: 18
tgagaaataa tagttccggg gtgactgata gtgggcttta cttacatcct tctcaatgtc    60
caatagatgc ccccaaatgc gaacattcca tatattataa attctattgt tttacattgt   120
gatgttcagt aataagttgc tttcaaagag gtcataatag gcttctttca aattttcagt   180
ttacatagag ttttaatgga tctccagaat cagaaactga agagttgaa tgactggcta   240 acaaaaacag aagaaagaac aaggaaaatg gaggaagagc ctcttggacc tgatcttgaa   300
gacctaaaac gccaagtaca caacataag gtaggtgtat cttatgttgc gtgctttcta   360
ctagaaagca aactctgtgt atagtaccta tacacagtaa cacagatgac atggttgatg   420
ggagagaatt aaaacttaaa gtcagccata ttttaaaaat tattttttacc taattgtttt   480 tgcaatcttt gttgccaatg gccttgaata agtcccctcc aaaattcagg tgattgtatt   540
aggagatgga atatttaagg gtgaataatc catcagggct cctcccttaa gaataggatc   600
aagtcccata taaaagaggc ttcacacagt gttctcctat ctcttgaccc tccaccatgc   660
accaccatgt gaaaactctg tgaaaaggcc ctcaccagat gctaacatct tgatcttgga   720
tttcccaaac tcgagaactg tgaaaaaata aaggtacatt cttcctaaat tacctcattc   780
tcatttaaac acacaaagtg cacacatagc tg                              812

<210> SEQ ID NO 19
<211> LENGTH: 605
<212> TYPE: DNA
<213> ORGANISM: Homo sapiens
<220> FEATURE:
<221> NAME/KEY: misc_feature
<222> LOCATION: (1)..(605)
<223> OTHER INFORMATION: n is unknown

<400> SEQUENCE: 19
aaatggccag aagtgctgat agttgtagga aaanggtcct ttnaagggaa naagggnntg    60
ggatgagaag gagaacatcc tgctgtacct ttcttaacat ttgtcttctc tagatacttt   120
ccagttaaat taacaataga acatataaat ttgctgagcg tcatagcaga aaattggctt   180
ggaatggttt taggttaata aaaaatggga gtacctgaga tgtagcagaa ataaatttca   240
ccatttgaga gcaaatcatt tcaacacaca tgtaagaata tcattttaat ttcctttaaa   300
acattttatc tttcaggtgc ttcaagaaga tctagaacaa gaacaagtca gggtcaattc   360
```

```
tctcactcac atggtggtgg tagttgatga atctagtgga gatcacgcaa ctgctgcttt       420
ggaagaacaa cttaaggtca gattattttg cttagtaaac taaatatgtc ctttaaaaga       480
actataactt gaaaagtatt ttaaaaattt agaatgcaat ttatatatta aaatacttag       540
aatacaatat gtgtacaata tacacacact cataatcagc tgaagtgctg tgatttaaag       600
aattc                                                                  605

<210> SEQ ID NO 20
<211> LENGTH: 726
<212> TYPE: DNA
<213> ORGANISM: Homo sapiens
<220> FEATURE:
<221> NAME/KEY: misc_feature
<222> LOCATION: (1)..(726)
<223> OTHER INFORMATION: n is unknown

<400> SEQUENCE: 20
tggagccatt tatawwagtg gtataataac cacttcataa tgcttgtctc tttgcttttc        60
tatgaaaggt acaagacttg gtgagataaa gacaaatgac agtcacacca cttatttaaa      120
tgtaagcaga tcagaaagag tgtccctnnn aacttctagc gtacatagga gactgagata      180
ctttggcaaa ttattcatgc cattttttaat aaaacgtagt taccaattgt ttgctgatcn     240
gtgcttgatt gtctcttctc caggtattgg gagatcgatg gcaaacatc tgtagatgga      300 cagaagaccg ctgggttctt ttacaagaca tccttctcaa atggcaacgt cttactgaag     360
aacaggtgtg tcatgtgtga gaaactagct gtaaaagaca cgggggata ttaaattgga      420 aaagtaaaga tttatgttta tttattcctt ggaattcttt aatgtcttgc agtgcctttt     480
tagtgcatgg ctttcagaaa aagaagatgc agtgaacaag attcacacaa ctggctttaa    540
agatcaaaat gaaatgttat caagtcttca aaaactggcc gtatgtactt tctagctttc    600
aatggtctta taaaaaccca gtactgtata ttatcactat tatttagtct ctcctatgct   660
attgaatatt aaatgtttat ttttgcttgg atcatagatt attcaaagat gttatattgc   720
tacttt                                                               726

<210> SEQ ID NO 21
<211> LENGTH: 454
<212> TYPE: DNA
<213> ORGANISM: Homo sapiens

<400> SEQUENCE: 21
attggaataa ttagatagat tataacgttt cgtaccgtcg tattttcgt gaacgttttg        60 atcctttctg ggcacgattg aaatattttc ttatctatgc aaatgagcaa atacacgcaa      120
aagcagattg aactatagtg gtgtatggaa tgcaacccag gcttattctg tgatcttct       180 tgttttaaca ggttttaaaa gcggatctag aaaagaaaaa gcaatccatg gcaaactgt       240 attcactcaa acaagatctt cttttcaacac tgaagaataa gtcagtgacc cagaagacgg    300
aagcatggct ggataacttt gcccggtgtt gggataattt agtccaaaaa cttgaaaaga    360
gtacagcaca ggttagtgat accaattatc atgctacaga ctatctcaga gatttttaa    420 acctgcatta agagagtgac attataaccc taca                                454

<210> SEQ ID NO 22
<211> LENGTH: 1926
<212> TYPE: DNA
<213> ORGANISM: Homo sapiens
```

<400> SEQUENCE: 22

```
taaattgact ttcgatgttg agattacttt cccttgctat ttcagtgaac caaacttaag      60
tcagataaaa caattttatt tggcttcaat atggtgctat tttgatctga aggtcaatct     120
accaacaagc aagaacagtt tctcattatt ttcctttgcc actccaagca gtctttactg     180
aagtctttcg agcaatgtct gacctctgtt tcaatacttc tcacagattt cacaggctgt     240
caccaccact cagccatcac taacacagac aactgtaatg aaacagtaa ctacggtgac      300
cacaagggaa cagatcctgg taaagcatgc tcaagaggaa cttccaccac cacctcccca     360
aaagaagagg cagattactg tggattctga aattaggaaa aggtgagagc atctcaagct     420
tttatctgca aatgaagtgg agaaaactca tttacagcag ttttgttggt ggtgttttca     480
cttcagcaat atttccagaa tcctcgggta cctgtaatgt cagttaatgt agtgagaaaa     540
attatgaagt acattttaaa actttcacaa gaaatcacta tcgcaacaga aactaaatgc     600
ttaatggaaa tggtgttttc tggggtgaaa gaagaaacta tagaaactat aggtgataaa     660
ctactgtggt agcattttaa tcctaaaagt ttctttcttt cttttttttt tttcttcctt     720
ataaagggcc tgcttgttga gtccctagtt ttgcattaaa tgtctttttt ttccagtaac     780
ggaaagtgca ttttcatgaa gaagtacacc tataatagat gggatccatc ctggtagttt     840
acgagaacat gatgtctcag tctgcgcatc ctaaatcagg agtaattaca gaacacattt     900
cctgttcttt gatatttata aagtcttatc ttgaaggtgt tagaattttt aactgatctt     960
tttgtgacta ttcagaatta tgcatttttag ataagttagg tattatgtaa atcagtggat    1020
atattaaaat gatggcaata aaattttatg agtgcaaagc tggcataaaa attattttaa    1080
aaggtacaat ttccctttca ttccagttat tgtaattcta agattaagaa agaacgttaa    1140
aatctgccgt atgttttaa gcagcatatg tttagaaact catggaacac ttgacattag     1200
aatttgtgta taccagggta gagaagtttg aaaagaacac acatctaaaa ataccatgtc    1260
agatgttcta agaaaaaaaa taaatctaga gaagttattc aaatatatta tttgggatgt    1320
ttagtacttc tctattaact aatgactat gacctacttt gataattcca aagtaaatca     1380
ctgggccttt tctccctggt tgtgtcaact tggctaagca aatccactag tccagggtc     1440
accaaactaa gacctgctaa ccaaatttag catgctgcca gtttggtatg gctcatcacc    1500
aagaagtgtt tttgcgtttc aaatggttga aaataatcaa aagaaaaat aatattttat     1560
gacatgtcaa aattacataa aattcaaatt caaatttcag tgttataaat aatgttttag    1620
tggaacacag ccaaactcat ttatttatca cttatgatta ctttcgcatt acaacggcag    1680
agtttgaata gttgtaacac aaactgtata gtccacaaag cctaaaatat ttattaccta    1740
tcctatcaca gaaaagttt ggcgacccct gctccagtca aatggctctc aaactctatg     1800
aatattagca ttcttttgt ggcaacaact ttcaggacct tccaagcact ctactcacga     1860
tggatttaga aaatctaaca aaaattgatg gagtgaaaag cataatggca caaatccgtg    1920
aagctt                                                              1926
```

<210> SEQ ID NO 23
<211> LENGTH: 422
<212> TYPE: DNA
<213> ORGANISM: Homo sapiens

<400> SEQUENCE: 23

```
ttacattgag gtgaataaaa tgacctccgt gatcataaga ctctagatca aagctgactc      60
caaatttgag tctacctaac agggaaaata gtgctgctat taatactaat agaggtgtca     120
```

```
ggcaggagtc tcagattgag aaaagaatga taaatgtgga taaattgctt tttttaatat    180
agaagaaaga gataatcaag aaataatgac tattattttt tgctgtctta ggttggatgt    240
tgatataact gaacttcaca gctggattac tcgctcagaa gctgtgttgc agagtcctga    300
atttgcaatc tttcggaagg aaggcaactt ctcagactta aaagaaaaag tcaatgtagg    360
ttatgcatta attttatat ctgtactcat tttgtgctgc ttgtaaactc cgtgctttgt    420
ta                                                                  422
```

<210> SEQ ID NO 24
<211> LENGTH: 619
<212> TYPE: DNA
<213> ORGANISM: Homo sapiens
<400> SEQUENCE: 24

```
gcaagtcatg aaatggctca tgcttttatt gccattttga tgttttgat ggcaaaagtg     60 ttgagaaaaa gtctttagat tcacgtgata agctgacaga gtgaaacatc ttaaggcttg    120
aaagggcaag tagaagttat aattattgtg tagattcaca gtccttgtat tgaattactc    180
atctttgctc tcatgctgca ggccatagag cgagaaaaag ctgagaagtt cagaaaactg    240
caagatgcca gcagatcagc tcaggccctg gtggaacaga tggtgaatgg taattacacg    300
agttgattta gataatcttc ttagggattt gataaacaca taggttcata tttatcagct    360
gaattatatc agacaagcac ttgttaaata caaatttaaa ttaaaaggtg tttgtatgtt    420
ttttattatt ctttttttaa tgctaaggaa attattagga gaaattcaac tttgagttca    480
ttggaagaaa atgggatgtg gtagaatatt ttatcagtct gtagcagaga ataaatttt     540 aatgcaaatc tgctagaatt tatccaaata atttaagaaa taaggttaac agaaattgaa    600
acattaacag tcaagtata                                                619
```

<210> SEQ ID NO 25
<211> LENGTH: 457
<212> TYPE: DNA
<213> ORGANISM: Homo sapiens
<400> SEQUENCE: 25

```
tctgattcat attacacatt atatcttaga aaatattgat ctggtttgaa atcattcatg     60
tggtgaatac atttataatt aggatgtgtt ggctttcaga tcatttcttt cagtctgtgg    120
gttcagggga tatatttaat tatttttttc tttctagagg gtgttaatgc agatagcatc    180
aaacaagcct cagaacaact gaacagccgg tggatcgaat tctgccagtt gctaagtgag    240
agacttaact ggctggagta tcagaacaac atcatcgctt tctataatca gctacaacaa    300
ttggagcaga tgacaactac tgctgaaaac tggttgaaaa tccaacccac caccccatca    360
gagccaacag caattaaaag tcagttaaaa atttgtaagg taagaatctc ttctccttcc    420
atttggagca taatcaatag gtatttcttg gcattcc                             457
```

<210> SEQ ID NO 26
<211> LENGTH: 597
<212> TYPE: DNA
<213> ORGANISM: Homo sapiens
<400> SEQUENCE: 26

```
catacccatt aatgctctaa attatgtcat cttgaatttt aaatatcatt ataggatg      60 atacatattg aacaaagagc caaggtatcc ttaaatgtat ggctgtgata gaggcttgtc    120
```

```
tatactgtca tggatgtttc ttatcagata tttgtgaagg gtattaagct aaacttgcct    180
tactgctttt taataccttc ttttgcaaaa tgtaatgtat gcaaagtaaa cgtgttactt    240
actttccata ctctatggca caggatgaag tcaaccggct atcaggtctt caacctcaaa    300
ttgaacgatt aaaaattcaa agcatagccc tgaaagagaa aggacaagga cccatgttcc    360
tggatgcaga ctttgtggcc tttacaaatc attttaagca agtcttttct gatgtgcagg    420
ccagagagaa agagctacag acaagtaagt aaaaagccta aatggctaa cttgacattt     480 tccaaaatgg ttatttgtgg ggaaatccag aaggtactaa catgaaacaa taatttctgt    540
aaatggaacc attctcccta caacctgtat taacaaggaa cgaaatacta gaggtag       597
```

<210> SEQ ID NO 27
<211> LENGTH: 429
<212> TYPE: DNA
<213> ORGANISM: Homo sapiens

<400> SEQUENCE: 27

```
aaatatattt ttcagatttt ctaattttgt taatatttga aactagtaat ataattgagt     60
ttgctgacaa tttaggaaaa catggcaaag tgtgaaacaa ttaagtgatt ctcattcttt    120
tttccctttt gataaagttt ttgacacttt gccaccaatg cgctatcagg agaccatgag    180
tgccatcagg acatgggtcc agcagtcaga aaccaaactc tccatacctc aacttagtgt    240
caccgactat gaaatcatgg agcagagact cggggaattg caggtctgtg aatatttgaa    300
tgtcaaaaca ataaagcacg cttatcaagc attcacattg ataataacctt taaataatat    360 tagaatttaa gtcattctga caagtatggt agtttgccca ttgagcaaat gaaaatgaga    420
ctttacagt                                                             429
```

<210> SEQ ID NO 28
<211> LENGTH: 468
<212> TYPE: DNA
<213> ORGANISM: Homo sapiens

<400> SEQUENCE: 28

```
gaagtcataa ctgatagaag atcatctact ttgtttacat gtttgaatca tatagattca     60
agtcagttaa tttcactaaa actcatcaat tattattcat caattagggt aaatgtatt     120 aaaaaattgt ttttttaggct ttacaaagtt ctctgcaaga gcaacaaagt ggcctatact    180
atctcagcac cactgtgaaa gagatgtcga agaaagcgcc ctctgaaatt agccggaaat    240
atcaatcaga atttgaagaa attgagggac gctggaagaa gctctcctcc cagctggttg    300
agcattgtca aaagctagag gagcaaatga ataaactccg aaaaattcag gtaattcaag    360
attttacttt ctaccctcat ttttatttac ttgtttttttc cctaacgata cactgtaaac    420
tgtaaaggta cataagcatt tgaccttcag catctttcaa agttagtg                  468
```

<210> SEQ ID NO 29
<211> LENGTH: 482
<212> TYPE: DNA
<213> ORGANISM: Homo sapiens

<400> SEQUENCE: 29

```
gtaggatgtc tcgagagtac atcataaacc acatttggta gtaattttgt attttttaaca     60 atagcagact tcacacacca gtgctcatac agtagaccat aaaaatgcag tcttagtaaa    120
aatattcttt gcctmaagaa ctacttagag acatccttta aacatgggaa ttgttttggg    180
gcctgtgttt agacataaca caatgatgaa ttgtgttaaa agtaatcagc acaccagtaa    240
```

| | |
|---|---|
| tgccttataa cgggtctcgt ttcagaatca catacaaacc ctgaagaaat ggatggctga | 300 |
| agttgatgtt tttctgaagg aggaatggcc tgcccttggg gattcagaaa ttctaaaaaa | 360 |
| gcagctgaaa cagtgcagag taagattttt atatgatgcc tttaatatga ataattttgt | 420 |
| atgaatatta tttggttaga tcagtgtttt acagctgggg tggattttgc tctcctctcc | 480 |
| cc | 482 |

<210> SEQ ID NO 30
<211> LENGTH: 446
<212> TYPE: DNA
<213> ORGANISM: Homo sapiens

<400> SEQUENCE: 30

| | |
|---|---|
| aagactgtta ggcagtcatc tatatcaaat atctctgtat ctcaagatcc caaaagacaa | 60 |
| aaatccaata tgcaatgcca tcagtcccaa ttttacatt tctagctatg tttcatatct | 120 |
| atatgtggca gtaattttt tcagctggct taaattgatt tattttctta gcttttagtc | 180 |
| agtgatattc agacaattca gcccagtcta acagtgtca atgaaggtgg gcagaagata | 240 |
| aagaatgaag cagagccaga gtttgcttcg agacttgaga cagaactcaa agaacttaac | 300 |
| actcagtggg atcacatgtg ccaacaggta tagacaatct ctttcactgt ggcttgcctc | 360 |
| aacgtactta actaagattt cctaatgtct cccttcaccg ttactttgg ttaaggcttt | 420 |
| gttcctatgt ttttgcttta aagcac | 446 |

<210> SEQ ID NO 31
<211> LENGTH: 436
<212> TYPE: DNA
<213> ORGANISM: Homo sapiens

<400> SEQUENCE: 31

| | |
|---|---|
| ctcatgcata taagcttttt acttctttat cattactatc taagctttct attctttaca | 60 |
| tactgatgaa ataatataat aataatgttt catcactgtc aataatcgtg ttttgtttgt | 120 |
| ttgttttgtg gaaggtctat gccagaaagg aggccttgaa gggaggtttg gagaaaactg | 180 |
| taagcctcca gaaagatcta tcagagatgc acgaatggat gacacaagct gaagaagagt | 240 |
| atcttgagag agattttgaa tataaaactc cagatgaatt acagaaagca gttgaagaga | 300 |
| tgaaggtaaa aaaaaaaaa agaaaaacta agtaaaacaa aggaaataaa tggaaaaaga | 360 |
| aagaaatgca acaatgcttg aagttgtata cagtctgctc tttcctggtt ctaagagaag | 420 |
| aggttgattc ttcatt | 436 |

<210> SEQ ID NO 32
<211> LENGTH: 550
<212> TYPE: DNA
<213> ORGANISM: Homo sapiens

<400> SEQUENCE: 32

| | |
|---|---|
| ttgccttttc caaacaattg tatttatatc aatgtgtata tatttgacca cvaatccata | 60 |
| cctccatgca gactactttt cagtctattc ttgttacaga tctgttgtat tcttataata | 120 |
| aattatttct ttaactttcc aatttcaact aaacttaaat ttatggaaga gactggagtt | 180 |
| catattagat ttatttttgt aattctcatt ctaactggga tgttgtgaga aagaaattat | 240 |
| atgattcata gaaatgcatt ttggatgtaa agttattttc atgctattaa gagagcattc | 300 |
| tttatttttc agagagctaa agaagaggcc caacaaaaag aagcgaaagt gaaactccct | 360 |

```
actgagtctg taaatagtgt catagctcaa gctccacctg tagcacaaga ggccttaaaa    420
aaggaacttg aaactctaac caccaactac cagtggctct gcactaggct gaatgggaaa    480
tgcaagactt tggaagtcag ttgctttttct tggtctttgt caattatatg tcaatacatg    540
gtcatagtta                                                            550
```

```
<210> SEQ ID NO 33
<211> LENGTH: 275
<212> TYPE: DNA
<213> ORGANISM: Homo sapiens

<400> SEQUENCE: 33
gaagttttaa taatgaaatg gcaaaatttc acatttactt ttctaccata atatttaatc     60
tgtgatatat atttctttct taggaagttt gggcatgttg gcatgagtta ttgtcatact    120
tggagaaagc aaacaagtgg ctaaatgaag tagaatttaa acttaaaacc actgaaaaca    180
ttcctggcgg agctgaggaa atctctgagg tgctagatgt aagttgtaaa ttaagccaaa    240
tgatgatgat ttatatgcag tattaaaaga ggtac                               275
```

```
<210> SEQ ID NO 34
<211> LENGTH: 339
<212> TYPE: DNA
<213> ORGANISM: Homo sapiens
<220> FEATURE:
<221> NAME/KEY: misc_feature
<222> LOCATION: (1)..(339)
<223> OTHER INFORMATION: n is unknown

<400> SEQUENCE: 34
tttgctttaa gattatganc ttaatgatat gtaaatcaga agatactgag catttgctga     60
taatccaatg tatttagaaa aaaaaggaga aatngtaatt attgcaaatg tgtttcagtc    120
acttgaaaat ttgatgcgac attcagagga taacccaaat cagattcgca tattggcaca    180
gaccctaaca gatggcggag tcatggatga gctaatcaat gaggaacttg agacatttaa    240
ttctcgttgg agggaactac atgaagaggt attaagataa gtgaaaatct ctttaatcta    300
atttgcatta atgtatagca gatacagctc tcagatata                           339
```

```
<210> SEQ ID NO 35
<211> LENGTH: 557
<212> TYPE: DNA
<213> ORGANISM: Homo sapiens

<400> SEQUENCE: 35
gttcaagaga tcaggaggaa cattcgacct gagaaagaca gattgcaatg actgagatta     60
ttttgctaat ttttttttcca gcctatttcc ttaatgtacg tgatattgtg attgattttc    120
atgcagagat ccctgatcct atagttttgt ttgctattta ttttttctcct tcacattttt    180 tttctatcaa cagagctgaa tgagtgccag gaagctgcga atctgtcttt acaaaaaggt    240
gattgtggaa gagtctagaa tcttcattta ttgttcagca ggattacaga aaagctatca    300
agagtaaaca tttaactgat acactcttat tccttctttt taggctgtaa ggaggcaaaa    360
gttgcttgaa cagagcatcc agtctgccca ggagactgaa aaatccttac acttaatcca    420
ggagtccctc acattcattg acaagcagtt ggcagcttat attgcagaca aggtggacgc    480
agctcaaatg cctcaggaag cccaggcaag tacatctggg aatcagcttc cattctttttt    540 gtttgtatga cctcacg                                                    557
```

```
<210> SEQ ID NO 36
<211> LENGTH: 376
<212> TYPE: DNA
<213> ORGANISM: Homo sapiens

<400> SEQUENCE: 36
ttacagtgtg aaccaccact cttggccaat ttacggtcat tttaaaggaa gctacatggt      60
agaggtggtt gaggagagtt tctgaatttc gtcttcttgg aaagttagtt gttctttgta     120
gagcatgctg actaataatg ctatcctccc aacagaaaat ccaatctgat ttgacaagtc     180
atgagatcag tttagaagaa atgaagaaac ataatcaggg gaaggaggct gcccaaagag     240
tcctgtctca gattgatgtt gcacaggtat atgttatttc agaaactaag gaacgtgttt     300
tcgttgggca ttatactcca gtctatattg acaacttga ttattggcaa gattggattt      360
aggacattat ttgaaa                                                     376

<210> SEQ ID NO 37
<211> LENGTH: 439
<212> TYPE: DNA
<213> ORGANISM: Homo sapiens

<400> SEQUENCE: 37
tttttatttt tctgtatatc ttcagaaata aaggcaggat ctatcaataa aaataggacc      60
agttattgtt tgaaaggcaa aattaaatca gtgcctttt acactgtcct tacagaaaaa      120
attacaagat gtctccatga gtttcgatt attccagaaa ccagccaatt ttgagcagcg      180
tctacaagaa agtaagatga ttttagatga agtgaagatg cacttgcctg cattggaaac     240
aaagagtgtg gaacaggaag tagtacagtc acagctaaat cattgtgtgg tatgtatttc     300
tggtggcaaa tacgcaggtg ccccttgact ttcctcatta gaagtaact gctctttat       360 aagagagaat tgttttcaga taaccataat aattatacta tgtaatttta agattgagaa     420
caaaattgga cactgtatt                                                  439

<210> SEQ ID NO 38
<211> LENGTH: 531
<212> TYPE: DNA
<213> ORGANISM: Homo sapiens

<400> SEQUENCE: 38
atgacacata tatgcatgtg tgtagacatt agaatattaa atcaacagaa atgcaaaagc      60
tagatattga ccaccgctgc aaaatgctac tctattaaaa tttcaaacat ggaatagcaa     120
ttaagggatc tctatttatt tctgttcata atattatgaa ataatttaac tctactgatt     180
atcatgtttt gttttatgtt taaacttaga acttgtataa aagtctgagt gaagtgaagt     240
ctgaagtgga aatggtgata aagactggac gtcagattgt acagaaaaag cagacggaaa     300
atcccaaaga acttgatgaa agagtaacag ctttgaaatt gcattataat gagctgggag     360
caaaggtgtg tgcatgctga gaccacaaac acttcttttcc actttcctta taaattgtaa    420
agcaacgggc aataaattat gtatgattag agtcttagca attctaaaca cctctctctc     480
tctatgtata tgtatacgta tatatataca cacatatacg tatatatata t              531

<210> SEQ ID NO 39
<211> LENGTH: 426
<212> TYPE: DNA
<213> ORGANISM: Homo sapiens

<400> SEQUENCE: 39
```

```
aacgtgtaag aaaatagtta ttttaaataa cagaaatata aaagttccaa ataagtggtt    60
ataacgaaat ttgaattaaa gagtaaacta aattacattt cataataatt cttttcaggt   120
aacagaaaga aagcaacagt tggagaaatg cttgaaattg tcccgtaaga tgcgaaagga   180
aatgaatgtc ttgacagaat ggctggcagc tacagatatg gaattgacaa agagatcagc   240
agttgaagga atgcctagta atttggattc tgaagttgcc tggggaaagg taaaacctat   300
atcactgaag gttattttga acatacgtga aaacacataa tatgattttg taaggaagta   360
ttaacatgta gcaataatag catcataaat attaatattg tttcatattc cctttcttaa   420
aattaa                                                              426

<210> SEQ ID NO 40
<211> LENGTH: 363
<212> TYPE: DNA
<213> ORGANISM: Homo sapiens

<400> SEQUENCE: 40
aagcttcaat atatatggta tggtttcatg attcattaat acatagttat aggtttaaaa    60
ccttgcagaa tcatagtaac catacagaaa gccgtttcat aagcattaaa tcttaagact   120
acaagacatt acttgaaggt caatgctctc cttttcacag gctactcaaa agagattga   180 gaaacagaag gtgcacctga agagtatcac agaggtagga gaggccttga aaacagtttt   240
gggcaagaag gagacgttgg tggaagataa actcagtctt ctgaatagta actggatagc   300
tgtcacctcc cgagcagaag agtggttaaa tcttttgttg gtaagagaaa aggctagaag   360
ctt                                                                 363

<210> SEQ ID NO 41
<211> LENGTH: 662
<212> TYPE: DNA
<213> ORGANISM: Homo sapiens
<220> FEATURE:
<221> NAME/KEY: misc_feature
<222> LOCATION: (1)..(662)
<223> OTHER INFORMATION: n is unknown

<400> SEQUENCE: 41
aaaagataca taagtgacca gtaacaattc tgtgtttgaa aatttctcaa ttatacatat    60
atgctggctc ttaattcaat atctataaca atatttttaat atattttct ttatatttac   120 gcaatattct atatgaaaat accacttaaa actaatctca atgaaacttt attgttgtct   180
tttaaacatt ttagaacata ggaaaaattc tttaagaata ttgtctaacc aataatgcca   240
tggtatgtct ctgtacaatt aaggaatacc agaaacacat ggaaacttt gaccagaatg   300 tggaccacat cacaaagtgg atcattcagg ctgacacact tttggatgaa tcagagaaaa   360
agaaacccca gcaaaagaa gacgtgctta aggtagcaaa taaaatatga aaagtaatgt   420
ccaaattgta caccagttac ttcaatcatc tttgtcctaa aagatactaa ggacgtctta   480
ataagagtaa aacaatcctt ncttncttnc tttatctttc ccttttcct tccttcccc    540 tttgaatgga aatgaatcga ttttcgaaga gttctgtaat ctgactttct gttcaaatcc   600
atcactcagt taattatacc caatgtaaac tccgttcaga aagatattgg aagatttatt   660
tt                                                                  662

<210> SEQ ID NO 42
<211> LENGTH: 563
<212> TYPE: DNA
<213> ORGANISM: Homo sapiens
```

<400> SEQUENCE: 42

```
gacgtgatct attttctga aatcacacgc attttcattt tagtcctgtt ttatggaagt      60
tgtggtttta tctcccttg tatttctgc atgtgcttgc tctcattttc ttactttctc     120
tctctctctt tctcactctt ctcgctcact tgctcactcg ctctgtttgg ctctctttt     180
ctatcttgac cttcattaat tactaacttc aagtcctatc tcttgctcat ggaatatagc    240
gtttaaaggc agaactgaat gacatacgcc caaaggtgga ctctacacgt gaccaagcag    300
caaacttgat ggcaaaccgc ggtgaccact gcaggaaatt agtagagccc caaatctcag    360
agctcaacca tcgatttgca gccatttcac acagaattaa gactggaaag gtaggaagat    420
ctactccaag gtggaaactt gtgctaaatg gtctcttgcg aaggttgcgc agtactctga    480
aaggggcaa gtagacccca cagcaaggtt ttcaaagga aaatgaatgc caaatgtatt     540
taaggaaatt tacactgatt ata                                            563
```

<210> SEQ ID NO 43
<211> LENGTH: 260
<212> TYPE: DNA
<213> ORGANISM: Homo sapiens

<400> SEQUENCE: 43

```
aataaatgta tttcttttgg tttatgtttc ttataaaaag taattttgat ttaaagtagr     60
actaccttt tttttaggcc tccattcctt tgaaggaatt ggagcagttt aactcagata    120
tacaaaaatt gcttgaacca ctggaggctg aaattcagca gggggtgaat ctgaaagagg    180
aagacttcaa taaagatatg gtaaattggt tgtgaatgaa ctaggagtgg aaataaatat    240
ttggaaagaa cttagataag                                                260
```

<210> SEQ ID NO 44
<211> LENGTH: 404
<212> TYPE: DNA
<213> ORGANISM: Homo sapiens

<400> SEQUENCE: 44

```
ggattaaagt gtgtgtttaa ataacatgtc taattatctc tgttaacaat gtacagcttt     60
ttaaaaacca aaatgaagac tgtacttgtt gttttgatc agaatgaaga caatgagggt    120
actgtaaaag aattgttgca agaggagac aacttacaac aaagaatcac agatgagaga    180
aagcgagagg aaataaagat aaaacagcag ctgttacaga caaacataa tgctctcaag    240
gtattagagc taaaattata atataccttg cctgtggttt ttttttaata tagggtaa     300
tatataatgt gcattaataa aatctgcttc agactcttag tcatcagaaa ctcactttt    360
ctgttcaatg tgtatgctta tttaacatttt ttgaggtggt attt                    404
```

<210> SEQ ID NO 45
<211> LENGTH: 584
<212> TYPE: DNA
<213> ORGANISM: Homo sapiens
<220> FEATURE:
<221> NAME/KEY: misc_feature
<222> LOCATION: (1)..(584)
<223> OTHER INFORMATION: n is unknown

<400> SEQUENCE: 45

```
aacctaagtt gtacaaaaag atgagggacg caagttattt tgataaataa ctgcagccag     60
aagtgcacta tacatatata ttgatatttt aataatgtct gcaccatgaa caggatttga    120
```

```
ggtctcaaag aagaaaaaag gctctagaaa tttctcatca gtggtatcag tacaagaggc    180
aggctgatga tctcctgaaa tgcttggatg acattgaaaa aaaattagcc agcctacctg    240
agcccagaga tgaaggaaa ataaaggtaa tgttgtgttt tagaatgtca ataccagatt     300
ttattataca gtttaattaa cctgtgaaga tcatatttaa aatgttgatg ttcttgtttc    360
tattaacgtt ctctttgagt ttatgcattt ccttgtattg tgtgttgttt tcagtaaatg    420
tattgtatta agtgttattc aattgacgta atgttgaatg aataaaatgt tttagactat    480
gtaaaattga tttagaaatg tgatgtgttt tctggtaaat tgtaattgac tttgtgtatc    540
tttgtccaga ngaactaatg actaatcggg anaggcgcnc aacc                    584

<210> SEQ ID NO 46
<211> LENGTH: 298
<212> TYPE: DNA
<213> ORGANISM: Homo sapiens

<400> SEQUENCE: 46
atgtggttag ctaactgccc tgggccctgt attgttttgc tcaataggaa attgatcggg     60
aattgcagaa gaagaaagag gagctgaatg cagtgcgtag gcaagctgag ggcttgtctg    120
aggatggggc cgcaatggca gtggagccaa ctcagatcca gctcagcaag cgctggcggg    180
aaattgagag caaatttgct cagtttcgaa gactcaactt tgcacaaatt gtgagttgtt    240
actggcaaac ccacgtatgt gtttgcaact actactctat taacagaggc ctactaat     298

<210> SEQ ID NO 47
<211> LENGTH: 224
<212> TYPE: DNA
<213> ORGANISM: Homo sapiens

<400> SEQUENCE: 47
aattgttctt ttgtatatct ataccagcac actgtccgtg aagaaacgat gatggtgatg     60
actgaagaca tgcctttgga aatttcttat gtgccttcta cttatttgac tgaaatcact    120
catgtctcac aagccctatt agaagtggaa caacttctca atgctcctga cctctgtgct    180
aaggactttg aagatctctt taagcaagag gagtctctga aggt                    224

<210> SEQ ID NO 48
<211> LENGTH: 638
<212> TYPE: DNA
<213> ORGANISM: Homo sapiens
<220> FEATURE:
<221> NAME/KEY: misc_feature
<222> LOCATION: (1)..(638)
<223> OTHER INFORMATION: n is unknown

<400> SEQUENCE: 48
gagcctccma tgtgggtsyc ayystcttat ataagatatt tahaattatg agaacaaatg     60
ggatggatta tggacagaga agaaaagaag tgcaaatact gagtcagagc actcnaatat    120
taagatcagg atgagaagga tccagcaaag gaaagcagaa gaggtcagga tacagaagcc    180
aaatgaaggc agttttaaga tgtagggagc gatccactct ctcaggatga ggtctgtgat    240
ttacctattg aatttgaaca tgtcaaagtc actggacttc atggttatta actttaaaaa    300
gtcaataatt aagaattgca acaccatttg ctacctttgg gatttgtata tatatatata    360
tttttctctt tctatagaca gctaattcat tttttactg ttttaaaatt tttatattac     420
agaatataaa agatagtcta caacaaagct caggtcggat tgacattatt catagcaaga    480
agacagcagc attgcaaagt gcaacgcctg tggaaagggt gaagctacag gaagctctct    540
```

| | |
|---|---:|
| cccagcttga tttccaatgg gaaaaagtta acaaaatgta caaggaccga caagggtagg | 600 |
| taacacatat attttcttga tacttgcaga aatgattt | 638 |

<210> SEQ ID NO 49
<211> LENGTH: 15057
<212> TYPE: DNA
<213> ORGANISM: Homo sapiens

<400> SEQUENCE: 49

| | |
|---|---:|
| gaattcaggg tgaaagggggg atttgttgaa tttgatagag gatggcaatt accaatatga | 60 |
| tgagtgattg agaaacaagt ctgtgccaca ggtttgaaat cgaaaatctt tgaggtgtac | 120 |
| aggatcctga aatgaagaat gggcatttat agcagtatgt cagagaaaca gtcacctcct | 180 |
| agtagctaaa agtgttggca aaagtatagt tcaagtgatt gggtaggaaa aacagcaaac | 240 |
| caagagtgga gactgatggt tgctacaaag gtggagtgg aagtcgtgac caactggtac | 300 |
| ttctctgtgc tctggttagc tgctgactgt ttctcagact gtggtagcag gaggagggtt | 360 |
| ggagttagca gtcatttgca tatgagactg ccatttaaaa aaaaattta aattatttca | 420 |
| tttttctgac tctcaatatg aaaagcacat tgtagacaaa ttgaaaaata tagaaaaatt | 480 |
| atataagaaa atatagtctc accagtatgg aacaatgcta actatgttgc atagattttt | 540 |
| agattctcat tcaaaagcaa ctctttgact ccagtgatgc aaatgcatgt aacatatgca | 600 |
| atgtgcaatt catttttaaa gggaataaac ttacgatata ttcataggtc atttattgtg | 660 |
| tgttatatac cattgaaaat atatgaatgc taaattatta gtaaacatgc aaaaacattg | 720 |
| gcaagatcat tttgttgtgg aaggatatat tgtatctgaa taactctaga ataccataaa | 780 |
| tcatcaaagg caacattctt atttttcact aactacagtt agagaatacc tcttcggcta | 840 |
| ccttcggttg cctttttat gctaccaaaa tgctgtctgt tttacaagat tttaaaggtt | 900 |
| aagcatataa ttattcatta aatacaatga gtgcaatgta catgtagata cattattaaa | 960 |
| ttttgggtag ttaataaaaa taaggggaaa aaacctctag aactatcact tttaattgtt | 1020 |
| taactgataa agtgaagctt catccttggaa aaataaatttc acaagagagc atgtgcactg | 1080 |
| gtagaaaagt gccattgaaa caagagatat ttgggttaga agcctctctc tactatttaa | 1140 |
| taccatttc accttttggc aaattacttg gcctctgttt tctccaatgg aaaatgggaa | 1200 |
| taataattgt tatgctgcag ggttattgta ggtgtcaatg aaatgatgtg tctggcacta | 1260 |
| taaaagcaca gagcccggtg cctggctatt agtaactgtt taataaatgt taattccttt | 1320 |
| ctctgcccag gacatcagta ggcagatgta gcaatttaaa acttctagtg ttactttaaa | 1380 |
| ttcctgaatg aaggtagagg actgaaaaga tatcatggta ttcaaaagta tgatccattg | 1440 |
| cttcttaaga atagagttca gaaaagcttg acagattcct gtactctgag gcagcaccat | 1500 |
| agccggtaat ctgtaggatg gctattggtt ttgtgctcac aaatgcttgc ttggacaggc | 1560 |
| cccaggaaat ctggtagact gtaagcccag taagatttca aatcttactt tacggcagtg | 1620 |
| tttttcacct tgactgtaca ttgaaatcac ctggatgctt tgaaaaataa cagcgtcagt | 1680 |
| gtccaacctc cagaaatact gattaagttg gtctggaatg gagccccagg atcactgttt | 1740 |
| ggttattgtt gttgctgtgt tttaaatgcc ccagttgatt cttatgtgca actgtcttag | 1800 |
| gtaaacatac agccctggtt catattattt ctgcctcagt ctcttttatg actggaaggt | 1860 |
| gaccaaaatgc ttgttttccta atattctttc catgtgtagt attaacacat ttgacttgta | 1920 |
| ctaagttcct gcagtattcc aatctaaaat tttagtgact acaataaaat aagaaggatt | 1980 |

```
aaagaaggca tcgcatagtt tagtatatcg gttatttaat gcttacatgt gagcctacaa    2040
tatgaattat atctgtcatc ttatttttaaa tattgacaga atcttttaatg atagtgacga   2100 attattgatt tattggtgtg ataatggtat tttagttata tttttaaagt tttatttgta    2160
ataactatat gtatttatgg ggtacagtgt gacgtttcag tgtaatgttt cattgtgtaa    2220
tgatcaaatc aggtttcttg gcagatccat agcctcaaac atttataatt tctctgtggt    2280
gagaaaattt aaaattctct ttcactattt tgaaatatac agcacaatat tggtaacttt    2340
gttcatatta ctatgcaata gaacactaga acttattact cctttcagtt gatgaacagg    2400
cagttttgga tcaagaataa tattgaaagt gatagaattt atgaagtaat tttttatccaa   2460 aaatattttg aaagggaata tattgcttcc aaataattta ttacaatgtt aagatatttg    2520
taaatttcta gaattaaaaa aatatatttt taggaaagaa aatgccaata gtccaaaata    2580
gttgctttat ctttcttttta atcaataaat atattcattt taaagggaaa aattgcaacc   2640
ttccatttaa aatcagcttt tatattgagt attttttttaa aatgttgtgt gtacatgcta   2700
ggtgtgtata ttaattttta tttgttactt gaaactaaac tctgcaaatg caggaaacta    2760
tcagagtgat atctttgtca gtataaccaa aaaatatacg ctatatctct ataatctgtt    2820
ttacataatc catctatttt tcttgatcca tatgctttta cctgcaggcg atttgacaga    2880
tctgttgaga aatggcggcg ttttcattat gatataaaga tatttaatca gtggctaaca    2940
gaagctgaac agtttctcag aaagacacaa attcctgaga attgggaaca tgctaaatac    3000
aaatggtatc ttaaggtaag tctttgattt gttttttttcga aattgtattt atcttcagca   3060
catctggact ctttaacttc ttaaagatca ggttctgaag ggtgatggaa attactttttg   3120 actgttgttg tcatcattat attactagaa agaaaattat cataatgata atattagagc    3180
acggtgctat ggactttttg tgtcaggatg agagagtttg cctggacgga gctggtttat    3240
ctgataaact gcaaaatata attgaatctg tgacagaggg aagcatcgta acagcaaggt    3300
gttttgtggc tttggggcag tgtgtatttc ggctttatgt tggaaccttt ccagaaggag    3360
aacttgtggc atacttagct aaaatgaagt tgctagaaat atccatcatg ataaaattac    3420
agttctgttt tcctaaagac aattttgtag tgctgtagca atatttctat atattctatt    3480
gacaaaatgc cttctgaaat agtccagagg ccaaaacaat gcagagttaa ttgttggtac    3540
ttattgacat tttatggttt atgttaatag agaaacagca tatggatgat aaccagtgtg    3600
tagtttaatt tcaacttgtg gtgtcctttg aatatgcagg taagataga ttagattgtc     3660 caggatataa tttggttgct aaattacata gtttaggcat aagaaacact gtgtttatta    3720
cacgaagact taattattttt tgcatctttt ttagctcaaa ttgttcatgt tgcaatagtc   3780
aatcaagtgg atttgaattg tagccaattt ttaaggccag aaaatactga ttaagacaga    3840
tgagggcaaa aaacacccag tagtttatta aatactttag atatttcaaa atgctggatt    3900
cacaaaagca gtatcacatt tgactttaca agtcttcatt ctcaaatatg tttccatagt    3960
aaatatgccc tttaatatta aggagttaag catttaaaca cctatttata tgataagcta    4020
tttaaacaca gaaaatattt ttaaaacctt gtgtaattat atgtgtatca atcaaacttg    4080
catgcacacc agcgttggca tttgtataga gaggaaatgt atggattccc aatctgcttt    4140
aatatagaag atacattttta aaaatagcac tgaagtgaat tttgggctaa tgtagcataa   4200
tggggtttct gcctgagagg cagaaacata ttagagttat ataaaatgtt ttgggtaga     4260 tatagaaacc acttgccatt ttcaatgata tccaacccaa ggtagttata tatttcaatt    4320
tatattttat tatcaaatta gtacttattg tgaaaaaaat caagtaacat agaaatttgt    4380
```

```
aaaagtacct ccattctact ctttggagga tagttgttca gtatgaattt tgctacatat      4440
ttcaggctgg gtttcttgga aagccattgt aaaatggaga tttgtatgta gaaggttaac      4500
tagggagtac ttttacgatg aagcaatttg ttttgatgta acttggtgta gttttcttca      4560
tgtttcttgt tcttgaagtc agttaagctc ttgaatctgt gcatttaaca tttcatcaaa      4620
tttagaaacc tttcaaccat ttttttaaaa aaatggaac tccaattgta catttattag       4680
gctccttaaa gtgccccact actcactgat gttatgttca ttgtctgttt ggtctctctt      4740
ttctctgtaa tttgttttat ataatctcta ttgtcaaatt gactaatctt tttcaaagtc     4800
taatctatgg ctaatcccat gtagtatata tttttaacat cagacatttt catctcttag     4860
aagtaaaagt tgggtctttt tatttcttcc atgtgtctac tcaacatgtt cagtctttac    4920
tttcttgact atatggaata cagatataat aactgttaga atattcttct ctactaattt    4980
tatcatctgt gtctattctg ggttaattta aattgattta ttttttctcct cattaagtgt   5040 gttgtttaac tgcttctttg gatgactggt aatttttgac tatatgccag acattgtgaa    5100
ttttaactta gcgcgtgctt gatacttcaa ataaattcaa atatattgaa ataaatattc    5160
tcaaccctcg ttctggaaca cagttaattc acttggaaac aatttgatct tttgagaatc    5220 ttcctttttat gctttgttat gaccagaaca gtgtaagttt agggctactt tttcccccact  5280 actgaggcaa aacccttctg agtactctct ctgatgtcct gtgaatgata aaatttttca    5340
ctggggctcg tgggaacagg tggtattact agccacgtgt gagctctggt gattgtttcc   5400
tttaattctt ttgtgaagtt cttccttag ctttgagtgg ttttcttgca tacatgaact     5460
gatcaagact cagatgaaga ataaaataaa gctttctaca aatctccaaa atttcctctg    5520
tgtatatatc acctctctgg tattttgccc tgtgatcact agtcagcctt gggctgctga    5580
aactctcagc ttcatctttt aacagaagcc tcctggcaag gatcactgtc cttcaatgtc   5640
tgatgttcaa tgtgttgaaa accgttgtag catatatttt gtcttttttt ttttttttta    5700
agtgtttcag gtgtttcagg caggagatta agttcagcct cctttactcc aacttgaaaa   5760
caagtccaaa acaaactatt ttgatgtaat ttgatctttt aatacattaa cattacacaa    5820
ttttgtgaat atatcataat ttaaaatttt cagagaatgt ctaatggtcc tcatttcttg    5880
acagtgtggt ttagttgaaa ctgatgaaca ttttatcaaa acttttcccc tcaattggat    5940
actttttttt ttttgagatg gaattttgct tttgtcaccc aggctggagt ggcatgatct    6000
cagctcactg caacctctgc ctccaggctt caagcaattc tcctgcctta gcctcccgag   6060
tagctgggat tacaggtgcc cacccccaca cctggctaat ttttgtattt ttagtagaga   6120
cgagatttca ccatgttggt caggctggtc tagatctccg acctcaggtg gtctgcctgt   6180
ctcagcctcc caaagtgctg ggattgcaga cgtgagccac catgcctggc caactggata   6240
attttaaaaa gaccatttta tttagtctat tttttctcaa tctatagatg agataagaaa    6300
aatcattcta gatgtccaag gaaaaattct ttcagaaaag agctgtgaat gatatcacaa   6360
accccccaaa cagttaaggt atttctttcc tggttatttt atgtccaaaa tcatgcatat    6420
gaacatgtgc acacacatga gcgtgcacac acacatgaat acatatacac gcacataatg   6480
taccttaggt tatctttcca ttctgagtaa ttatcgtaaa atgggtaaaa tcaaccccgt    6540
aagatacctt catcgataag gcaaatcaaa gctttggtaa tttctgctat cttggccttt    6600
gttgattgac taataatgaa taagagaatg agtttcaata tttactatga aattatttta   6660
gaagacagga tgtagacagt ggctgttagc aggcaattgt ttggcatgag ccagtaatgg   6720
```

```
ttactgtgaa aaaaatcaac caagcagccc atatattaaa caaacacacg cagaagcacg    6780
ttggagtctg aagcctcata tgtacaattt tcagtaaaga aataactttt agatatgaaa    6840
taaacaaata gatatatgtt gtaaacttgt ccctatgtat tttgatcaaa ttgcatcata    6900 ttttttcac tttaaagaag agaatttagt gctttaactg agacttagtg ttatcattca    6960
aaatatactg actgccaata gcagcagaaa gataatctgg ttccatgcaa ctctattttt    7020
tttcctctgt cgcaagtaaa agacaaaatt aagtacatga attagtgctt tttgaagata    7080
ttccagagca ataccatg ccactatgga gaacctctct aaaaatatcc cattttttta    7140
cctgagaaaa atattgatca tgttatatgc cactcaaatt ggtttattaa attcgttgaa    7200
tgatatcagc atctcttaat gcattcacta acaagcagt aattgagtgc atatacaaag    7260
ttttatcatc caccaaaaca gtgacaatcc acatgaggct ctaatagaag tttagaaagg    7320
gggttaagtg gttaaatgct ggactcagaa agattggatt caaatcccag gtcctttagc    7380
ttaatagttg tagaatcttg tgaaaatatc ttaattcttt tcatgtctct gatttctctt    7440
ctctaaaatg gaaatataaa tgagatgtgt ataaagccac ttggaatagc attttgcaca    7500
aaataattac tcattaaatg taagcccta ttataactaa tcactctta taagtgatta    7560 gttcatatca atacaaacta agacttattt actgaattat cgtctctaaa catccacact    7620
gcagaaaaac caacctggaa atttcataaa accttatttt tatgtagtat aatttcttct    7680
caaagcataa gggctcttgg attaggaatt gaggaaaatt ccaattcagc caaacgcatc    7740
tgtttcagat agctgacact tctgcctact catttcctag ctaacaagaa gaaatgttaa    7800
tgggagtttt caaaggaaaa gctgaacacc atgaaggaaa gtgacacaaa taatgttagc    7860
tcatatattg acagggtgaa tttgtgtgct ttcaagtccc ttcagtgaaa ataggaaagt    7920
agaaattata aaatgcccta acatttaaag ctagcatgtt cttggagact aggaaaaaat    7980
aagttttaaa acatgggcta tgatagaatg agatggaaaa tgtttgtagt tgccagtaga    8040
aacaataaca attaccatta gattaagtat ttaaaccagc tgaatatttt tattaatgga    8100
aatggcatct gttttatgaa ataatgctgc tgaatgaacc atattaaaaa tgaccagtat    8160
ttcctgcaga acgttgtcgc agacatacaa gcctgagacc ctaaaatctt aaggtattcc    8220
atttgaaatc gaccttaaga cattaacagt agtggtattg tttagatgaa attttttagg    8280
ctttaaatca acaaatgtta agcagacatg gggagcgaaa caccagtgtg ttattctgac    8340
atgaataaac tgctgttttt agggaaaaaa tatagtcttg ttaaggttaa gctaattggt    8400
tttctggtat cttttgcaat gttagtgtgt tttactgctc cataacctat gttatatggt    8460
aaatgtgcaa tatatttcta tatgttgctg taaagaaatg taataaaaaa ctgtttactt    8520
tgtgatatga agtaaaaat ttattcattg tcattgagca tacagaagta aatatggatt    8580
acatatgtca tattttaatg ttcacatggt cccaccatca aatgttgaaa aacttatagt    8640
ttaacgtcat attctattga agaaaaatac actcccttt ctcaaatgtg aaatgtccag    8700
agagaatgga aaattacata taaagcatgt agttatagca tggtgaccct gctgtgatct    8760
ctcagatgag gaacaaaagg gagaaagaaa gagcacactg tgctttgga gttgagagaa    8820 ggcaaaaaaa gagtacaaaa atgtcaaagc caagtttagc tgctcttcag ctctcccttt    8880
agctgctctt cagctttacc ttaccatggt tattagtgat tgaagaaaat tctaaagcac    8940
tttttaaagg acccaattct gaagagttta gattcagaga gcacaatgga gttggagtga    9000
ctcctgctca aaagtttgag acaagcgagt ccatgaaaag accgtcctcc tcttaatgga    9060
aatacccagg tttcctcatt cttctcgcct tgctttcagc actcgcagcc cagaaagccc    9120
```

```
ttatctaaca ggtactgccg ttgaaaggtc attgacttgt acaaaaatga tgagtgctga   9180
atagatgtgc ataggtcact gacagtatct gctacagaga atgagttttc gtattcttat   9240
taggatacac ctaacatggc aatctactgc ctcaaagaac tctataggag gtaagtgaat   9300
ttatattaat acagattgaa ttaaaggata atctagaaaa aggcatatga tgtaaaaaaa   9360
tcagatacaa gtatattttc tgtatagtca gtttttacat tgtgatttca ccagctggct   9420
gctgagtttg acggcttctt aacagccaca ctgctgagat tcaaatgctg atagaaactt   9480
tgatggaaaa atcactggag taaatatttc taccatctgt tgccctgcac tgggaccta    9540
acgttaagaa taattcatac cattgcttgt cctttatatt tccccagcag taataaaatt   9600
tcataagatt ttgttttgtg gtcacaaagc tatcctggtt tctgtaacta aagacatac    9660
actagcataa gggaatcagc cggaaaattt actgctaaga gaatttgtct ctagtcactt   9720
actttaaggt tacagcaatg tgtaagtgtg ggaatacatt ttaaaatgag cttttcaaag   9780
ttattagctg gtagtggcat gagagttaag tctcttaata cagttaaaca gttgggcact   9840
tcatccttgc gtaaatattg ttacccttt attgctgctt ggaaactcct ctgcaacttt    9900
ttggccccta tccatctttt cagaagtagt aaataaccaa tttactggga gtgtggtacc   9960
aggcagaaat tccgagaggg gctttcaatc cttgcccatc aagtgtatct ttcagaaata  10020
agtatattaa aataattgga taatttcagt ggcttgttat tagacttccg ttgtccagca  10080
tggcatgttt aagaagatga cagattttca tacattattg gaaagaagca agaacaaaaa  10140
aacataactt actgtagtaa ccacggtaaa gaactgctta aaatgcagga taaacatgtc  10200
atccctaagg gattcccatt cttagagcat gaaattatca agagagtaag agactacaaa  10260
aaatgagaag aatgctgatt gcaaattcca aatagaaaaa atcaaaacaa aactgcgcac  10320
catcattctg gaagcaatga gaagcaggaa ttgtcattta atgaaatgta agattaaagt  10380
taatagaagt aattttcatg aaataatatt ttgcaaggac gatgttccag ccatattgat  10440
cttcgtgttt tcttttcaca tcccttctta ctgttcccta gaatgcttgt ttctaccttt  10500
aaatttgctt ttctctctac cagagggctc taccctatct ccagtttctc accatgtccc  10560
aatctactcc ctctcagaat ttttgtacac ttcccttat atatatttgt gctctaattt   10620
tatattcaca gatatgcctt ttgtaactcc cccatcttaa agaaagcaca cacgtacgca  10680
cacatgcaca cacacaaaat tgaactcttt ctgggagatc tgcttaactt tcttcataac  10740
tctgtcactt gctgaaactg tagtatgtgt tttcatgttt attatctttt ccattagaat  10800
gaacatattt tgggtacttg gtctttctcg atcaccaata tacctcggta cgtagaaaaa  10860
ttgattcata tattgaaaat gtaatattca gtagaacgaa taaatacata aataaattta  10920
aaaatgatac ttttattgta ttacctgaga caaatgatct ccaagtttgt ccttgctttt  10980
catagccaaa acattctctc ttacattgag cttccttcac ctcttctgtg tacagagcac  11040
ttaaaatttt cacattgtct gatactttaa caatatgatg gccctgttct cttacccatt  11100
ggagcatatg ttaaatacca gaacccatgt aacaaacata tattgtgatc ctactgtgtg  11160
caaagcagat actgcttgct gctaggaata cagagctgac taagagctcc ttttctcttt  11220
atgagctcac agtctcatga gttcaacgtc ttaaggcaca acgtctaaag caaagggcag  11280
taagtaaaca ctccagaaag tactggatct ggcctaggac aaatggtggg ttgttttttcc  11340
agctgttatt tttcctgccc cctaattgac agtcctccat tacacctctg ggatacctag  11400
tctgacttgg gaaaacctga ctttgggaat cagaggcagt ctctcttgct tatatatgag  11460
```

```
gaactctaat ggatacttac tgtcattaga gaaactctgc ttctagcctg gctccttttg   11520
taaagaaggt tgagtcccct tggagagcct gcagaacata accatttgca tgtaatgaac   11580
agtttgtaat actttgagat tgatgtgcaa tttctatttg acaagggaaa acaattagg    11640 attaaccgtg gtcgtatatc ccagaatacc aacgttgttt ccacactcta agtgttgttg   11700
ggtcattata tgagattcat aattttgtcc tgttgtaccc acgtttgcat taccattcag   11760
tcttaattta ttatacccta ttaaaagttt ttttggtaat ttgttcttat tgctactcag   11820
gcattaaaat gtctgcaggc tgtgaaaatg aataaattta atgtggcagc atagttctca   11880
aaatcctggc tttacaactc atagtacagg cttgtattgt aaatcctagt taacatggat   11940
ttatttgaaa atccaattt actgctaatc ttaaataaca cattttcaa acattttatc    12000 cttgaatttc tatttttta taattatgg ctgttgtatg tatttacaaa aggacaatgt    12060
gtgtactttt aaatactagt aatggattgc tgaaacaact gtaactttaa aacaatgcaa   12120
ttgttaaaaa aataaactgt gcagcctggc ttaatggagg cttatgaaca tatgattaag   12180
atatatgcta taataagcaa attcactcaa ctgatagttc ataggaactt tcaaatttaa   12240
tctcataacc agtgctatcc ttcaaagaat ggtcagggca atttaacgag tacatgacca   12300
cgcaagataa tttcattgaa gagtggctga actgttgaaa tattttctag tctccttggg   12360
atatcattaa gagcagaaat tttgaaatgg aattgtaatg atgttcagaa aagataagta   12420
ggtaactctc ttaatacgtt ttgtgctgct gtaacaaagt acctaaggct aggtaataat   12480
ttgtaatgaa caaaaatgta ttggctcaca gttctggaga ctaggaagtc taacattaag   12540
gtgtcagcct ctggcgaggg cctacttgat atgtcatcac atgatggacg attagagggc   12600
aagaaagatc aaaaggggc tgaactccca ctttttataag ggaaccaaac ccactcgtga   12660
gggtggagcc ctcaatcctt aatcacctcc taaagctccc acccctaat actgtcacaa   12720 tgccaattaa atttcaacat cagttttgga gggaaaaaaca ttgaaaccat agtagtgata   12780
ctgacgacta ccacacaggg cttgggaggc taccctagct gttgcaccca agagatgaat   12840
cttctaatgt gattaccttt atcatttttt ttactttatt aaaatacttt tattttacat   12900
gtatactttt gtctacccac catttccatg tctgaccact gctactacta tgtcctagca   12960
taacattcca tacatcctta aaaccaagca aagggtggag ttccatcttt aaaaactaaa   13020
caggcatttt ggacaacaca ttcttggcaa tggaatctgg acaacattta tcaaacatgg   13080
tagggaaggt tctcactctg cattatcaaa acgacagcca gatatcaact gttacagaaa   13140
cgaaatcaga tggaaaattt ttaacaaatt gtttaaacta ttttcttaga gagacttcct   13200
ccactgccag agatcttgaa tagcctctgg tcagtcatct ggaagcaatt cttcacataa   13260
ttcatgaact tggcttccac tttaggaaga gaaccaccct tttctatact tgcttgcatt   13320
tttgctttaa tgtcttctac agaactaggt cctttgggtg ttttaggagt ttttccttgt   13380
tttgaaggat tcttgtcctt ttgatcttgg tgttgacggt tttgagtctt ttccattccg   13440
atttgacttt tgtgcatttt tggctggagt atctcatata gatttcttca ctggcgcttt   13500
ttcttcagtt tcctcatcat caaaatcatc atcatcatca aaatcatcat cttcatcagc   13560
agcaagtttt actttttct gtggaacctt gctaccacct ccaggggcag atcgctttcc    13620
agatatactt atgagtttca catcctcctc ctgttcgtct tctgactctg tatcttcctc   13680
cccagctact aaatgctgtc cactcacatg cactggccct gaaccacact tcaaccgtaa   13740
gaccactgat ggtgttattt caaagccctc aagggaaacc atgggctgta cagacatttt   13800
caaagctgcc agtgttactt taattggact gcctttgtaa ctcattgcct ctgcttcaac   13860
```

```
aatgtgcaat ttatcctttg ccccagcccc taaactgacc gttcttaaag ataactgttg    13920
ctcaatttca ttattatcca ccttaaagtg atcatctttg tcggccttta gttcacaacc    13980
aaaaagatag ttttggggcc tcagaggact catgtccatc atcgtccatc aggtggcagg    14040
acgcacttag gtgggagaga gggcagatga tgataaagga ccactgctca agagaacagc    14100
tgtgcaggac agaatcacac cagggagatt acctttatct tagaaaacct gaacatcttg    14160
tgtactttga cacttctcta catttcacct aacctttaac atcaacacat ttattcagaa    14220
aacttttact tttggagctg ctctgtgtca ggctctatgc taggtgctca ggatattgaa    14280
attgatacaa tcctaaccta ttcacatata atccaaggtt tgctgaaatt gatggacatt    14340
taaacaattg aaacatttaa gtggtataat tagcaaatgg acatttaagc cataaaaata    14400
gcatctaata gatataatag aggtcggtac accattgatg agtcagagca gaggcaaccc    14460
aaagagtaac tagccagaag aattgggaaa gcttcataga gagagcgata tgaaaataag    14520
ggagagaatt gtaaatccat gaaaatgaga aaaagttgaa aagtgatggt gtcagaaaaa    14580
cttgtggtat gataatgaca agatgagagg aactctttgg taagctgtgt tggatgcatg    14640
gaaagaaatt ggcacaaaat aatgctgagg acatttttta ttttattgtt ggttttgttt    14700
tggttaattt cattttttaa atctagtatg ctagtgttca ttgtccaaac tgtgaatcat    14760
aaactcagtt tgtggatcaa caccggcctt tgatttttag tgaaacaaaa tagaaaatat    14820
cagcattcat cacaaataga tgtttcacag attttttgtt ttaattgcga ctgtgtgtgt    14880
gtgggtgtgt gtgtgtgtgt gtgtgtgtgt gtgtgtgtgt gtgtatgtga gagagagaga    14940
gagagagaga gagagagaga gagatggctt ggatgtttat cacctccgaa tcttatattg    15000
aaatgtgatt tccaatgttg gaggcagggc ctggtaggtg tgattggatc cgaattc       15057

<210> SEQ ID NO 50
<211> LENGTH: 3470
<212> TYPE: DNA
<213> ORGANISM: Homo sapiens

<400> SEQUENCE: 50
agccagctat gtgagcataa ggggtaggta gctttggtcc tccatgtcca aactgtttgt      60
agtggtaagt gatcttcatt ctcacataga ttgaaagctt cctgaggaca gggcaatgtc     120
tttgtaaact ttaaaatatc tatgtcctgc acatcacctg ccgtagacaa gcatctagta     180
attgacggtt gggtagatac tgagggaaaa catgcaccaa ataaaaatgg caataggaca     240
caaattcact atcatttgga agaataacag tgttttccac tgatatttgc tacacacagt     300
ggggtccaca gagcagcagt accacttggg agcttattgg aaatggagac tctcaggcac     360
caccgcaggt ccaatgaatt aaactctgct ttttttaagg tcatttgtat tcaattatta     420
tttttttctt ttttctttaa ctttcgatgc atttttcttt atttgttttt gagatggggt     480
cttgctattt tgccgagtct ggtcacaaac tcctgagctc aaatgatcct cccacctcag     540
cctcctaagt agctgggatc acagatgtga gccaccacac ctggcttgta tcacattaaa     600

ttttgaggag cagtgcttta atatctattc cattctcatc acttgatgag gtattattaa     660
ttccacttat ggatgtggaa gttgaagcca gaaagtttaa atgacttgta caaggtcaaa     720
cagcttacag gtagttgagc caagaggctc tcaagtcttc tgcctccaca acccctgtt     780 cagctgctgc cctacaatgg aataaaatat actaatccca gagggacaaa tatgctaaaa     840
atctcaatat tatacactt ggaaggtgca ggtgcattat ctttcaattc taatttctct     900
```

```
ttcaagtttt ctgatgcata aaaatatgaa cagcaggtct gagcaatgtt tagatgccgt      960
gctttgatcc tttttgccatt caagatgttt gatttgcatt ctgccaagga aatgtctggt   1020
aacctccatg atgcagacca caccattagt caagagagag ctgacgtacc ttcatctgag   1080
agctggctgg ctgtgagctg ctcagaggga aaggatttct atttacaaat tgtatcgatt   1140
atttataaat aaaagttccc cttgctttct tcagttgtaa atctgcagt tagagagtcg     1200
ggaagaagat caaaactgca tacatttgca tctgccaagc ctgataacta gttccagaat   1260
tacagaaatg gtgctgaaat agcacctcaa gtaccaggct ctatcaaatt taatctatcc   1320
ataaggcaac tgccaattat attttagaga aaaatgtta gactgaaaag atagacaatc    1380
caagtagcaa ctcctgtaaa attatatgcc cataggagca atcttgaaga tataaatatt   1440
ggtatgtttc tccttcattt atcatttatc tgatcatttg acaagtattt attgaatgcc   1500
tgttaagggt gtagatatat gtggtgaggc tgcaggtgta agtaggtctt tctgaggata   1560
tgcatgaagt tgatgttcat aacttggaga tgtgtgtata cagactgagg attccttcag   1620
tggatattaa gaagtggagt aataggcagt aaagaataca ctagtcagtt gtggtacata   1680
aacacgtcag caccacttag gtattaactt cctgttttgt tttgtgtgtg cttaattacg   1740
ctgtttatta aacaagcaca tcataatctg cagatattgt cataaacagc acaataaagc   1800
ctgccacatc agaatgtcat ctatcaaatt aggtgtgttc ctcagctgtc ccgataggca   1860
cacacctgtg cctgtaaata ggcgcttggg ggagattgct tccaggtgtg gatctgttgg   1920
gcgaccttgg gatgtagggc actttggaac cttttcctct agcttcagga attaaccctct 1980
gggcttggtt ccatgccagc ttgcattttg ctttgggaca gtaacatgta aagaatatgc   2040
ctgtgaattt agggttactg agaagtcctc atagaagaag taaaatttcc ttgaggaatg   2100
ggagtctttt attcaatcca ggtttaatgc aaggcttggt gaacagctcc agaaggttaa   2160
taattgcgtg cgtgtgtgtg tgtgtgtgtg tgtgtgtgtg tgtgtgtatc cttttgtcat   2220
tcaaaagtat acgtatacac acacacctgt acagctgatg ataaatatac attgtatcaa   2280
tgagttcaaa tgaagtgtgc tattcattca ctgaggaatg ggctattata atgaactatt   2340
atgatattag aaattgtcag ggcaataagc aaataataca tacggttttc aacaaacttt   2400
ctaagtattg ttatcagtgg gtttgcttaa atcttttttt acaaatttat ttattttttt   2460
gagacgaagt ctcgctctgt cgccaggctg gagtgcagtg gtgcaatctc ggctcactgc   2520
aaccactgcc tcccgggttc aaaagattct cctacctcag cctcccgagt agctgagatt   2580
acaggtgtgc gtcaccatgc ccatctaatt ttagtatttt tagtgagaga cgggttttca   2640
ccatgttggc caggacagac tcgatctctt gaccttgtga tccatctgcc tcagtctccc   2700
aaagtgctgg gtttacaggc gtgagccacc gcacccaggc aatagcccca ttgctcagtg   2760
aatgaatagc acactttatt ttaactcatt gatataatgt atatttatca tcagctatac   2820
aggtgtgtgt gtgtgtgtgt gtgtgtgtgt gtgtgtgtgt gtggtgttaa tgcacaaaag   2880
gatacacaca cacactctta ttaaccctct ggagctgttc agcaaacctt gcatttttta   2940
cttttcattac agtgtgtaaa taatttagca aattctaatt tgaacctgat atcaattgag  3000
catttaatat ttagccaaat atttatcaag tgctgactgt gttctagatg ctggggctgc   3060
aatttcgaaa cagaccattg aggccctcat ggagctcaca ataaatgatc ttccttaaag   3120
tatcaggtct ctggtttgtt accgtatttt ttaaattgtt aaggaaagaa aaaggcccta   3180
tcttttttgta gacaaacatg ccctaagtgc ttccagaaat aatctccatc aggtaatgca  3240
gactgtgtgt ggagtgaaat tgagtccaat ccatgatcca gcagagtttc agcccaggat   3300
```

| | |
|---|---|
| ttctttagag cctttgctac acacaaagtt ggctgatgtg ccattcagca tcccagcagc | 3360 |
| tctttctctt cacactagca atggcaaagc tttgtgcgga ggcattgctg gctgctctga | 3420 |
| actaaaagca tccgtgggga ccgaaagagg tttttgcaca ccttattaag | 3470 |

```
<210> SEQ ID NO 51
<211> LENGTH: 624
<212> TYPE: DNA
<213> ORGANISM: Homo sapiens

<400> SEQUENCE: 51
```

| | |
|---|---|
| acccaaatac tttgttcatg tttaaatttt acaacatttc atagactatt aaacatggaa | 60 |
| catccttgtg gggacaagaa atcgaatttg ctcttgaaaa ggtttccaac taattgattt | 120 |
| gtaggacatt ataacatcct ctagctgaca agcttacaaa aataaaaact ggagctaacc | 180 |
| gagaggtgct ttttccctg acacataaaa ggtgtctttc tgtcttgtat cctttggata | 240 |
| tgggcatgtc agtttcatag ggaaatttc acatggagct tttgtatttc tttctttgcc | 300 |
| agtacaactg catgtggtag cacactgttt aatcttttct caaataaaaa gacatggggc | 360 |
| ttcatttttg ttttgccttt tggtatctt acaggaactc caggatggca ttgggcagcg | 420 |
| gcaaactgtt gtcagaacat tgaatgcaac tggggaagaa ataattcagc aatcctcaaa | 480 |
| aacagatgcc agtattctac aggaaaaatt gggaagcctg aatctgcggt ggcaggaggt | 540 |
| ctgcaaacag ctgtcagaca gaaaaagag gtagggcgac agatctaata ggaatgaaaa | 600 |
| cattttagca gactttttaa gctt | 624 |

```
<210> SEQ ID NO 52
<211> LENGTH: 687
<212> TYPE: DNA
<213> ORGANISM: Homo sapiens
<220> FEATURE:
<221> NAME/KEY: misc_feature
<222> LOCATION: (1)..(687)
<223> OTHER INFORMATION: n is unknown

<400> SEQUENCE: 52
```

| | |
|---|---|
| atctctatca ttagagatct gaatatgaaa tacttgtcaa agtgaatgaa aatttnntaa | 60 |
| attatgtatg gttaacatct ttaaattgct tatttttaaa ttgccatgtt tgtgtcccag | 120 |
| tttgcattaa caaatagttt gagaactatg ttggaaaaaa aataacaat tttattcttc | 180 |
| tttctccagg ctagaagaac aaaagaatat cttgtcagaa tttcaaagag atttaaatga | 240 |
| atttgtttta tggttggagg aagcagataa cattgctagt atcccacttg aacctggaaa | 300 |
| agagcagcaa ctaaaagaaa agcttgagca agtcaaggta attttatttt ctcaaatccc | 360 |
| ccagggcctg cttgcataaa gaagtatatg aatctatttt ttaattcaat cattggtttt | 420 |
| ctgcccatta ggttattcat agttccttgc taaagtgttt ttctcacaac tttatttctt | 480 |
| cttaaccctg cagttctgaa ccagtgcaca taagaacata tgtatatatg tgtgtgtgtg | 540 |
| tatttatata tacacacaca catattgcat ctatacatct acacatatag atgtatagat | 600 |
| tcaatatgtc taaaaatgta tataattcac agttttatc tttgatttga atatttaagg | 660 |
| gactgagact cacactcata tactttt | 687 |

```
<210> SEQ ID NO 53
<211> LENGTH: 415
<212> TYPE: DNA
<213> ORGANISM: Homo sapiens
```

<400> SEQUENCE: 53

```
aactgttggt atttgaggta ccactgggcc ctcggtcaag tcgcttcatt ttgatagact    60
aatcaataga agcaaagaca aggtagttgg aattgtgctg taattcattt taaacgttgt   120
tgcatttgtc tgtttcagtt actggtggaa gagttgcccc tgcgccaggg aattctcaaa   180
caattaaatg aaactggagg acccgtgctt gtaagtgctc ccataagccc agaagagcaa   240
gataaacttg aaaataagct caagcagaca aatctccagt ggataaaggt tagacattaa   300
ccatctcttc cgtcacatgt gttaaatgtt gcaagtattt gtatgtattt tgtttcctgg   360
gtgcttcatt ggtcggggag gaggctggta tgtggattgt tgttttgttt tgttt        415
```

<210> SEQ ID NO 54
<211> LENGTH: 642
<212> TYPE: DNA
<213> ORGANISM: Homo sapiens

<400> SEQUENCE: 54

```
ttttgtagac ggttaatgaa taattttgaa tacattggtt aaatcccaac atgtaatata    60
tgtaaataat caatattatg ctgctaaaat aacacaaatc agtaagattc tgtaatattt   120
catgataaat aactttgaa aatatatttt taaacatttt ggcttatgcc ttgagaatta   180
tttacctttt taaaatgtat tttcctttca ggtttccaga gctttacctg agaaacaagg   240
agaaattgaa gctcaaataa aagaccttgg gcagcttgaa aaaagcttg aagaccttga   300
agagcagtta aatcatctgc tgctgtggtt atctcctatt aggaatcagt tggaaattta   360
taaccaacca aaccaagaag gaccatttga cgttaaggta gggaactttt tgctttaaat   420
attttttgtct tttttaagaa aaatggcaat atcactgaat tttctcattt ggtatcatta   480
ttaaagacaa aatattactt gttaaagtgt ggtaaggaag actttattca ggataaccac   540
aataggcaca gggaccactg caatggagta ttacaggagg ttggatagag agagattggg   600
ctcaactcta aatacagcac agtggaagta ggaatttata gc                      642
```

<210> SEQ ID NO 55
<211> LENGTH: 843
<212> TYPE: DNA
<213> ORGANISM: Homo sapiens

<400> SEQUENCE: 55

```
aagctttgat actgtgcttt aagtgtttac cctttggaaa gaaaataatt ttgacagtga    60
tgtagaaata attatttgat atttatttca aaacaaaatt tatatccaat actaaacaca   120
gaattttgta aaacaataag tgtataaagt aaaatgaaca ttaggattat tgagattatt   180
gtagctaaaa ctagtgttta ttcatataaa ttatgttaat aaattgtatt gtcattattg   240
cattttactt ttttgaaaag tagttaatgc ctgtgtttct atatgagtat tatataattc   300
aagaagatat tggatgaatt ttttttaagt ttaatgtgtt tcacatctct gtttcttttc   360
tctgcaccaa aagctacatt tttgtgccct tatgtaccag gcagaaattg atctgcaata   420
catgtggagt ctccaagggt atatttaaat ttagtaattt tattgctaac tgtgaagtta   480
atctgcacta tatgggttct tttccccagg aaactgaaat agcagttcaa gctaaacaac   540
cggatgtgga agagattttg tctaaagggc agcatttgta caaggaaaaa ccagccactc   600
agccagtgaa ggtaatgaag caacctctag caatatccat tacctcataa tgggttatgc   660
ttcccctgtt gtacatttgc cattgacgtg gactatttat aatcagtgaa ataacttgta   720
aggaaatact ggccatactg taatagcaga ggcaaagctg tcttttttgat cagcatatcc   780
```

| | |
|---|---|
| tatttatata ttgtgatctt aaggctatta acgagtcatt gctttaaagg actcatttct | 840 |
| gtc | 843 |

<210> SEQ ID NO 56
<211> LENGTH: 745
<212> TYPE: DNA
<213> ORGANISM: Homo sapiens

<400> SEQUENCE: 56

| | |
|---|---|
| aattaagcat gttgctgaga gggaactgtt tttttgttgg tttgttttca ctaatgtttg | 60 |
| cactctactt cctttaaata aaattatgcc tggagaaagg gttttgtat ggagcaattg | 120 |
| ataaatattt gatgggtggt tggctaaaat aattataatt cctttaaaag aaattctacc | 180 |
| cactaaagtt aatttagaag taaaatataa tagaaatcca ataatatatt caccaaatgg | 240 |
| attaagatgt tcatgaatta tcttcaaagt gttaatcgaa taagtaatgt gtatgctttt | 300 |
| ctgttaaaga ggaagttaga agatctgagc tctgagtgga aggcggtaaa ccgtttactt | 360 |
| caagagctga gggcaaagca gcctgaccta gctcctggac tgaccactat tggagcctgt | 420 |
| aagtatactg gatcccattc tctttggctc tagctatttg ttcaaaagtg caactatgaa | 480 |
| gtgatgactg ggtgagagag aaaatttgtt tcaattctaa agatagagat aaacctttgt | 540 |
| gttattgact gtgcaaaaag tcttagagta cattccttgg aaattgactc tgattcaaag | 600 |
| tgttgcatga caacgggata tggggagtgt tctctggaga tacacccaca aggaagagaa | 660 |
| gagcacaggg agattgtgga gagtctgaaa tgtgatttgt ctgcagcaga ggcctaagcc | 720 |
| agtctcgcag gagcctacac tggct | 745 |

<210> SEQ ID NO 57
<211> LENGTH: 3159
<212> TYPE: DNA
<213> ORGANISM: Homo sapiens

<400> SEQUENCE: 57

| | |
|---|---|
| aagcttgaga gacaagaaac attcttccat tctactcatc ttcttctcta atgaggagac | 60 |
| aaccttaaaa gcacagttac atagccataa aaattaatga ttggctacct cagaatgaaa | 120 |
| attcaatgtc tcattttttt ttaatattct tagaatcgtt cactggttgt ccagtgtgag | 180 |
| tctcctgttg agatgtcttt tgcagctttc cttgaaacct ttcattccaa actacatagt | 240 |
| ccaataattt tgccaccaat cttctggtta tattatgctc ttgagtctgt tgtctataaa | 300 |
| cttgattagg cattccttcc cctcaccact cacctctgat aacccagctg tgtgttggta | 360 |
| tttagtatca attcacacca gcaagttcag ccctcttcaa tcaatatagg gccacacacg | 420 |
| gactttgac tgactactcc ccaagtattt cacattttgg ggccttatct ccagtttctc | 480 |
| accacagttg ttcatcactg tgtttcttac tagccaggtg tttataaaaa cactaatacc | 540 |
| taacactatt gatcacctac tatagtgtca ggcgctgtaa taatattatt gtgatgatga | 600 |
| tgattatgct gctctttctg gcattgtcat acgtgtattg cttgtactac tcactgaatc | 660 |
| tacacaactg cccttatgac atttaccctg ttattattcc tcttttaagg taaatacatg | 720 |
| aaaaatgctt cccactttgc cttgcttact gcttattgct agtactgaac aaatgttaga | 780 |
| actgaaactt agagaggtta tgtggctttta ccaaggtccc agagttccta gggtagagaa | 840 |
| caggattgtc taccagacat tttaattcta gtactatgca tcttaaccat taccataggc | 900 |
| tgacttactc tacagtgtcc aacatattca ctattaagat ttatttaatg actttgaaac | 960 |

```
agtatttcat gtctaaatag aaaaactact aactcgcatt tttaagaaaa tattgtatct   1020 tggttttct  tcactgctgg ccagtttact aacaatctga aataaaaga  aaaaaatatg   1080 ataaactgct cccagtataa aatacagagc taagacaaga acgtttcatt ggctttgatt   1140
tccctagggt ccagcttcaa attaatttac ttcctattca agggaattct taaatcagaa   1200
agaagatctt atcccatctt gttttgcctt tgttttttct tgaataaaaa aaaaataagt   1260
aaaatttatt tccctggcaa ggtctgaaaa cttttgtttt ctttaccact tccacaatgt   1320
atatgattgt tactgagaag gcttatttaa cttaagttac ttgtccaggc atgagaatga   1380
gcaaaatcgt ttttaaaaa  attgttaaat gtatattaat gaaaaggttg aatcttttca   1440
ttttctacca tgtattgcta acaaagtat  ccacattgtt agaaaagat  atataatgtc   1500 atgaataaga gtttggctca aattgttact cttcaattaa atttgactta ttgttattga   1560
aattggctct ttagcttgtg tttctaattt ttcttttct  tctttttcc  tttttgcaaa   1620 aacccaaaat attttagctc ctactcagac tgttactctg gtgacacaac ctgtggttac   1680
taaggaaact gccatctcca aactagaaat gccatcttcc ttgatgttgg aggtacctgc   1740
tctggcagat ttcaaccggg cttggacaga acttaccgac tggctttctc tgcttgatca   1800
agttataaaa tcacagaggg tgatggtggg tgaccttgag gatatcaacg agatgatcat   1860
caagcagaag gtatgagaaa aaatgataaa agttggcaga agttttctt  taaaatgaag   1920 attttccacc aatcacttta ctctcctaga ccatttccca ccagttctta ggcaactgtt   1980
tctctctcag caaacacatt actctcacta ttcagcctaa gtaatcaa   ggatataaat   2040 taatgcaaat aacaaagta  gccatacatt aaaaaggaaa tatacaaaaa aaaaaaaaa    2100 aaaaagcaga aaccttacaa gaatagttgt ctcagttaaa tttactaaac aacctggtat   2160
tttaaaaatc tattttatac caaataagtc actcaactga gctatttaca tttaaactgt   2220
ttgttttgga ctacgcagcc caacatattg cagaatcaaa tataatagtc tgggaattga   2280
ttattatcca ctcttctaag ttgtctgtgc caatttgcct tctccaatga taaggataat   2340
tgaaagagag ctataactta aaaagagaaa agtaacaaaa cataagatat ttaaaattac   2400
cctagatctt aaagttggca tttatgcaat gccatgttca aatgaacatg ttttaatac    2460 aaatagtgca tttttcagcc tcagtgtaat ccatttggta aaattatgac atcaactaga   2520
aacattagaa tacattgatg taaatatggt ttacctagct agatcaaata tactatatat   2580
cttttatatt tgtgaatggt taagaaaaat aatgttggaa ttgttataca ttaaagtttt   2640
ttcacttgta acagctttca agcctttcta aagaaataca aagttgtgct gaaggtattt   2700
aggtattaaa gtactacctt ttgaaaaaac aagaagtgag gcagacagag taagggaat    2760 ttctttgtaa aataaacttc accaattcca taggaataaa agtaatttga tagtaaacaa   2820
cctgcattta aaggccttga gcttgaatac agaagacctg aattcagtgc catttgcaaa   2880
tgatgattgt ggtcaagcca tctctggatc ttcgtttcct attctgagta cagagcatac   2940
agagtacaca ttcacattca caatatagtt atggatatgg atgtatataa atatatgtaa   3000
atactacata tatgtaccta aaatttgttt tacttctgct ttaaaaaag  taattatagc   3060 cacattttc  agaaaagta  actgaggctc atagatgtca aattcccagt aagtagcaga   3120
acaaggattc aaatccaagt ccatttgatt cctaagctt                          3159
```

<210> SEQ ID NO 58
<211> LENGTH: 547
<212> TYPE: DNA
<213> ORGANISM: Homo sapiens
<220> FEATURE:
<221> NAME/KEY: misc_feature
<222> LOCATION: (1)..(547)
<223> OTHER INFORMATION: n is unknown

<400> SEQUENCE: 58

```
tctaagaatg aaacatatct cctgttaaat tgttttctat aagcncttat acagtaacat      60
cttttttatt tctaaaagtg ttttggctgg tctcacaatt gtactttact ttgtattatg     120
taaaaggaat acacaacgct gaagaaccct gatactaagg gatatttgtt cttacaggca    180
acaatgcagg atttggaaca gaggcgtccc cagttggaag aactcattac cgctgcccaa     240
aatttgaaaa acaagaccag caatcaagag gctagaacaa tcattacgga tcgaagtaag    300
tttttttaaca agcatgggac acacaaagca agatgcatga caagtttcaa taaaaactta    360
agttcatata tcccccctcac atttataaaa ataatgtgaa ataattgtaa atgataacaa    420
ttgtgctgag atttttcagtc cataatgtta ccttttaata aatgaatgta attccattga    480
atagaagaaa tacattttta aatcaattca gggcttatat agttgcaaag catgcattga    540
tgggtgt                                                               547
```

<210> SEQ ID NO 59
<211> LENGTH: 677
<212> TYPE: DNA
<213> ORGANISM: Homo sapiens

<400> SEQUENCE: 59

```
tttctacaga tgatcatatt ggtctaggga tcaagaatga gataaattta tatatatgtt      60
gatgttctat gtcaccttca cgaaaataat ttaacagaaa ctaatatttg ccatcaaaaa    120
agcaaagaat cctgttgttc atcatcctag ccataacaca atgaataatt ttttaaataa    180
gcaacataaa tgtgagataa cgtttggaag ttacatttaa aatgtctcct ccagactagc    240
atttactact atatatttat ttttcctttt attctagttg aaagaattca gaatcagtgg    300
gatgaagtac aagaacacct tcagaaccgg aggcaacagt tgaatgaaat gttaaaggat    360
tcaacacaat ggctggaagc taaggaagaa gctgagcagg tcttaggaca ggccagagcc    420
aagcttgagt catggaagga gggtccctat acagtagatg caatccaaaa gaaaatcaca    480
gaaaccaagg ttagtatcaa agatacctt ttaaaataaa atactggtta catttgataa    540
aattatacca tagattgtaa tttaatgatg tttaatgtaa agttattaac agaaaatcac    600
gttaaagctg aaatgaacag tagactttgt atatttattt tcttagagac agagtctcac    660
tgtcacccag gctaaag                                                    677
```

<210> SEQ ID NO 60
<211> LENGTH: 589
<212> TYPE: DNA
<213> ORGANISM: Homo sapiens

<400> SEQUENCE: 60

```
agccacttat tgccaattaa ttgctactaa gttgaaatac ttgatactgg ttattgctca     60
agatgctgca tttgaaaagt ttgtcctgaa aggtgggtta ccttatactg tcatgattga    120
ctaaatcata tggtaggtta aaagcaatct aatatatgta ttctgacctg aggattcaga    180
agctgtttac gaagtatttt aagacactcc aactagagat tcataaaaa aaactgacat     240
tcattctctt tctcataaaa atctatagca gttggccaaa gacctccgcc agtggcagac    300
aaatgtagat gtggcaaatg acttggccct gaaacttctc cgggattatt ctgcagatga    360
```

```
taccagaaaa gtccacatga taacagagaa tatcaatgcc tcttggagaa gcattcataa    420
aaggtatgaa ttacattatt tctaaaacta ctgttggctg taataatggg gtggtgaaac    480
tggatggacc atgaggattt gttttttcaa tccagctaaa ctggagcttg ggagggttca    540
agacgataaa taccaactaa actcacggac ttggctcaga cttctattt                589

<210> SEQ ID NO 61
<211> LENGTH: 618
<212> TYPE: DNA
<213> ORGANISM: Homo sapiens

<400> SEQUENCE: 61
tatattacaa tttagttcct ccatctttct cttttatga gttcactagg tgcaccattc      60
tgatatttaa taattgcatc tgaacatttg gtcctttgca gggtgagtga gcagaggct    120 gctttggaag aaactcatag attactgcaa cagttccccc tggacctgga aaagtttctt    180
gcctggctta cagaagctga aacaactgcc aatgtcctac aggatgctac ccgtaaggaa    240
aggctcctag aagactccaa gggagtaaaa gagctgatga acaatggca agtaagtcag     300 gcatttccgc tttagcactc ttgtggatcc aattgaacaa ttctcagcat ttgtacttgt    360
aactgacaag ccagggacaa acaaaatag ttgcttttat acagcctgat gtatttcggt     420
atttggacaa ggaggagaga ggcagaggga aaggaaaca tcatttataa ttccacttaa     480
caccctcgtc ttagaaaaag tacatgctct gaccaggaaa acatttcgat ataaaaccag    540
agcttcggtc aaggagaaac tttgctctag agaaataact tagggattgg tttattaaat    600
tttaaaagtg acacaaaa                                                  618

<210> SEQ ID NO 62
<211> LENGTH: 240
<212> TYPE: DNA
<213> ORGANISM: Homo sapiens

<400> SEQUENCE: 62
agtgcggagt acaaagtggc cgtttattat tattgactgg tgaggcctgt gctccaaaat     60
tcattctgtc aacagaatgt aagcaaagtt ggcattttaa agcagggctc tttcagtttc    120
tgggttttct caggattgct atgcaacagg atcagtgctg tagtgcccgg ttcaagctga    180
aaatgttaca caggaagaca taccatgtaa aggtcagatt cttctactat aataattttc    240

<210> SEQ ID NO 63
<211> LENGTH: 360
<212> TYPE: DNA
<213> ORGANISM: Homo sapiens
<220> FEATURE:
<221> NAME/KEY: misc_feature
<222> LOCATION: (1)..(360)
<223> OTHER INFORMATION: n is unknown

<400> SEQUENCE: 63
aatnacattc atagcttgtt tcttttcttt rgtaattctg cacatattct tcttcctgct      60
gtcctgtagg acctccaagg tgaaattgaa gctcacacag atgtttatca aacctggat     120 gaaaacagcc aaaaaatcct gagatccctg gaaggttccg atgatgcagt cctgttacaa    180
agacgtttgg ataacatgaa cttcaagtgg agtgaacttc ggaaaaagtc tctcaacatt    240
aggtaggaaa agatgtggag caaaaaggcc acaaataaat naaatggcc aaattttcct     300 cattgtctta gcacaagtaa ctggtatctc acatgtctac gtaaatcatc ccaatttcag    360
```

<210> SEQ ID NO 64
<211> LENGTH: 343
<212> TYPE: DNA
<213> ORGANISM: Homo sapiens

<400> SEQUENCE: 64

```
gtacttttct atggaattgt tagaatcatc aattacactt ctagatattc tgacatggat      60
cgctgctgtt tgctgttctt tttcaggtcc catttggaag ccagttctga ccagtggaag     120
cgtctgcacc tttctctgca ggaacttctg gtgtggctac agctgaaaga tgatgaatta     180
agccggcagg cacctattgg aggcgacttt ccagcagttc agaagcagaa cgatgtacat     240
agggtaggac atttttaagc ctcgtgcctt gcacatgtta agcacatagt aatccagtga     300
ctattttaaa attaattttg ttttaaatta agttgaatag aaa                       343
```

<210> SEQ ID NO 65
<211> LENGTH: 360
<212> TYPE: DNA
<213> ORGANISM: Homo sapiens

<400> SEQUENCE: 65

```
taaccatcag tgtataaata aaagagatag aaattgacct ggagtttcat aaacaagttc      60
tgagcaccca ggattaattt tgagaagaat gccacaagcc tttcttagca cttcttttca     120
tctcatttca caggccttca agagggaatt gaaaactaaa gaacctgtaa tcatgagtac     180
tcttgagact gtacgaatat ttctgacaga gcagcctttg gaaggactag agaaactcta     240
ccaggagccc agaggtaatt gaatgtggaa ctataataac atattgatag aaggatcagt     300
ggtgacggag cagcccatcc attcttgctg ccagggtctg gatagctctc atattttctt     360
```

<210> SEQ ID NO 66
<211> LENGTH: 500
<212> TYPE: DNA
<213> ORGANISM: Homo sapiens

<400> SEQUENCE: 66

```
aaacgtcgga ttgatataag gtagaaactc aggaagatat actttagatg ttctgggctg      60
tatcaaaatt tatgccaaag tataaaaaag ccgttaatca gtaggttacc ctcttgttca     120
actgtactct ttcttctctt cagtatgacc tttttgacaa tgtttaaaaa aaagaatgt      180
ggcctaaaac cttgtcatat tgccaattta gagctgcctc ctgaggagag agcccagaat     240
gtcactcggc ttctacgaaa gcaggctgag gaggtcaata ctgagtggga aaaattgaac     300
ctgcactccg ctgactggca gagaaaaata gatgagaccc ttgaaagact ccaggaactt     360
caagaggcca cggatgagct ggacctcaag ctgcgccaag ctgaggtgat caagggatcc     420
tggcagcccg tgggcgatct cctcattgac tctctccaag atcacctcga gaaagtcaag     480
gtacggtcta cttctttact                                                 500
```

<210> SEQ ID NO 67
<211> LENGTH: 989
<212> TYPE: DNA
<213> ORGANISM: Homo sapiens

<400> SEQUENCE: 67

```
gaattctcca actactggcc tcataggatt gttgggtaga aataaaatca gtttatgtat      60
gaatagagct catcatggca ttaggcacct aggaagtgct caacaaatag tagttatcat     120
tattccccca ttaacaaata tccattgtta taatactacc acaagagact gtcttagtct     180
```

```
gttccagctg ctataataga aatgccataa attggatagc ttgtgaaaca acaaaaactt     240
atttctcact gttctggagg ttgagaagtc caagatcaaa ataccagtca gatttggagt     300
ctggggaagg cccattcctc atacaaagca ccttctcact gcaccctcac atgctgaaag     360
gagctagcta gctctctgag gtctctttta taagggcgct aatcccaaaa atcacctccc     420
taaaggcccc atctcctaat accattgcct taggtgtttt gatttcgttt ccttttatt      480 ttttaggatt tcaacatagg aatttgaggg gggacacaaa cattcaaacc gtagcataga     540
gcaaacatta ctggcactgc accctaaaga gaataagccc aggtatcagt tcttcttgtt     600
ttaaatattc tcatcttcca atttgctttt gactattgca cacaggcact tcgaggagaa     660
attgcgcctc tgaaagagaa cgtgagccac gtcaatgacc ttgctcgcca gcttaccact     720
ttgggcattc agctctcacc gtataacctc agcactctgg aagacctgaa caccagatgg     780
aagcttctgc aggtaagcac attgtaaaca ttgttgtcct ttgttacagt aaaataatat     840
acagataaaa tttgtaaaga acaatgaaag tacttttttc atgtaatgtt catggtaata     900
tttgtgagga taggatattt tatattagtt tataattccc atctaaacat tttcaaatta     960
ttaatattaa ttttggaagc aactaagac                                       989

<210> SEQ ID NO 68
<211> LENGTH: 167
<212> TYPE: DNA
<213> ORGANISM: Homo sapiens

<400> SEQUENCE: 68
tatagaatga gagaacataa tttctctcct tttcctccca ggtggccgtc gaggaccgag      60
tcaggcagct gcatgaagcc cacagggact tggtccagc atctcagcac tttctttcca     120
gtaagtcatt ttcagctttt atcacttaac tttattgcat cttgatt                  167

<210> SEQ ID NO 69
<211> LENGTH: 232
<212> TYPE: DNA
<213> ORGANISM: Homo sapiens

<400> SEQUENCE: 69
agtgtaaaac agtaattctg gagattaatg ttgtctttcc tgtttgcgat gaatttgacc      60
tccttgcctt tctttttttc ctcccttctt ttcagcgtct gtccagggtc cctgggagag     120
agccatctcg ccaaacaaag tgccctacta tatcaagtaa gttggaagta tcacatttt     180 aaaagagcat ttattgtgac taacctgtat attcacaagt gagtttattt tt            232

<210> SEQ ID NO 70
<211> LENGTH: 314
<212> TYPE: DNA
<213> ORGANISM: Homo sapiens

<400> SEQUENCE: 70
ctttctcttt tcttttcct ttccgtttg aaagcccaac tgccagtctc tgggtgtccg       60
ggttcccagg tccctaggtg ggcgagccga cacacgcccg ccccgtctgg gggcagcgcc    120 ccctcccgg cccgcccgcg ccggctcctc cgcagtgctt tcagctgtga gcttgggcgg     180
cggcggcggc ggcgctccac tttcggggag cccggcggct ctgggaagct cactcctcca    240
ctcgtaccca cactcgaccg cggagccctt gcagccatga gggaacagct caaagggtaa    300
gtggatcgcg gccc                                                      314
```

<210> SEQ ID NO 71
<211> LENGTH: 218
<212> TYPE: DNA
<213> ORGANISM: Homo sapiens

<400> SEQUENCE: 71

```
tttttcctg ttttcttgac tactcatggt aaatgctaaa gtctttcttt atgttttgtg    60
ttttagccac gagactcaaa caacttgctg ggaccatccc aaaatgacag agctctacca   120
gtctttaggt aaggacatgg ccatgtttcc tccaagttaa atgacaggtg acctttagga   180
taaagtagtt tgcagtgtga aagttacttt gctactac                           218
```

<210> SEQ ID NO 72
<211> LENGTH: 343
<212> TYPE: DNA
<213> ORGANISM: Homo sapiens
<220> FEATURE:
<221> NAME/KEY: misc_feature
<222> LOCATION: (1)..(343)
<223> OTHER INFORMATION: n is unknown

<400> SEQUENCE: 72

```
ggcaaatcac tgggcgtcgg gggtgggttg tctgntattt ctgatggaat aacaaatgct    60
ctttgttttc cctcttttca gctgacctga ataatgtcag attctcagct tataggactg   120
ccatgaaact ccgaagactg cagaaggccc tttgctgtaa gtattggcca gtatttgaag   180
atcttgatac tatgtctttg cttagaataa aaagtaggtt gggtacattt ttacttagag   240
aggggagaaa cagctgtcac aattcctgtt gcaatgtata attcattctt taatgtatcc   300
ttggcctaga gtttgcctag aatgttttgt tttatttta gaa                      343
```

<210> SEQ ID NO 73
<211> LENGTH: 351
<212> TYPE: DNA
<213> ORGANISM: Homo sapiens

<400> SEQUENCE: 73

```
ggtatgagag agtcctagct aggattctca gaggaaaaag gacactgaaa ggaaggtttt    60
actctttgag tcatttgtga ttttatttgt ttttgcagt ggatctcttg agcctgtcag    120
ctgcatgtga tgccttggac cagcacaacc tcaagcaaaa tgaccagccc atggatatcc   180
tgcagattat taattgtttg accactattt atgaccgcct ggagcaagag cacaacaatt   240
tggtcaacgt ccctctctgc gtggatatgt gtctgaactg gctgctgaat gtttatgata   300
cgtacgtatg gcatgttttt atttcccggg ctctgtcaca ggaggcttag c            351
```

<210> SEQ ID NO 74
<211> LENGTH: 250
<212> TYPE: DNA
<213> ORGANISM: Homo sapiens

<400> SEQUENCE: 74

```
agaagtgttt accctctagg aaagggtcta gtaattgttt ctgctttga ttcttcataa    60
taggggacga acagggagga tccgtgtcct gtcttttaaa actggcatca tttccctgtg   120
taaagcacat ttggaagaca agtacagatg taagtcgtgt atactaatgc tgtattcttt   180
tattaatgtt ggctaattac cctagttcta gatgggaaat gacagactgt tcttatttga   240
cagcagattc                                                          250
```

<210> SEQ ID NO 75

```
<211> LENGTH: 433
<212> TYPE: DNA
<213> ORGANISM: Homo sapiens
<220> FEATURE:
<221> NAME/KEY: misc_feature
<222> LOCATION: (1)..(433)
<223> OTHER INFORMATION: n is unknown

<400> SEQUENCE: 75
aaaaataata aatatccaga ttagcacaaa ttagaagtaa ccccactact gtggaaatac      60
tggctactct tgagaattgc tactggaatt gagttggatg tcaggttctg ctggcatcca     120
tgggtgctgt gttttgactg ttgcaatttt cttcttcctt tgtagacctt ttcaagcaag     180
tggcaagttc aacaggattt tgtgaccagc gcaggctggg cctccttctg catgattcta     240
tccaaattcc aagacagttg ggtgaagttg catcctttgg gggcagtaac attgagccaa     300
gtgtccggag ctgcttccaa tttgtaagtt attcaccttc taggtaacat atttattctt     360
tcatatttta gaaattaatt aanaaaccca cagagcttcg ttttctcata ttagctcttc     420
agtaggcagt agg                                                        433

<210> SEQ ID NO 76
<211> LENGTH: 354
<212> TYPE: DNA
<213> ORGANISM: Homo sapiens

<400> SEQUENCE: 76
ttaatcgaac tgatatacac ctcctttgcc atcttgcctt ctttcctttc atcctttggc      60
cctccttctc tctccctcct gtctttgcag gctaataata agccagagat cgaagcggcc     120
ctcttcctag actggatgag actggaaccc cagtccatgg tgtggctgcc cgtcctgcac     180
agagtggctg ctgcagaaac tgccaagcat caggccaaat gtaacatctg caaagagtgt     240
ccaatcattg gattcaggta ttaggaacca aaaaaaaaaa tgtcattttt ttctcatcat     300
ttttcacctt tttatgactt gatcttttat ctcctgtgcc agttgctgtt agtt           354

<210> SEQ ID NO 77
<211> LENGTH: 247
<212> TYPE: DNA
<213> ORGANISM: Homo sapiens

<400> SEQUENCE: 77
ctcaaattag aacgtggtag aaggtttatt aaagagtgtt ctttgggaat ttgattcgaa      60
gaaatacata cgtgtttgtt tttgctcttt atcaggtaca ggagtctaaa gcactttaat     120
tatgacatct gccaaagctg cttttttttct ggtcgagttg caaaaggcca taaaatgcac    180
tatcccatgg tggaatattg cactccggta agtttgacgc cagcctgacg tgagagttag     240
ttcacct                                                               247

<210> SEQ ID NO 78
<211> LENGTH: 952
<212> TYPE: DNA
<213> ORGANISM: Homo sapiens

<400> SEQUENCE: 78
aagcttgtat gtttcttta tttatcataa caacgtattg aggtgttgtt gctcccattt       60
tactgatgat cagagcctct gagaagtaaa taactcagcc aaattagtac atgccaggcc     120
tggtttcaga gccccatttg tctgattcca aagcctttgc tcacaaccac aacactctcc     180
ttaattacaa aacaagtgtc atgggcagaa gactggagtg gtcattagtt ttgaaatcat     240
```

```
cctgtcctaa atctgatctc accatgatct ccctttaga ctacatcagg agaagatgtt    300
cgagactttg ccaaggtact aaaaaacaaa tttcgaacca aaaggtattt tgcgaagcat    360
ccccgaatgg gctacctgcc agtgcagact gtcttagagg gggacaacat ggaaacgtga    420
gtagtagcaa aagcagaaca cactcttgtt tgatgtatat ttgaactcct ctcagctgaa    480
caccctcctt cactcccaaa tgcaaacagt ctcttctatt tctttctttt tatttacatt    540
agctgaaaag agaaaaataa gctgatgtcc agttgccact ttcccacgtc acttgacaat    600 ttcttttttcc aaaagttaaa ctttatctca caggggaaa aaaaaaaaaa aaccacaaca    660
caatacagcc actaattgcc ttacaagcct tataagaaat atgggactgt ttacaaatga    720
gtgattccag tatttcattt tgattttctc tctcacaatc agtaatgtgt gtctttgtat    780
ctcatgtgtg gtcatatcta gtcactgtct actcacaaat cagtaaatgc ttgtgtcttt    840
ttgtatctca ttgtgtgtgg tcatatctag tcacttgctt tctaccaaaa gaaaatatag    900
tcacaggaaa ctactcacgt aagtagtaat gattctcaag atcaaggggg ag            952

<210> SEQ ID NO 79
<211> LENGTH: 171
<212> TYPE: DNA
<213> ORGANISM: Homo sapiens

<400> SEQUENCE: 79
tttcagtaaa ttttttttgcg gctgagaaag cgtgtgtctc cttcaccacc tcattttttg     60
ttttgcagtc ccgttactct gatcaacttc tggccagtag attctgcgtg agtacttttt    120
tggctgaagg gtgctgctac caccaacaca ttcgctcgct tggttctctt t              171

<210> SEQ ID NO 80
<211> LENGTH: 215
<212> TYPE: DNA
<213> ORGANISM: Homo sapiens

<400> SEQUENCE: 80
aatggatggt atctgtgact aatcacattt tctccttata ggcctgcctc gtcccctcag     60 cttttcacacg atgatactca ttcacgcatt gaacattatg ctagcaggta tgaggctagt    120
tgtatgccag gcaaatattg attgaaataa ctaaccaagg aaagctaacc tataatattt    180
taaacaaatc ttttctttttt ttccccaaac ttgtc                               215

<210> SEQ ID NO 81
<211> LENGTH: 214
<212> TYPE: DNA
<213> ORGANISM: Homo sapiens

<400> SEQUENCE: 81
gattctaaga cgtcacataa gttttaatga gcttttacgt tttttatcag gctagcagaa     60
atggaaaaca gcaatggatc ttatctaaat gatagcatct ctcctaatga gagcatgtaa    120
gtatcccatc tcttttttaca aaatgttcct gacaatgaaa ttgctttgag ggatttagag    180
gtaggatagc acaggatata ggaattagca tcat                                 214

<210> SEQ ID NO 82
<211> LENGTH: 299
<212> TYPE: DNA
<213> ORGANISM: Homo sapiens

<400> SEQUENCE: 82
```

```
cctgagtccc taaccccaa agcaaaataa gggggggaaa aaaccaaaac ctttgatttt      60
attttccaga gatgatgaac atttgttaat ccagcattac tgccaaagtt tgaaccagga     120
ctcccccctg agccagcctc gtagtcctgc ccagatcttg atttccttag agagtgagga    180
aagaggggag ctagagagaa tcctagcaga tcttgaggaa gaaaacaggt gagttttctt    240
tctagctttg tcattggtat gcagagtgca tacacttgca cacatagaaa agtgccagg     299
```

<210> SEQ ID NO 83
<211> LENGTH: 747
<212> TYPE: DNA
<213> ORGANISM: Homo sapiens
<220> FEATURE:
<221> NAME/KEY: misc_feature
<222> LOCATION: (1)..(747)
<223> OTHER INFORMATION: n is unknown

<400> SEQUENCE: 83

```
ttttttcttt tttacttttt tgatgccaat aggaatctgc aagcagaata tgaccgtcta     60
aagcagcagc acgaacataa aggcctgtcc ccactgccgt cccctcctga aatgatgccc    120
acctctcccc agagtccccg ggatgctgag ctcattgctg aggccaagct actgcgtcaa    180
cacaaaggcc gcctggaagc caggatgcaa atcctggaag accacaataa acagctggag    240
tcacagttac acaggctaag gcagctgctg gagcaagtga ggagagagat gggattttta    300
caaacattca ttttcccctc ttaaacaaaa ctaaacctca gagagcactt tttataggtg     360
caacaagcat caattcttaa gtgcttggta tgtgcctgca aagtgatagt atcaaaggat     420
agaagtagag gagatagaaa aactagtgtg tcttttttgt atttgtccaa tattgtttcc     480
taccaaaatg gttttttctt gaccaatttg aaatacatct tggggaaaaa aacgcctaaa     540
ggtttccact agttctctaa aagtgaatat ttcacttctt gaaatggaac tatttcattt     600
acaattagtt atattttctg gnatacctt gngttttttt tctcctaatc cctaacacat     660
agtttctttt aagccttcca tcgaaaacct agcaaggata cttgcatttg taagaaggac    720
ctaccctgga acatagttnt tggcttt                                        747
```

<210> SEQ ID NO 84
<211> LENGTH: 287
<212> TYPE: DNA
<213> ORGANISM: Homo sapiens

<400> SEQUENCE: 84

```
gtcctgagtg tgtataatat tttaaaattt atacatttgt atgtttatta tgaaaagtaa     60
ttctgttttc ttttggatga cttagcccca ggcagaggcc aaagtgaatg gcacaacggt    120
gtcctctcct tctacctctc tacagaggtc cgacagcagt cagcctatgc tgctccgagt     180
ggttggcagt caaacttcgg actccatggg taagtgtcct agctactctc agattttgtt    240
gtctgaagaa aggtagagtc gtattacagg gacatgaata tttggcc                 287
```

<210> SEQ ID NO 85
<211> LENGTH: 338
<212> TYPE: DNA
<213> ORGANISM: Homo sapiens

<400> SEQUENCE: 85

```
aaaaatgtaa tcatggccct ttaatatctg ttttctataa atgtaatttt ccattatttg     60
tttttgcttt tattaaggtg aggaagatct tctcagtcct ccccaggaca caagcacagg    120
gttagaggag gtgatggagc aactcaacaa ctccttccct agttcaagag gtaagcttcca   180
```

```
atacctagaa gggactcaga tttgctggga tcaggccact cgcttcccta cccaactggt    240
gtgtgtattt tccatatgga agccaacacg cagtatcaga atggcaattt gggtccatgg    300
tgaaaagatt tgattttaa gtgtgaattt gttgttta                              338

<210> SEQ ID NO 86
<211> LENGTH: 253
<212> TYPE: DNA
<213> ORGANISM: Homo sapiens

<400> SEQUENCE: 86
gcatgttttt tttccctttc tgatatctct gcctcttcct ctctctatta ttttaggaag    60
aaatacccct ggaaagccaa tgagagaggt tagtgagatt caggctcacg gccatggctt    120
ctgtctgtct catcctgctt tttatgtttg gcgtttgtgt aagaattgtg tgtgtgcacg    180
cgcatgtgtg tattacacat tgtgtcatca tgtaaggatg gtagtcacct ctccacttgc    240
agctcattga gaa                                                        253

<210> SEQ ID NO 87
<211> LENGTH: 3162
<212> TYPE: DNA
<213> ORGANISM: Homo sapiens
<220> FEATURE:
<221> NAME/KEY: misc_feature
<222> LOCATION: (1)..(3162)
<223> OTHER INFORMATION: n is unknown

<400> SEQUENCE: 87
gaattctttt gatatatatt tacattggga acctgaatgt agcttgacat ttttccatgt    60
aaacaccagt agcctgatcc aacattaagc tgatactaac aaacaacgtg taatggcttc    120
attaataagg ctttgcttct tcctggaaac tggtgaaaaa tcaaaccttg ttgtgtacac    180
cctcgatgca gcttctgtgt tgtcttcacc cagaaatggg gaatgatttc ccaaatggca    240
aagaaacaga gtgatgctat ctatctgcac cttttgtaaa gtctgtcttt ctttctcttt    300
gttttccagg acacaatgta ggaagtcttt tccacatggc agatgatttg ggcagagcga    360
tggagtcctt agtatcagtc atgacagatg aagaaggagc agaataaatg ttttacaact    420
cctgattccc gcatggtttt tataatattc atacaacaaa gaggattaga cagtaagagt    480
ttacaagaaa taaatctata tttttgtgaa gggtagtggt attatactgt agatttcagt    540
agtttctaag tctgttattg ttttgttaac aatggcaggt tttacacgtc tatgcaattg    600
tacaaaaaag ttataagaaa actacatgta aaatcttgat agctaaataa cttgccattt    660
ctttatatgg aacgcatttt gggttgttta aaaatttata acagttataa agaaagattg    720
taaactaaag tgtgctttat aaaaaaaagt tgtttataaa aacccctaaa aacaaaacaa    780
acacacacac acacacatac acacacacac acaaaacttt gaggcagcgc attgttttgc    840
atccttttgg cgtgatatcc atatgaaatt catggctttt tcttttttg catattaaag    900 ataagacttc ctctaccacc acaccaaatg actactacac actgctcatt tgagaactgt    960
cagctgagtg gggcaggctt gagttttcat ttcatatatc tatatgtcta taagtatata    1020
aatactatag ttatatagat aaagagatac gaatttctat agactgactt tttccatttt    1080
ttaaatgttc atgtcacatc ctaatagaaa gaaattactt ctagtcagtc atccaggctt    1140
acctgcttgg tctagaatgg attttttcccg gagccggaag ccaggaggaa actacaccac    1200
actaaaacat tgtctacagc tccagatgtt tctcatttta acaactttc cactgacaac    1260
```

-continued

| | | | | | |
|---|---|---|---|---|---|
| gaaagtaaag | taaagtattg | gattttttta | aagggaacat | gtgaatgaat | acacaggact | 1320 |
| tattatatca | gagtgagtaa | tcggttggtt | ggttgattga | ttgattgatt | gatacattca | 1380 |
| gcttcctgct | gctagcaatg | ccacgattta | gatttaatga | tgcttcagtg | gaaatcaatc | 1440 |
| agaaggtatt | ctgaccttgt | gaacatcaga | aggtattttt | taactcccaa | gcagtagcag | 1500 |
| gacgatgata | gggctggagg | gctatggatt | cccagcccat | ccctgtgaag | gagtaggcca | 1560 |
| ctctttaagt | gaaggattgg | atgattgttc | ataatacata | aagttctctg | taattacaac | 1620 |
| taaattatta | tgccctcttc | tcacagtcaa | aaggaactgg | gtggtttggt | ttttgttgct | 1680 |
| tttttagatt | tattgtccca | tgtgggatga | gttttaaat | gccacaagac | ataatttaaa | 1740 |
| ataaataaac | tttgggaaaa | ggtgtaagac | agtagcccca | tcacatttgt | gatactgaca | 1800 |
| ggtatcaacc | cagaagccca | tgaactgtgt | ttccatcctt | tgcatttctc | tgcgagtagt | 1860 |
| tccacacagg | tttgtaagta | agtaagaaag | aaggcaaatt | gattcaaatg | ttacaaaaaa | 1920 |
| acccttcttg | gtggattaga | caggttaaat | atataaacaa | acaaacaaaa | attgctcaaa | 1980 |
| aaagaggaga | aaagctcaag | aggaaaagct | aaggactggt | aggaaaaagc | tttactcttt | 2040 |
| catgccattt | tatttctttt | tgattttaa | atcattcatt | caatagatac | caccgtgtga | 2100 |
| cctataattt | tgcaaatctg | ttacctctga | catcaagtgt | aattagcttt | tggagagtgg | 2160 |
| gctgacatca | agtgtaatta | gcttttggag | agtgggtttt | gtccattatt | aataattaat | 2220 |
| taattaacat | caaacacggc | ttctcatgct | atttctacct | cactttggtt | ttggggtgtt | 2280 |
| cctgataatt | gtgcacacct | gagttcacag | cttcaccact | tgtccattgc | gttattttct | 2340 |
| ttttccttta | taattctttc | tttttccttc | ataatttca | aaagaaaacc | caaagctcta | 2400 |
| aggtaacaaa | ttaccaaatt | acatgaagat | ttggttttg | tcttgcattt | ttttccttta | 2460 |
| tgtgacgctg | gaccttttct | ttacccaagg | attttaaaa | ctcagattta | aaacaagggg | 2520 |
| ttactttaca | tcctactaag | aagtttaagt | aagtaagttt | cattctaaaa | tcagaggtaa | 2580 |
| atagagtgca | taaataattt | tgttttaatc | tttttgtttt | tcttttagac | acattagctc | 2640 |
| tggagtgagt | ctgtcataat | atttgaacaa | aaattgagag | ctttattgct | gcattttaag | 2700 |
| cataattaat | ttggacatta | tttcgtgttg | tgttctttat | aaccaccgag | tattaaactg | 2760 |
| taaatcataa | tgtaactgaa | gcataaacat | cacatggcat | gttttgtcat | tgttttcagg | 2820 |
| tactgagttc | ttacttgagt | atcataatat | attgtgtttt | aacaccaaca | ctgtaacatt | 2880 |
| tacgaattat | tttttaaac | ttcagttta | ctgcattttc | acaacatatc | agacttcacc | 2940 |
| aaatatatgc | cttactattg | tattatagta | ctgcttact | gtgtatctca | ataaagcacg | 3000 |
| cagttatgtt | acaaaaaagt | attgactgga | ctgcagtact | ttgttttat | tttaatttag | 3060 |
| ttgttgttac | ttacttactt | actttttaaa | taggtaatac | atgcatatga | gtaaaaaact | 3120 |
| atnatccaga | aagacagttg | aaaacactcc | taagtacccc | tt | | 3162 |

ALTERATIONS IN THE DYSTROPHIN GENE ASSOCIATED WITH SPORADIC DILATED CARDIOMYOPATHY

CROSS-REFERENCE TO RELATED APPLICATION

The present application is related to and claims priority under 35 U.S.C. §119(e) to U.S. provisional patent application Ser. No. 60/359,324 filed on 26 Feb. 2002, incorporated herein by reference.

This work was supported in part by grant No. R01HL62570 from the National Institutes of Health, National Heart, Lung and Blood Institute, Bethesda, Md. The U.S. government may have certain rights.

BACKGROUND OF THE INVENTION

The present invention relates generally to the field of human genetics. Specifically, the present invention relates to methods and materials used to detect a human sporadic dilated cardiomyopathy (DCM) gene, specifically the dystrophin gene, some mutant alleles of which cause susceptibility to sporadic DCM. More specifically, the invention relates to germline mutations in the dystrophin gene and their use in the diagnosis of predisposition to sporadic DCM. The invention also relates to the prophylaxis and/or therapy of sporadic DCM associated with a mutation in the dystrophin gene. The invention further relates to the screening of drugs for sporadic DCM therapy. Finally, the invention relates to the screening of the dystrophin gene for mutations/alterations, which are useful for diagnosing the predisposition to sporadic DCM.

The publications and other materials used herein to illuminate the background of the invention, and in particular, cases to provide additional details respecting the practice, are incorporated herein by reference, and for convenience, are referenced by author and date in the following text and respectively grouped in the appended Bibliography.

The dilated cardiomyopathies are a heterogeneous group of disorders with different inheritance patterns, including autosomal dominant (~23%), X-linked (~5%), autosomal recessive, and mitochondrial transmission (Bowles et al., 2000). Approximately 30% of all DCM is thought to be inherited, while 70% is sporadic (Bowles et al., 2000). It has been speculated that a high percentage of the sporadic cases are due to acquired disease, including myocarditis or coronary artery disease, but little specific supporting data for these etiologies are available.

DCM is common in patients with Duchenne Muscular Dystrophy (DMD), but it most frequently occurs late in the disease and it is a terminal event in about 10% of patients with DMD (Hunsaker et al., 1982; Perloff et al. 1966). In patients with Becker muscular dystrophy (BMD), cardiomyopathy can be an earlier and prominent feature. Some patients with identical mutations in the dystrophin gene may develop DCM while some do not. However, there is no good genotype to phenotype correlation in patients with DMD or BMD (Muntoni et al., 1993; Beggs et al., 1991; Gold et al., 1992). Variants of the dystrophin gene have been associated with X-linked DCM. The reports fall into two classes: i) mutations in the promoter region or exon 1 of the muscle transcript (Muntoni et al., 1993; Yoshida et al., 1998; Muntoni et al., 1995a; Muntoni et al., 1995b; Milasin et al., 1996) and, ii) mutations elsewhere in the gene (Ortiz-Lopez et al., 1997; Ferlini et al., 1998; Muntoni et al., 1997). The mutations within the promoter region and exon 1 of the major muscle transcript are associated with up-regulation of alternative dystrophin transcripts and the presence of brain and Purkinje cell dystrophin isoforms in skeletal muscle (Muntoni et al., 1995b). However, no dystrophin transcripts and protein are found in cardiac muscle in these patients.

Four mutations elsewhere in the gene have been described. An Alu-like sequence rearrangement has been found 2.4 kb into intron 11, resulting in activation of a cryptic splice site and producing an alternative transcript with numerous in frame stop codons (Ferlini et al., 1998). Only the mutant mRNA was detected in heart muscle, but some normal transcript also was found in skeletal muscle. Two deletions in the deletion hot spot region normally associated with BMD were described in two patients with dilated cardiomyopathy (Muntoni et al., 1997). Arbustini et al. (2000) found that four of 201 adult male patients (2%) with cardiomyopathy had deletions previously described in patients with BMD (Muntoni et al., 1993; Beggs et al., 1991; Gold et al., 1992) who did not have a previous diagnosis of muscular dystrophy. The reason that these patients did not have BMD is unclear. Finally a missense mutation was described in exon 9 (Ortiz-Lopez et al., 1997). The mutation was in an amino acid that is only moderately conserved (identical in mouse, dog and chicken, but not conserved in *Drosophila* dystrophin and in three utrophins). The significance of this one missense mutation is unknown since polymorphic missense mutations are common in the dystrophin gene (Mendell et al., 2001).

In view of the importance of early diagnosis of sporadic DCM, it is desired to identify genes associated with sporadic DCM for diagnostic and therapeutic purposes.

SUMMARY OF THE INVENTION

This invention provides the first evidence implicating specific mutations in the dystrophin gene with susceptibility to sporadic DCM.

In a first aspect of the invention, a method for detecting a susceptibility in an individual to sporadic DCM is provided. Thus, the present invention provides methods for determining whether a subject is at risk for developing sporadic DCM due to a mutation in the dystrophin gene. This method relies on the fact that mutations in the dystrophin gene have been correlated by the inventors with the disease. It will be understood by those of skill in the art, given the disclosure of the invention that such mutations are associated with a susceptability to sporadic DCM, that a variety of methods may be utilized to detect mutations in the dystrophin gene, including the mutations disclosed herein, which are associated with a susceptability to sporadic DCM.

The method can include detecting, in a tissue of the subject, the presence or absence of a polymorphism or alteration of the dystrophin gene. The detection of a polymorphism or alteration in the dystrophin gene may include ascertaining the existence of at least one of: a deletion of one or more nucleotides; an addition of one or more nucleotides, a substitution of one or more nucleotides; a gross chromosomal rearrangement; an alteration in the level of a messenger RNA transcript; the presence of a non-wild type splicing pattern of a messenger RNA transcript; a non-wild type level of an dystrophin protein; and/or an aberrant level of an dystrophin protein.

For example, detecting a polymorphism or alteration can include (i) providing a probe/primer comprised of an oligonucleotide which hybridizes to a sense or antisense sequence of an dystrophin gene or naturally occurring mutants thereof, or 5' or 3' flanking sequences naturally associated with an dystrophin gene; (ii) contacting the probe/primer to an appropriate nucleic acid containing sample; and (iii) detecting, by hybridization of the probe/primer to the nucleic acid, the presence or absence of the polymorphism or alteration; e.g. wherein detecting the polymorphism or alteration comprises utilizing the probe/primer to determine the nucleotide sequence of a dystrophin gene and, optionally, of the flanking nucleic acid sequences. For instance, the primer can be employed in a polymerase chain reaction (PCR), in a ligase chain reaction (LCR) or other amplification reactions known to a skilled artisan. In alternate embodiments, the level of a dystrophin protein is detected in an immunoassay using an antibody which is specifically immunoreactive with the dystrophin protein.

In a second aspect of the invention, compounds that are agonists or antagonists of a normal (functional) dystrophin bioactivity and their use in preventing or treating sporadic DCM are provided. For example, to ameliorate disease symptoms involving insufficient expression of a dystrophin gene and/or inadequate amount of functional dystrophin bioactivity in a subject, a gene therapeutic (comprising a gene encoding a functional dystrophin protein) or a protein therapeutic (comprising a functional dystrophin protein or fragment thereof) can be administered to the subject. Alternatively, agonists or antagonists of dystrophin function (wild-type or mutant) or an dystrophin receptor or a receptor for fragments of dystrophin can be administered.

In a third aspect of the invention, compounds that are antagonists of a disease causing dystrophin bioactivity and their use in preventing or treating sporadic DCM are provided. For example, to ameliorate disease symptoms involving expression of a mutant dystrophin gene or aberrant expression of a normal dystrophin gene in a subject, a therapeutically effective amount of an antisense, ribozyme or triple helix molecule to reduce or prevent gene expression may be administered to the subject. Alternatively, to ameliorate disease symptoms involving the regulation via a dystrophin protein or dystrophin protein fragments of an upstream or downstream element in a dystrophin mediated biochemical pathway (e.g. signal transduction), a therapeutically effective amount of an agonist or antagonist compound (e.g. small molecule, peptide, peptidomimetic, protein or antibody) that can prevent normal binding of the wildtype dystrophin protein, can induce a therapeutic effect.

In another aspect of the invention, assays, e.g., for screening test compounds to identify antagonists (e.g. inhibitors), or alternatively, agonists (e.g. potentiators), of an interaction between an dystrophin protein and, for example, a protein or nucleic acid that binds to the dystrophin protein or fragments of dystrophin are provided. An exemplary method includes the steps of (i) combining a dystrophin polypeptide or bioactive fragments thereof, an dystrophin target molecule (such as a dystrophin ligand or nucleic acid), and a test compound, e.g., under conditions wherein, but for the test compound, the dystrophin protein and dystrophin target molecule are able to interact; and (ii) detecting the formation of a complex which includes the dystrophin protein and the target molecule either by directly quantitating the complex or by measuring inductive effects of the dystrophin protein or fragments of dystrophin protein. A statistically significant change, such as a decrease, in the interaction of the dystrophin and dystrophin target molecule in the presence of a test compound (relative to what is detected in the absence of the test compound) is indicative of a modulation (e.g., inhibition or potentiation of the interaction between the dystrophin protein or fragments of the dystrophin protein and the target molecule).

In a further aspect of the present invention concerns methods for modulating the transcription of certain genes in a cell by modulating dystrophin bioactivity, (e.g., by potentiating or disrupting an dystrophin bioactivity). In general, whether carried out in vivo, in vitro, or in situ, the method comprises treating the cell with an effective amount of an dystrophin therapeutic (agonist or antagonist of a dystrophin bioactivity) so as to alter, relative to the cell in the absence of treatment, the level of transcription of certain genes. Accordingly, the method can be carried out with dystrophin therapeutics such as peptide and peptidomimetics or other molecules identified in the above-referenced drug screens which agonize or antagonize the effects of a dystrophin bioactivity (e.g. transcription) of a gene which is regulated by an dystrophin protein. Other dystrophin therapeutics include antisense constructs for inhibiting expression of dystrophin proteins, and dominant negative mutants of dystrophin proteins which competitively inhibit interactions between ligands (e.g. proteins) and nucleic acids upstream and downstream of the wild-type dystrophin protein.

BRIEF DESCRIPTION OF FIGURES

FIGS. 1A-1C show a molecular analysis of the dystrophin gene. Segment of one of the DOVAM-S gels showing the altered band is shown on the left and the sequence chromatogram is shown on the right. FIG. 1A: Splice junction mutation (G>T) at IVS5+1 of patient DCM-10. FIG. 1B: Missense mutation A7104C (T>G as complementary sequence) in exon 47 of patient DCM-33. The absence of two bands (*) is due to PCR failure in a different exon. Reamplification and sequencing of the missing exon showed a normal sequence. FIG. 1C: Missense mutation T9890C (A>G as complementary sequence) in exon 67 of patient DCM-51. Arrows indicate the band shift on DOVAM-S gels.

DETAILED DESCRIPTION OF THE INVENTION

The present invention is based in part on the discovery of alterations in the dystrophin gene which are linked to sporadic DCM. Based on this finding the invention provides therapeutic methods, compositions and diagnostics for sporadic DCM based on dystrophin.

The sequences for the coding sequence of the dystrophin gene and its various isoforms, the protein sequence of the various isoforms and the genomic sequences can be obtained at the website "dmd" dot "nl" by first accessing "DMD gene sequences" and then accessing "JdD01c" in the "Detailed Tabular Listing" which provides the genomic sequences which were utilized for designing DMD primers. The cDNA of the dystrophin gene is set forth in GenBank accession No. M18533 and in SEQ ID NO:1. SEQ ID NO:1 differs from M18533 by an A at position 7304 which was found more common in samples analyzed herein. The corresponding protein sequence is set forth in SEQ ID NO:2. The genomic sequences found at "JdD01c" are set forth in the Table A and were screened for alterations.

The present invention relates to dystrophin agonists and antagonists and their use in treating sporadic DCM. For example, (i) nucleic acid molecules encoding functional dystrophin protein; (ii) nucleic acids that are effective antisense, ribozyme and triplex antagonists of nucleic acids encoding functional dystrophin protein; (iii) functional dystrophin proteins or peptides; (iv) anti-dystrophin antibodies; (v) drugs affecting wild-type or mutant dystrophin function or dystrophin interaction with an dystrophin receptor and preparations of such compositions are disclosed herein. In addition, the invention provides drug discovery assays for identifying additional agents that agonize or antagonize the biological function of dystrophin protein (e.g. by altering the interaction of dystrophin molecules with either downstream or upstream elements in the biochemical (e.g. signal transduction) pathway). Moreover, the present invention provides assays for diagnosing whether a subject has or has a predisposition towards developing sporadic DCM.

Proof that any particular gene located within the genetically defined interval is a disease susceptibility locus is obtained by finding sequences in DNA or RNA extracted from affected kindred members which create abnormal gene products or abnormal levels of gene product. Such disease susceptibility alleles will co-segregate with the disease in large kindreds. They will also be present at a much higher frequency in non-kindred individuals with the disease than in individuals in the general population. In identifying a disease susceptibility locus, the key is to find polymorphisms, alterations or mutations which are serious enough to cause obvious disruption to the normal function of the gene product. These mutations can take a number of forms. The most severe forms would be frame shift mutations or large deletions which would cause the gene to code for an abnormal protein or one which would significantly alter protein expression. Less severe disruptive mutations would include small in-frame deletions and nonconservative base pair substitutions which would have a significant effect on the protein produced, such as changes to or from a cysteine residue, from a basic to an acidic amino acid or vice versa, from a hydrophobic to hydrophilic amino acid or vice versa, or other mutations which would affect secondary, tertiary or quaternary protein structure. Small deletions or base pair substitutions could also significantly alter protein expression by changing the level of transcription, splice pattern, mRNA stability, or translation efficiency of the gene transcript. Silent mutations or those resulting in conservative amino acid substitutions would not generally be expected to disrupt protein function. Causal mutations can also be found in the promoter of the gene. These mutations would interfere with the binding of regulatory factors and in this way alter transcription of the gene and therefore change the function of the gene.

In one aspect, the invention features probes and primers for use in a prognostic or diagnostic assay. For instance, the present invention also provides a probe/primer comprising a substantially purified oligonucleotide, which oligonucleotide comprises a region of nucleotide sequence that hybridizes under stringent conditions to at least approximately 12, preferably 25, more preferably 40, 50 or 75 consecutive nucleotides of sense or anti-sense sequence of dystrophin, including 5' and/or 3' untranslated regions. In preferred embodiments, the probe further comprises a label group attached thereto and able to be detected, e.g. the label group is selected from amongst radioisotopes, fluorescent compounds, enzymes, and enzyme co-factors.

In a further aspect, the present invention features methods for determining whether a subject is at risk for developing sporadic DCM. According to the diagnostic and prognostic methods of the present invention, alteration of the wild-type dystrophin locus is detected. "Alteration of a wild-type gene" encompasses all forms of mutations including deletions, insertions and point mutations in the coding and noncoding regions. Deletions may be of the entire gene or of only a portion of the gene. Point mutations may result in stop codons, frameshift mutations or amino acid substitutions. Point mutations or deletions in the promoter can change transcription and thereby alter the gene function. Somatic mutations are those which occur only in certain tissues and are not inherited in the germline. Germline mutations can be found in any of a body's tissues and are inherited. The finding of dystrophin germline mutations thus provides diagnostic information. An dystrophin allele which is not deleted (e.g., found on the sister chromosome to a chromosome carrying an dystrophin deletion) can be screened for other mutations, such as insertions, small deletions, and point mutations. Point mutational events may occur in regulatory regions, such as in the promoter of the gene, or in intron regions or at intron/exon junctions.

Useful diagnostic techniques include, but are not limited to fluorescent in situ hybridization (FISH), direct DNA sequencing, PFGE analysis, Southern blot analysis, single stranded conformation analysis (SSCA), RNase protection assay, allele-specific oligonucleotide (ASO), dot blot analysis and PCR-SSCP, as discussed in detail further below. Also useful is the recently developed technique of DNA microchip technology. In addition to the techniques described herein, similar and other useful techniques are also described in U.S. Pat. Nos. 5,837,492 and 5,800,998, each incorporated herein by reference.

Predisposition to disease can be ascertained by testing any tissue of a human for mutations of the dystrophin gene. For example, a person who has inherited a germline dystrophin mutation would be prone to develop sporadic DCM. This can be determined by testing DNA from any tissue of the person's body. Most simply, blood can be drawn and DNA extracted from the cells of the blood. In addition, prenatal diagnosis can be accomplished by testing fetal cells, placental cells or amniotic cells for mutations of the dystrophin gene. Alteration of a wild-type dystrophin allele, whether, for example, by point mutation or deletion, can be detected by any of the means discussed herein.

There are several methods that can be used to detect DNA sequence variation. Direct DNA sequencing, either manual sequencing or automated fluorescent sequencing can detect sequence variation. Another approach is the single-stranded conformation polymorphism assay (SSCA) (Orita et al., 1989). This method does not detect all sequence changes, especially if the DNA fragment size is greater than 200 bp, but can be optimized to detect most DNA sequence variation. The reduced detection sensitivity is a disadvantage, but the increased throughput possible with SSCA makes it an attractive, viable alternative to direct sequencing for mutation detection on a research basis. The fragments which have shifted mobility on SSCA gels are then sequenced to determine the exact nature of the DNA sequence variation. Other approaches based on the detection of mismatches between the two complementary DNA strands include clamped denaturing gel electrophoresis (CDGE) (Sheffield et al., 1991), heteroduplex analysis (HA) (White et al., 1992) and chemical mismatch cleavage (CMC) (Grompe et al., 1989). None of the methods described above will detect large deletions, duplications or insertions, nor will they detect a regulatory mutation which affects transcription or translation of the protein. Other methods which might detect these classes of mutations such as a protein truncation assay or the asymmetric assay, detect only specific types of mutations and would not detect missense mutations. A review of currently available methods of detecting DNA sequence variation can be found in a recent review by Grompe (1993). Once a mutation is known, an allele specific detection approach such as allele specific oligonucleotide (ASO) hybridization can be utilized to rapidly screen large numbers of other samples for that same mutation.

Detection of point mutations may be accomplished by molecular cloning of the dystrophin allele(s) and sequencing the allele(s) using techniques well known in the art. Alternatively, the gene sequences can be amplified directly from a genomic DNA preparation from the tissue, using known techniques. The DNA sequence of the amplified sequences can then be determined.

There are six well known methods for a more complete, yet still indirect, test for confirming the presence of a susceptibility allele: 1) single-stranded conformation analysis (SSCA) (Orita et al., 1989); 2) denaturing gradient gel electrophoresis (DGGE) (Wartell et al., 1990; Sheffield et al., 1989); 3) RNase protection assays (Finkelstein et al., 1990; Kinszler et al., 1991); 4) allele-specific oligonucleotides (ASOs) (Conner et al., 1983); 5) the use of proteins which recognize nucleotide mismatches, such as the E. coli mutS protein (Modrich, 1991); and 6) allele-specific PCR (Rano and Kidd, 1989). For allele-specific PCR, primers are used which hybridize at their 3' ends to a particular dystrophin mutation. If the particular dystrophin mutation is not present, an amplification product is not observed. Amplification Refractory Mutation System (ARMS) can also be used, as disclosed in European Patent Application Publication No. 0332435 and in Newton et al., 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening relatives of an affected individual for the presence of the dystrophin mutation found in that individual. Other techniques for detecting insertions and deletions as known in the art can be used.

In the first three methods (SSCA, DGGE and RNase protection assay), a new electrophoretic band appears. SSCA detects a band which migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or in its mRNA product. While these techniques are less sensitive than sequencing, they are simpler to perform on a large number of tumor samples. An example of a mismatch cleavage technique is the RNase protection method. In the practice of the present invention, the method involves the use of a labeled riboprobe which is complementary to the human wild-type dystrophin gene coding sequence. The riboprobe and either mRNA or DNA isolated from the tumor tissue are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the dystrophin mRNA or gene but can be a segment of either. If the riboprobe comprises only a segment of the dystrophin mRNA or gene, it will be desirable to use a number of these probes to screen the whole mRNA sequence for mismatches.

In similar fashion, DNA probes can be used to detect mismatches, through enzymatic or chemical cleavage. See, e.g., Cotton et al., 1988; Shenk et al., 1975; Novack et al., 1986. Alternatively, mismatches can be detected by shifts in the electrophoretic mobility of mismatched duplexes relative to matched duplexes. See, e.g., Cariello, 1988. With either riboprobes or DNA probes, the cellular mRNA or DNA which might contain a mutation can be amplified using PCR before hybridization. Changes in DNA of the dystrophin gene can also be detected using Southern hybridization, especially if the changes are gross rearrangements, such as deletions and insertions.

DNA sequences of the dystrophin gene which have been amplified by use of PCR may also be screened using allele-specific probes. These probes are nucleic acid oligomers, each of which contains a region of the dystrophin gene sequence harboring a known mutation. For example, one oligomer may be about 30 nucleotides in length (although shorter and longer oligomers are also usable as well recognized by those of skill in the art), corresponding to a portion of the dystrophin gene sequence. By use of a battery of such allele-specific probes, PCR amplification products can be screened to identify the presence of a previously identified mutation in the dystrophin gene. Hybridization of allele-specific probes with amplified dystrophin sequences can be performed, for example, on a nylon filter. Hybridization to a particular probe under high stringency hybridization conditions indicates the presence of the same mutation in the tumor tissue as in the allele-specific probe.

The newly developed technique of nucleic acid analysis via microchip technology is also applicable to the present invention. In this technique, literally thousands of distinct oligonucleotide probes are built up in an array on a silicon chip. Nucleic acid to be analyzed is fluorescently labeled and hybridized to the probes on the chip. It is also possible to study nucleic acid-protein interactions using these nucleic acid microchips. Using this technique one can determine the presence of mutations or even sequence the nucleic acid being analyzed or one can measure expression levels of a gene of interest. The method is one of parallel processing of many, even thousands, of probes at once and can tremendously increase the rate of analysis. Several papers have been published which use this technique. Some of these are Hacia et al., 1996; Shoemaker et al., 1996; Chee et al., 1996; Lockhart et al., 1996; DeRisi et al., 1996; Lipshutz et al., 1995. This method has already been used to screen people for mutations in the breast cancer gene BRCA1 (Hacia et al., 1996). This new technology has been reviewed in a news article in Chemical and Engineering News (Borman, 1996) and been the subject of an editorial (Nature Genetics, 1996). Also see Fodor (1997).

The most definitive test for mutations in a candidate locus is to directly compare genomic dystrophin sequences from disease patients with those from a control population. Alternatively, one could sequence messenger RNA after amplification, e.g., by PCR, thereby eliminating the necessity of determining the exon structure of the candidate gene.

Mutations from disease patients falling outside the coding region of dystrophin can be detected by examining the non-coding regions, such as introns and regulatory sequences near or within the dystrophin gene. An early indication that mutations in noncoding regions are important may come from Northern blot experiments that reveal messenger RNA molecules of abnormal size or abundance in disease patients as compared to control individuals.

Alteration of dystrophin mRNA expression can be detected by any techniques known in the art. These include Northern blot analysis, PCR amplification and RNase protection. Diminished or increased mRNA expression indicates an alteration of the wild-type dystrophin gene. Alteration of wild-type dystrophin genes can also be detected by screening for alteration of wild-type dystrophin protein. For example, monoclonal antibodies immunoreactive with dystrophin can be used to screen a tissue. Lack of cognate antigen would indicate an dystrophin mutation. Antibodies specific for products of mutant alleles could also be used to detect mutant dystrophin gene product. Such immunological assays can be done in any convenient formats known in the art. These include Western blots, immunohistochemical assays and ELISA assays. Any means for detecting an altered dystrophin protein can be used to detect alteration of wild-type dystrophin genes. Functional assays, such as protein binding determinations, can be used. In addition, assays can be used which detect dystrophin biochemical function. Finding a mutant dystrophin gene product indicates alteration of a wild-type dystrophin gene.

The primer pairs of the present invention are useful for determination of the nucleotide sequence of a particular dystrophin allele using PCR. The pairs of single-stranded DNA primers can be annealed to sequences within or surrounding the dystrophin gene on chromosome 12 in order to prime amplifying DNA synthesis of the dystrophin gene itself. A complete set of these primers allows synthesis of all of the nucleotides of the dystrophin gene coding sequences, i.e., the exons. The set of primers preferably allows synthesis of both intron and exon sequences. Allele-specific primers can also be used. Such primers anneal only to particular dystrophin mutant alleles, and thus will only amplify a product in the presence of the mutant allele as a template.

In order to facilitate subsequent cloning of amplified sequences, primers may have restriction enzyme site sequences appended to their 5' ends. Thus, all nucleotides of the primers are derived from dystrophin sequences or sequences adjacent to dystrophin, except for the few nucleotides necessary to form a restriction enzyme site. Such enzymes and sites are well known in the art. The primers themselves can be synthesized using techniques which are well known in the art. Generally, the primers can be made using oligonucleotide synthesizing machines which are commercially available. Given the known sequences of the dystrophin exons and the 5' alternate exon, the design of particular primers is well within the skill of the art. Suitable primers for mutation screening are also described herein.

The nucleic acid probes provided by the present invention are useful for a number of purposes. They can be used in Southern hybridization to genomic DNA and in the RNase protection method for detecting point mutations already discussed above. The probes can be used to detect PCR amplification products. They may also be used to detect mismatches with the dystrophin gene or mRNA using other techniques.

It has been discovered that individuals with the wild-type dystrophin gene do not have sporadic DCM which results from the dystrophin allele. However, mutations which interfere with the function of the dystrophin protein are involved in the susceptibility to sporadic DCM as shown herein. Thus, the presence of an altered (or a mutant) dystrophin gene which produces a protein having a loss of function, or altered function, directly correlates to an increased risk of disease. In order to detect an dystrophin gene mutation, a biological sample is prepared and analyzed for a difference between the sequence of the dystrophin allele being analyzed and the sequence of the wild-type dystrophin allele. Mutant dystrophin alleles can be initially identified by any of the techniques described above. The mutant alleles are then sequenced to identify the specific mutation of the particular mutant allele. Alternatively, mutant dystrophin alleles can be initially identified by identifying mutant (altered) dystrophin proteins, using conventional techniques. The mutant alleles are then sequenced to identify the specific mutation for each allele. The mutations, especially those which lead to an altered function of the dystrophin protein, are then used for the diagnostic methods of the present invention.

The present invention employs definitions commonly used in the art with specific reference to the gene described in the present application. Such definitions can be found in U.S. Pat. Nos. 5,837,492; 5,800,998; 6,261,801; 6,274,720 and 6,274,376, each incorporated herein by reference. Such definitions are employed herein unless the context indicates otherwise.

Nucleic Acids and Proteins

A nucleic acid or fragment thereof has (substantial identity with another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95-98% of the nucleotide bases. A protein or fragment thereof has substantial identity with another if, optimally aligned, there is an amino acid sequence identity of at least about 30% identity with an entire naturally-occurring protein or a portion thereof, usually at least about 70% identity, more usually at least about 80% identity, preferably at least about 90% identity, and more preferably at least about 95% identity, and most preferably at least 98% identity.

Identity means the degree of sequence relatedness between two polypeptide or two polynucleotides sequences as determined by the identity of the match between two strings of such sequences, such as the full and complete sequence. Identity can be readily calculated. While there exist a number of methods to measure identity between two polynucleotide or polypeptide sequences, the term "identity" is well known to skilled artisans (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). Methods commonly employed to determine identity between two sequences include, but are not limited to those disclosed in *Guide to Huge Computers*, Martin J. Bishop, ed., Academic Press, San Diego, 1994, and Carillo, H., and Lipman, D., *SIAM J Applied Math*. 48:1073 (1988). Preferred methods to determine identity are designed to give the largest match between the two sequences tested. Such methods are codified in computer programs. Preferred computer program methods to determine identity between two sequences include, but are not limited to, GCG (Genetics Computer Group, Madison Wis.) program package (Devereux, J., et al., *Nucleic Acids Research* 12:387 (1984)), BLASTP, BLASTN, FASTA (Altschul et al., 1990; Altschul et al., 1997). The well-known Smith Waterman algorithm may also be used to determine identity.

As an illustration, by a polynucleotide having a nucleotide sequence having at least, for example, 95% "identity" to a reference nucleotide sequence it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5 or 3 terminal positions of the reference nucleotide sequence or anywhere between those terminal positions, interspersed either individually among nucleotides in the reference sequence or in one or more contiguous groups within the reference sequence.

Alternatively, substantial homology or (similarity) exists when a nucleic acid or fragment thereof will hybridize to another nucleic acid (or a complementary strand thereof) under selective hybridization conditions, to a strand, or to its complement. Selectivity of hybridization exists when hybridization which is substantially more selective than total lack of specificity occurs. Typically, selective hybridization will occur when there is at least about 55% homology over a stretch of at least about 14 nucleotides, preferably at least about 65%, more preferably at least about 75%, and most preferably at least about 90%. The length of homology comparison, as described, may be over longer stretches, and in certain embodiments will often be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1000 mM, typically less than 500 mM, and preferably less than 200 mM. However, the combination of parameters is much more important than the measure of any single parameter. The stringency conditions are dependent on the length of the nucleic acid and the base composition of the nucleic acid, and can be determined by techniques well known in the art. See, e.g., Ausubel, 1992; Wetmur and Davidson, 1968.

Thus, as herein used, the term "stringent conditions" means hybridization will occur only if there is at least 95% and preferably at least 97% identity between the sequences. Such hybridization techniques are well known to those of skill in the art. Stringent hybridization conditions are as defined above or, alternatively, conditions under overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 µg/ml denatured, sheared salmon sperm DNA, followed by washing the filters in 0.1×SSC at about 65° C.

The terms "isolated", "substantially pure", and "substantially homogeneous" are used interchangeably to describe a protein or polypeptide which has been separated from components which accompany it in its natural state. A monomeric protein is substantially pure when at least about 60 to 75% of a sample exhibits a single polypeptide sequence. A substantially pure protein will typically comprise about 60 to 90% W/W of a protein sample, more usually about 95%, and preferably will be over about 99% pure. Protein purity or homogeneity may be indicated by a number of means well known in the art, such as polyacrylamide gel electrophoresis of a protein sample, followed by visualizing a single polypeptide band upon staining the gel. For certain purposes, higher resolution may be provided by using HPLC or other means well known in the art which are utilized for purification.

Large amounts of the nucleic acids of the present invention may be produced by (a) replication in a suitable host or transgenic animals or (b) chemical synthesis using techniques well known in the art. Constructs prepared for introduction into a prokaryotic or eukaryotic host may comprise a replication system recognized by the host, including the intended polynucleotide fragment encoding the desired polypeptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Secretion signals may also be included where appropriate which allow the protein to cross and/or lodge in cell membranes, and thus attain its functional topology, or be secreted from the cell. Such vectors may be prepared by means of standard recombinant techniques well known in the art.

Methods of Use: Nucleic Acid Diagnosis and Diagnostic Kits

In order to detect the presence of a dystrophin allele predisposing an individual to sporadic DCM, a biological sample such as blood is prepared and analyzed for the presence or absence of predisposing alleles of dystrophin. Results of these tests and interpretive information are returned to the health care provider for communication to the tested individual. Such diagnoses may be performed by diagnostic laboratories, or, alternatively, diagnostic kits are manufactured and sold to health care providers or to private individuals for self-diagnosis. Diagnositic or prognostic tests can be performed as described herein or using well known techniques, such as described in U.S. Pat. No. 5,800,998, incorporated herein by reference.

Initially, the screening method involves amplification of the relevant dystrophin sequences. In another preferred embodiment of the invention, the screening method involves a non-PCR based strategy. Such screening methods include two-step label amplification methodologies that are well known in the art. Both PCR and non-PCR based screening strategies can detect target sequences with a high level of sensitivity.

The most popular method used today is target amplification. Here, the target nucleic acid sequence is amplified with polymerases. One particularly preferred method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

When the probes are used to detect the presence of the target sequences (for example, in screening for sporadic DCM susceptibility), the biological sample to be analyzed, such as blood or serum, may be treated, if desired, to extract the nucleic acids. The sample nucleic acid may be prepared in various ways to facilitate detection of the target sequence; e.g. denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Analyte nucleic acid and probe are incubated under conditions which promote stable hybrid formation of the target sequence in the probe with the putative targeted sequence in the analyte. The region of the probes which is used to bind to the analyte can be made completely complementary to the targeted region of human chromosome 1. Therefore, high stringency conditions are desirable in order to prevent false positives. However, conditions of high stringency are used only if the probes are complementary to regions of the chromosome which are unique in the genome. The stringency of hybridization is determined by a number of factors during hybridization and during the washing procedure, including temperature, ionic strength, base composition, probe length, and concentration of formamide. These factors are outlined in, for example, Maniatis et al., 1982 and Sambrook et al., 1989. Under certain circumstances, the formation of higher order hybrids, such as triplexes, quadraplexes, etc., may be desired to provide the means of detecting target sequences.

Detection, if any, of the resulting hybrid is usually accomplished by the use of labeled probes. Alternatively, the probe may be unlabeled, but may be detectable by specific binding with a ligand which is labeled, either directly or indirectly. Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies and the like. Variations of this basic scheme are known in the art, and include those variations that facilitate separation of the hybrids to be detected from extraneous materials and/or that amplify the signal from the labeled moiety. A number of these variations are reviewed in, e.g., Matthews and Kricka, 1988; Landegren et al., 1988; Mittlin, 1989; U.S. Pat. No. 4,868, 105, and in EPO Publication No. 225,807.

As noted above, non-PCR based screening assays are also contemplated in this invention. This procedure hybridizes a nucleic acid probe (or an analog such as a methyl phosphonate backbone replacing the normal phosphodiester), to the low level DNA target. This probe may have an enzyme covalently linked to the probe, such that the covalent linkage does not interfere with the specificity of the hybridization. This enzyme-probe-conjugate-target nucleic acid complex can then be isolated away from the free probe enzyme conjugate and a substrate is added for enzyme detection. Enzymatic activity is observed as a change in color development or luminescent output resulting in a $10^3$-$10^6$ increase in sensitivity. For an example relating to the preparation of oligodeoxynucleotide-alkaline phosphatase conjugates and their use as hybridization probes see Jablonski et al., 1986.

Two-step label amplification methodologies are known in the art. These assays work on the principle that a small ligand (such as digoxigenin, biotin, or the like) is attached to a nucleic acid probe capable of specifically binding dystrophin. Allele specific probes are also contemplated within the scope of this example and exemplary allele specific probes include probes encompassing the predisposing or potentially predisposing mutations summarized in herein.

In one example, the small ligand attached to the nucleic acid probe is specifically recognized by an antibody-enzyme conjugate. In one embodiment of this example, digoxigenin is attached to the nucleic acid probe. Hybridization is detected by an antibody-alkaline phosphatase conjugate which turns over a chemiluminescent substrate. For methods for labeling nucleic acid probes according to this embodiment see Martin et al., 1990. In a second example, the small ligand is recognized by a second ligand-enzyme conjugate that is capable of specifically complexing to the first ligand. A well known embodiment of this example is the biotin-avidin type of interactions. For methods for labeling nucleic acid probes and their use in biotin-avidin based assays see Rigby et al., 1977 and Nguyen et al., 1992.

It is also contemplated within the scope of this invention that the nucleic acid probe assays of this invention will employ a cocktail of nucleic acid probes capable of detecting dystrophin. Thus, in one example to detect the presence of dystrophin in a cell sample, more than one probe complementary to dystrophin is employed and in particular the number of different probes is alternatively 2, 3, or 5 different nucleic acid probe sequences. In another example, to detect the presence of mutations in the dystrophin gene sequence in a patient, more than one probe complementary to dystrophin is employed where the cocktail includes probes capable of binding to the allele-specific mutations identified in populations of patients with alterations in dystrophin. In this embodiment, any number of probes can be used, and will preferably include probes corresponding to the major gene mutations identified as predisposing an individual to sporadic DCM. Some candidate probes contemplated within the scope of the invention include probes that include the allele-specific mutations identified herein and those that have the dystrophin regions corresponding to SEQ ID NOs:1-5 and 8 both 5' and 3' to the mutation site.

Methods of Use: Peptide Diagnosis and Diagnostic Kits

Susceptibility to DCM can also be detected on the basis of the alteration of wild-type dystrophin polypeptide. Peptide diagnostic or prognostic tests can be performed as described herein or using well known techniques, such as described in U.S. Pat. No. 5,800,998, incorporated herein by reference. For example, such alterations can be determined by sequence analysis in accordance with conventional techniques. More preferably, antibodies (polyclonal or monoclonal) are used to detect differences in, or the absence of, dystrophin peptides. The antibodies may be prepared in accordance with conventional techniques. Other techniques for raising and purifying antibodies are well known in the art and any such techniques may be chosen to achieve the preparations claimed in this invention. In a preferred embodiment of the invention, antibodies will immunoprecipitate dystrophin proteins or fragments of the dystrophin protein from solution as well as react with dystrophin peptides on Western or immunoblots of polyacrylamide gels. In another preferred embodiment, antibodies will detect dystrophin proteins and protein fragments in paraffin or frozen tissue sections, using immunocytochemical techniques.

Preferred embodiments relating to methods for detecting dystrophin or its mutations include enzyme linked immunosorbent assays (ELISA), radioimmunoassays (RIA), immunoradiometric assays (IRMA) and immunoenzymatic assays (IEMA), including sandwich assays using monoclonal and/or polyclonal antibodies. Exemplary sandwich assays are described by David et al. in U.S. Pat. Nos. 4,376,110 and 4,486,530, hereby incorporated by reference.

Methods of Use: Drug Screening

Polypeptides of the invention also may be used to assess the binding of small molecule substrates and ligands in, for example, cells, cell-free preparations, chemical libraries, and natural product mixtures. These substrates and ligands may be natural substrates and ligands or may be structural or functional mimetics. See, e.g., Coligan et al., Current Protocols in Immunology 1(2):Chapter 5 (1991). Thus, the invention also provides a method of screening compounds to identify those which enhance (agonist) or block (antagonist) the action of dystrophin polypeptides or polynucleotides, particularly those compounds for treating or preventing sporadic DCM.

This invention is particularly useful for screening compounds by using a wild-type or mutant dystrophin polypeptide or binding fragment thereof in any of a variety of drug screening techniques. Drug screening can be performed as described herein or using well known techniques, such as described in U.S. Pat. Nos. 5,800,998 and 5,891,628, each incorporated herein by reference.

The dystrophin polypeptide or fragment employed in such a test may either be free in solution, affixed to a solid support, or borne on a cell surface. One method of drug screening utilizes eucaryotic or procaryotic host cells which are stably transformed with recombinant polynucleotides expressing the polypeptide or fragment, preferably in competitive binding assays. Such cells, either in viable or fixed form, can be used for standard binding assays. One may measure, for example, for the formation of complexes between an dystrophin polypeptide or fragment and the agent being tested, or examine the degree to which the formation of a complex between an dystrophin polypeptide or fragment and a ligand is interfered with by the agent being tested.

Thus, the present invention provides methods of screening for drugs comprising contacting such an agent with an dystrophin polypeptide or fragment thereof and assaying (i) for the presence of a complex between the agent and the dystrophin polypeptide or fragment, or (ii) for the presence of a complex between the dystrophin polypeptide or fragment and a ligand, by methods well known in the art. In such competitive binding assays the dystrophin polypeptide or fragment is typically labeled. Free dystrophin polypeptide or fragment is separated from that present in a protein:protein complex, and the amount of free (i.e:, uncomplexed) label is a measure of the binding of the agent being tested to dystrophin or its interference with dystrophin:ligand binding, respectively.

Another technique for drug screening provides high throughput screening for compounds having suitable binding affinity to the dystrophin polypeptides and is described in detail in Geysen, PCT published application WO 84/03564, published on Sep. 13, 1984. Briefly stated, large numbers of different small peptide test compounds are synthesized on a solid substrate, such as plastic pins or some other surface. The peptide test compounds are reacted with dystrophin polypeptides and washed. Bound dystrophin polypeptides are then detected by methods well known in the art.

Purified dystrophin can be coated directly onto plates for use in the aforementioned drug screening techniques. However, non-neutralizing antibodies to the polypeptide can be used to capture antibodies to immobilize the dystrophin polypeptide on the solid phase.

This invention also contemplates the use of competitive drug screening assays in which neutralizing antibodies capable of specifically binding the dystrophin polypeptide compete with a test compound for binding to the dystrophin polypeptide or fragments thereof. In this manner, the antibodies can be used to detect the presence of any peptide which shares one or more antigenic determinants of the dystrophin polypeptide.

A further technique for drug screening involves the use of host eukaryotic cell lines or cells (such as described above) which express a wild-type or mutant dystrophin gene and as a consequence of expression of wild type or mutant dystrophin demonstrate a specific phenotype. The phenotype of the cells is examined to determine if the compound is capable of modulating the phenotype and thereby dystrophin function.

Briefly, a method of screening for a substance which modulates activity of a polypeptide may include contacting one or more test substances with the polypeptide in a suitable reaction medium, testing the activity of the treated polypeptide and comparing that activity with the activity of the polypeptide in comparable reaction medium untreated with the test substance or substances. A difference in activity between the treated and untreated polypeptides is indicative of a modulating effect of the relevant test substance or substances.

Prior to or as well as being screened for modulation of activity, test substances may be screened for ability to interact with the polypeptide, e.g., in a yeast two-hybrid system (e.g., Bartel et al., 1993; Fields and Song, 1989; Chevray and Nathans, 1992; Lee et al., 1995). This system may be used as a coarse screen prior to testing a substance for actual ability to modulate activity of the polypeptide. Alternatively, the screen could be used to screen test substances for binding to an dystrophin specific binding partner, or to find mimetics of an dystrophin polypeptide.

Methods of Use: Rational Drug Design

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, 1991. Rational drug design can be performed as described herein or using well known techniques, such as described in U.S. Pat. Nos. 5,800, 998 and 5,891,628, each incorporated herein by reference.

In one approach, one first determines the three-dimensional structure of a protein of interest (e.g., dystrophin polypeptide or fragments of the dystrophin polypeptide) or, for example, of the dystrophin-ligand complex, by x-ray crystallography, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., 1990). In addition, peptides (e.g., dystrophin polypeptide or fragments thereof) are analyzed by an alanine scan (Wells, 1991). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced banks of peptides. Selected peptides would then act as the pharmacore. Thus, one may design drugs which have, e.g., improved dystrophin polypeptide activity or stability or which act as inhibitors, agonists, antagonists, etc. of dystrophin polypeptide activity.

Following identification of a substance which modulates or affects polypeptide activity, the substance may be investigated further. Furthermore, it may be manufactured and/or used in preparation, i.e., manufacture or formulation, or a composition such as a medicament, pharmaceutical composition or drug. These may be administered to individuals.

Thus, the present invention extends in various aspects not only to a substance identified using a nucleic acid molecule as a modulator of polypeptide activity, in accordance with what is disclosed herein, but also a pharmaceutical composition, medicament, drug or other composition comprising such a substance, a method comprising administration of such a composition comprising such a substance, a method comprising administration of such a composition to a patient, e.g., for treatment or prophylaxis of sporadic DCM, use of such a substance in the manufacture of a composition for administration, e.g., for treatment or prophylaxis of sporadic DCM, and a method of making a pharmaceutical composition comprising admixing such a substance with a pharmaceutically acceptable excipient, vehicle or carrier, and optionally other ingredients.

A substance identified as a modulator of polypeptide function may be peptide or non-peptide in nature. Non-peptide "small molecules" are often preferred for many in vivo pharmaceutical uses. Accordingly, a mimetic or mimic of the substance (particularly if a peptide) may be designed for pharmaceutical use.

The designing of mimetics to a known pharmaceutically active compound is a known approach to the development of pharmaceuticals based on a "lead" compound. This might be desirable where the active compound is difficult or expensive to synthesize or where it is unsuitable for a particular method of administration, e.g., pure peptides are unsuitable active agents for oral compositions as they tend to be quickly degraded by proteases in the alimentary canal. Mimetic design, synthesis and testing is generally used to avoid randomly screening large numbers of molecules for a target property.

There are several steps commonly taken in the design of a mimetic from a compound having a given target property. First, the particular parts of the compound that are critical and/or important in determining the target property are determined. In the case of a peptide, this can be done by systematically varying the amino acid residues in the peptide, e.g., by substituting each residue in turn. Alanine scans of peptide are commonly used to refine such peptide motifs. These parts or residues constituting the active region of the compound are known as its "pharmacophore".

Once the pharmacophore has been found, its structure is modeled according to its physical properties, e.g., stereochemistry, bonding, size and/or charge, using data from a range of sources, e.g., spectroscopic techniques, x-ray diffraction data and NMR. Computational analysis, similarity mapping (which models the charge and/or volume of a pharmacophore, rather than the bonding between atoms) and other techniques can be used in this modeling process.

In a variant of this approach, the three-dimensional structure of the ligand and its binding partner are modeled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted onto it can conveniently be selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent they exhibit it. Further optimization or modification can then be carried out to arrive at one or more final mimetics for in vivo or clinical testing.

Methods of Use: Nucleic Acid Based Therapies

According to the present invention, a method is also provided of supplying wild-type dystrophin function to a cell which carries mutant dystrophin alleles. The wild-type dystrophin gene or a part of the gene may be introduced into the cell in a vector such that the gene remains extrachromosomal. In such a situation, the gene will be expressed by the cell from the extrachromosomal location. If a gene fragment is introduced and expressed in a cell carrying a mutant dystrophin allele, the gene fragment should encode a part of the dystrophin protein which is required for normal physiological processes of the cell. More preferred is the situation where the wild-type dystrophin gene or a part thereof is introduced into the mutant cell in such a way that it recombines with the endogenous mutant dystrophin gene present in the cell. Such recombination requires a double recombination event which results in the correction of the dystrophin gene mutation. Vectors for introduction of genes both for recombination and for extrachromosomal maintenance are known in the art, and any suitable vector may be used. Methods for introducing DNA into cells such as electroporation, calcium, phosphate coprecipitation and viral transduction are known in the art, and the choice of method is within the competence of the routineer. See also U.S. Pat. Nos. 5,800,998 and 5,891,628, each incorporated by reference herein.

Among the compounds which may exhibit anti-sporadic DCM activity are antisense, ribozyme, and triple helix molecules. Such molecules may be designed to reduce or inhibit mutant dystrophin activity. Techniques for the production and use of such molecules are well known to those of skill in the art, such as described herein or in U.S. Pat. No. 5,800,998, incorporated herein by reference.

Antisense RNA and DNA molecules act to directly block the translation of mRNA by binding to targeted mRNA and preventing protein translation. With respect to antisense DNA, oligodeoxyribonucleotides derived from the translation initiation site, e.g., between the −10 and +10 regions of the dystrophin nucleotide sequence of interest, are preferred.

Ribozymes are enzymatic RNA molecules capable of catalyzing the specific cleavage of RNA. The mechanism of ribozyme action involves sequence specific hybridization of the ribozyme molecule to complementary target RNA, followed by a endonucleolytic cleavage. The composition of ribozyme molecules must include one or more sequences complementary to the target dystrophin mRNA, preferably the mutant dystrophin mRNA, and must include the well known catalytic sequence responsible for mRNA cleavage.

For this sequence, see U.S. Pat. No. 5,093,246, which is incorporated by reference herein in its entirety. As such, within the scope of the invention are engineered hammerhead motif ribozyme molecules that specifically and efficiently catalyze endonucleolytic cleavage of RNA sequences encoding dystrophin, preferably mutant dystrophin proteins.

Specific ribozyme cleavage sites within any potential RNA target are initially identified by scanning the target molecule for ribozyme cleavage sites which include the following sequence: GUA, GUU and GUC. Once identified, short RNA sequences of between 15 and ribonucleotides corresponding to the region of the target gene containing the cleavage site may be evaluated for predicted structural features, such as secondary structure, that may render the oligonucleotide sequence unsuitable. The suitability of candidate targets may also be evaluated by testing their accessibility to hybridization with complementary oligonucleotides, using ribonuclease protection assays.

Nucleic acid molecules to be used in triplex helix formation should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC.sup.+ triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, contain a stretch of guanidine residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with one strand of a duplex first and then the other, eliminating the necessity for a sizeable stretch of either purines or pyrimidines to be present on one strand of a duplex.

It is possible that the antisense, ribozyme, and/or triple helix molecules described herein may reduce or inhibit the translation of mRNA produced by both normal and mutant dystrophin alleles. In order to ensure that substantial normal levels of dystrophin activity are maintained in the cell, nucleic acid molecules that encode and express dystrophin polypeptides exhibiting normal dystrophin activity may be introduced into cells which do not contain sequences susceptible to whatever antisense, ribozyme, or triple helix treatments. Such sequences may be introduced via gene therapy methods. Alternatively, it may be preferable to coadminister normal dystrophin protein into the cell or tissue in order to maintain the requisite level of cellular or tissue dystrophin activity.

Antisense RNA and DNA molecules, ribozyme molecules and triple helix molecules of the invention may be prepared by any method known in the art for the synthesis of DNA and RNA molecules. These include techniques for chemically synthesizing oligodeoxyribo-nucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various well-known modifications to the DNA molecules may be introduced as a means of increasing intracellular stability and half-life. Possible modifications include, but are not limited to, the addition of flanking sequences of ribo- or deoxy-nucleotides to the 5 and/or 3' ends of the molecule or the use of phosphorothioate or 2' O-methyl rather than phosphodiesterase linkages within the oligodeoxyribonucleotide backbone.

Gene therapy would be carried out according to generally accepted methods, for example, as described in further detail in U.S. Pat. Nos. 5,837,492 and 5,800,998 and references cited therein, all incorporated by reference herein. Expression vectors in the context of gene therapy are meant to include those constructs containing sequences sufficient to express a polynucleotide that has been cloned therein. In viral expression vectors, the construct contains viral sequences sufficient to support packaging of the construct. If the polynucleotide encodes an antisense polynucleotide or a ribozyme, expression will produce the antisense polynucleotide or ribozyme. Thus in this context, expression does not require that a protein product be synthesized. In addition to the polynucleotide cloned into the expression vector, the vector also contains a promoter functional in eukaryotic cells. The cloned polynucleotide sequence is under control of this promoter. Suitable eukaryotic promoters include those described above. The expression vector may also include sequences, such as selectable markers and other sequences conventionally used.

Methods of Use: Peptide Therapy

Peptides which have dystrophin activity can be supplied to cells which carry mutant or missing dystrophin alleles. Peptide therapy is performed as described herein or using well known techniques, such as described in U.S. Pat. Nos. 5,800,998 and 5,891,628, each incorporated herein by reference.

Protein can be produced by expression of the cDNA sequence in bacteria, for example, using known expression vectors. Alternatively, dystrophin polypeptide can be extracted from dystrophin-producing mammalian cells. In addition, the techniques of synthetic chemistry can be employed to synthesize dystrophin protein. Any of such techniques can provide the preparation of the present invention which comprises the dystrophin protein. Preparation is substantially free of other human proteins. This is most readily accomplished by synthesis in a microorganism or in vitro.

Active dystrophin molecules can be introduced into cells by microinjection or by use of liposomes, for example. Alternatively, some active molecules may be taken up by cells, actively or by diffusion. Extracellular application of the dystrophin gene product may be sufficient to affect the development and or progression of sporadic DCM. Supply of molecules with dystrophin activity should lead to partial reversal of the DCM phenotype. Other molecules with dystrophin activity (for example, peptides, drugs or organic compounds) may also be used to effect such a reversal. Modified polypeptides having substantially similar function are also used for peptide therapy.

Alternatively, antibodies that are both specific for mutant dystrophin gene product and interfere with its activity may be used. Such antibodies may be generated using standard techniques described herein or using conventional techniques, such as described in U.S. Pat. Nos. 5,837,492; 5,800,998 and 5,891,628, against the proteins themselves or against peptides corresponding to the binding domains of the proteins. Such antibodies include but are not limited to polyclonal, monoclonal, Fab fragments, F(ab').sub.2 fragments, single chain antibodies, chimeric antibodies, humanized antibodies etc.

Methods of Use: Transformed Hosts; Transgenic/Knockout Animals and Models

Similarly, cells and animals which carry a mutant dystrophin allele can be used as model systems to study and test for substances which have potential as therapeutic agents. These may be isolated from individuals with dystrophin mutations, either somatic or germline. Alternatively, the cell line can be engineered to carry the mutation in the dystrophin allele, as described above. After a test substance is applied to the cells, the phenotype of the cell is determined. Any trait of the transformed cells can be assessed using techniques well known in the art. Transformed hosts, transgenic/knockout animals and models are prepared and used as described herein or using well known techniques, such as described in U.S. Pat. Nos. 5,800,998 and 5,891,628, each incorporated herein by reference.

Animals for testing therapeutic agents can be selected after mutagenesis of whole animals or after treatment of germline cells or zygotes. Such treatments include insertion of mutant dystrophin alleles, usually from a second animal species, as well as insertion of disrupted homologous genes. Alternatively, the endogenous dystrophin gene(s) of the animals may be disrupted by insertion or deletion mutation or other genetic alterations using conventional techniques (Capecchi, 1989; Valancius and Smithies, 1991; Hasty et al., 1991; Shinkai et al., 1992; Mombaerts et al., 1992; Philpott et al., 1992; Snouwaert et al., 1992; Donehower et al., 1992) to produce knockout or transplacement animals. A transplacement is similar to a knockout because the endogenous gene is replaced, but in the case of a transplacement the replacement is by another version of the same gene. After test substances have been administered to the animals, the DCM phenotype must be assessed. If the test substance prevents or suppresses the DCM phenotype, then the test substance is a candidate therapeutic agent for the treatment of sporadic DCM. These animal models provide an extremely important testing vehicle for potential therapeutic products.

In one embodiment of the invention, transgenic animals are produced which contain a functional transgene encoding a functional dystrophin polypeptide or variants thereof. Transgenic animals expressing dystrophin transgenes, recombinant cell lines derived from such animals and transgenic embryos may be useful in methods for screening for and identifying agents that induce or repress function of dystrophin. Transgenic animals of the present invention also can be used as models for studying indications such as sporadic DCM.

In one embodiment of the invention, a dystrophin transgene is introduced into a non-human host to produce a transgenic animal expressing a human, murine or other species dystrophin gene. The transgenic animal is produced by the integration of the transgene into the genome in a manner that permits the expression of the transgene. Methods for producing transgenic animals are generally described by Wagner and Hoppe (U.S. Pat. No. 4,873,191; which is incorporated herein by reference), Brinster et al. 1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

It may be desirable to replace the endogenous dystrophin by homologous recombination between the transgene or a mutant gene and the endogenous gene; or the endogenous gene may be eliminated by deletion as in the preparation of "knock-out" animals. Typically, a dystrophin gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish. Within a particularly preferred embodiment, transgenic mice are generated which overexpress dystrophin or express a mutant form of the polypeptide. Alternatively, the absence of a dystrophin in "knock-out" mice permits the study of the effects that loss of dystrophin protein has on a cell in vivo. Knock-out mice also provide a model for the development of dystrophin-related sporadic DCM.

Methods for producing knockout animals are generally described by Shastry (1995, 1998) and Osterrieder and Wolf (1998). The production of conditional knockout animals, in which the gene is active until knocked out at the desired time is generally described by Feil et al. (1996), Gagneten et al. (1997) and Lobe and Nagy (1998). Each of these references is incorporated herein by reference.

As noted above, transgenic animals and cell lines derived from such animals may find use in certain testing experiments. In this regard, transgenic animals and cell lines capable of expressing wild-type or mutant dystrophin may be exposed to test substances. These test substances can be screened for the ability to alter expression of wild-type dystrophin or alter the expression or function of mutant dystrophin.

Pharmaceutical Compositions and Routes of Administration

The dystrophin polypeptides, antibodies, peptides and nucleic acids of the present invention can be formulated in pharmaceutical compositions, which are prepared according to conventional pharmaceutical compounding techniques. See, for example, *Remington's Pharmaceutical Sciences,* 18th Ed. (1990, Mack Publishing Co., Easton, Pa.). The composition may contain the active agent or pharmaceutically acceptable salts of the active agent. These compositions may comprise, in addition to one of the active substances, a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration, e.g., intravenous, oral, intrathecal, epineural or parenteral.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

The active agent is preferably administered in a therapeutically effective amount. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in *Remington's Pharmaceutical Sciences.*

Alternatively, targeting therapies may be used to deliver the active agent more specifically to certain types of cell, by the use of targeting systems such as antibodies or cell specific ligands. Targeting may be desirable for a variety of reasons, e.g. if the agent is unacceptably toxic, or if it would otherwise require too high a dosage, or if it would not otherwise be able to enter the target cells.

Instead of administering these agents directly, they could be produced in the target cell, e.g. in a viral vector such as described above or in a cell based delivery system such as described in U.S. Pat. No. 5,550,050 and published PCT application Nos. WO 92/19195, WO 94/25503, WO 95/01203, WO 95/05452, WO 96/02286, WO 96/02646, WO 96/40871, WO 96/40959 and WO 97/12635, designed for implantation in a patient. The vector could be targeted to the specific cells to be treated, or it could contain regulatory elements which are more tissue specific to the target cells. The cell based delivery system is designed to be implanted in a patient's body at the desired target site and contains a coding sequence for the active agent. Alternatively, the agent could be administered in a precursor form for conversion to the active form by an activating agent produced in, or targeted to, the cells to be treated. See for example, EP 425,731 A and WO 90/07936.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982; Sambrook et al., 1989; Ausubel et al., 1992; Glover, 1985; Anand, 1992; Guthrie and Fink, 1991; Harlow and Lane, 1988; Jakoby and Pastan, 1979; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Hogan et al., Manipulating the Mouse Embryo, (Cold Spring Harbor Laboratory Press, Cold Spring Harbor, N.Y., 1986). A general discussion of techniques and materials for human gene mapping, including mapping of human chromosome 1, is provided, e.g., in White and Lalouel (1988).

EXAMPLES

The present invention is described by reference to the following Examples, which are offered by way of illustration and is not intended to limit the invention in any manner. Standard techniques well known in the art or the techniques specifically described below were utilized.

Example 1

Materials and Methods

Patients: Twenty-two children (ages 4-18 years) with clinical features of DCM were included in the study. All the children presented with congestive heart failure. Chest X-rays showed cardiomegaly and increased pulmonary vascular markings. Echocardiograms identified left ventricular dilation with left ventricular end-diastolic dimensions (LVEDD) greater than 3 standard deviations above the mean of normal (Z score >3) and reduced contractile function, with shortening fractions below 20% and ejection fractions below 40% in all patients. None of the children had a known etiology. None of these individuals had either first or second degree relatives with dilated cardiomyopathy.

PCR Amplification and DOVAM-S: DOVAM-S was performed as previously described (Mendell et al., 2001; Buzin et al., 2000; Liu et al., 1999). In brief, genomic DNA (Buzin et al., 2000) was amplified robotically with PCR on the ABI PRISM™ 877 integrated thermal cycler (Applied Biosystems, Inc., Foster City, Calif.) to generate ninety separate PCR segments labeled with $[\alpha^{33}P]dATP$ (Amersham, Boston, Mass.), which included all 79 coding sequences and splice junctions, as well as six alternative exon 1 (Dp4271, Dp427c, Dp427p, Dp260, Dp140, and Dp116) dystrophin isoforms, in 22 patients with sporadic DCM (Mendell et al., 2001; Buzin et al., 2000; Liu et al., 1999). Segments showing altered mobility were sequenced and mutations were confirmed by reamplification from the original genomic DNA and sequencing in the opposite direction.

Example 2

Association of Dystrophin and Sporadic DCM

We hypothesized that missense mutations and other less severe mutations might predispose to DCM but clinical manifestation may require some environmental effector or a modifying gene. These mutations would have reduced penetrance and generally appear as sporadic DCM. To test this hypothesis, we examined 22 patients with sporadic DCM.

Mutation screening has been developed for the dystrophin gene (Mendell et al., 2001) using DOVAM-S (Detection of Virtually All Mutations-SSCP), a form of SSCP in which there is sufficient redundancy to detect virtually all mutations (Buzin et al., 2000; Liu et al., 1999). DOVAM-S has successfully detected all 240 mutations and polymorphisms in three blinded analyses of the factor VIII, factor IX, and ATM genes (Buzin et al., 2000; Liu et al., 1999). Herein, 22 kb of genomic dystrophin DNA was scanned in 22 patients with sporadic DCM (484 kb total), including all 79 coding sequences and splice junctions, as well as six alternative exon 1 dystrophin isoforms. Three putative new mutations and six putative polymorphic structural variants were identified (Table 1) (FIG. 1).

The three mutations were scattered across the gene, including the intron 5 splice site and missense mutations in exon 47 and exon 67 (Table 1). Patient DCM-10, an African-American male who presented at age 12, had a mutation which disrupts the canonical GT dinucleotide at base one of IVS5. The predicted skipping of exon 5, a region containing an actin binding site (Winder et al., 1995), should result in dystrophin mRNA with an in frame deletion. A missense mutation, N2299T, occurred in a Latin-American male (DCM-33) who presented at the age of 15 with severe congestive heart failure and subsequently underwent successful cardiac transplantation. The amino acid at this position is conserved in dog and mouse dystrophin and in the related utrophin gene in human, mouse and rat. Patient DCM-51 had a missense mutation (F3228L) in a region with more available sequence. F3228 is identical in dog, mouse, chicken, Torpedo, dogfish, starfish, scallop, and Amphioxus. Screening of 141 control individuals failed to identify the IVS5+1, N2299T, or F3228L mutations.

Six polymorphic structural variants were identified in the 22 patients with sporadic DCM (Table 1). All of these were either reported as polymorphisms in the database or found as an incidental finding in DMD patients with truncating mutation in dystrophin patients (Mendell et al., 2001). One of the polymorphisms (IVS1L+1) is intriguing. The first nucleotide of intron 1 of the lymphocyte dystrophin transcript (Dp4271, L-dystrophin) is altered, predicting abnormal splicing. The allele frequency of this splicing mutation in DCM patients (9.1%) is significantly higher than that in 141 controls (0.7%) (p=0.02). The function of L-dystrophin is not clear. The relationship, if any, between this mutation and DCM remains to be determined.

date for familial DCM (dystrophin, tafazzin, actin, desmin, lamin A/C, δ-sarcoglycan, β-myosin heavy chain, troponin T) all have been associated with skeletal myopathies, again suggesting that cardiomyopathies and skeletal myopathies coexist. A relationship between mutations in the dystrophin gene and sporadic cardiomyopathy further supports the "final common pathway" hypothesis that suggests that the cytoskeleton/sarcolemma and its linkage to the sarcomere is the critical pathway involved in the pathogenesis of DCM (Bowles et al., 2001).

DCM is an uncommon disease. If mutations in the promoter region in exon 1 caused DCM with a penetrance approaching one, the clinical manifestation would appear as an X-linked disease. Other mutations that may increase the relative risk dramatically, but they would present predominantly as sporadic DCM if the penetrance is 25% or less. Future studies are needed to confirm that mutations in the dystrophin gene are a frequent cause of DCM and to analyze families with these dystrophin mutations to search for environmental or genetic modifiers that may help to generate the disease phenotype.

The initial impetus for this study came from previous work on DMD. The application to sporadic DCM arose by "Mendel leaping" from the pathophysiology of DMD to the complex disease DCM. Mendel leaping is an approach for selecting candidate genes for complex disease (Weinshenker and Sommer, 2001).

Recent data suggest that complex diseases can be a partial, arrested, or inapparent form of Mendelian disease. Compound heterozygotes with one recessive Mendelian disease-causing and one mild mutation can predispose to a complex disease that can manifest one or a few of the phenotypes of the Mendelian disease. The leap from Mendelian to complex disease preserves the organ system and general pathological process, but the histopathology can differ and the penetrance may be incomplete. If the penetrance for the complex disease is less than 50% the Mendelian nature of the phenotype will

TABLE 1

Variants in Sporadic DCM Patients

| No. | ID# | NT Change | NT No.[1] | AA Change | Codon | Region | DB/Con[2] | Comments |
|---|---|---|---|---|---|---|---|---|
| 1 | 174/DCM-10 | G > T | IVS5 + 1 | | | intron 5 | N/N | Disease specific |
| 2 | 158/DCM-33 | A > C | 7104 | Asn > Thr | 2299 | E47 | N/N | Disease specific |
| 3 | 189/DCM-51 | T > C | 9890 | Phe > Leu | 3228 | E67 | N/N | Disease specific |
| 4 | 154/DCM-25 | G > A | IVS1L[3] + 1 | | | 1L intron1 | N/Y | 1 in 141 controls |
|   | 185/DCM-37 | G > A | IVS1L + 1 | | | 1L intron1 | N/Y | " |
| 5 | 164/DCM-45 | C > T | 6671 | Arg > Trp | 2155 | E45 | Y/Y | 7 in 141 controls |
| 6 | 154/DCM-25 | A > C | 7304 | Lys > Gln[4] | 2366 | E48 | Y/Y | 28 in 141 controls |
|   | 158/DCM-33 | A > C | 7304 | Lys > Gln | 2366 | E48 | Y/Y | " |
|   | 178/DCM-17 | A > C | 7304 | Lys > Gln | 2366 | E48 | Y/Y | " |
|   | 179/DCM-23 | A > C | 7304 | Lys > Gln | 2366 | E48 | Y/Y | " |
|   | 182/DCM-31 | A > C | 7304 | Lys > Gln | 2366 | E48 | Y/Y | " |
| 7 | 143/DCM-5 | A > T | 8937 | Glu > Val | 2910 | E59 | Y/Y | 2 in 141 controls |
| 8 | 143/DCM-5 | A > G | 8942 | Asn > Asp | 2912 | E59 | Y/Y | 2 in 141 controls |
| 9 | 163/DCM-43 | A > G | 9018 | Gln > Arg | 2937 | E59 | Y/Y | 13 in 141 controls |

Notes:
[1]NT is with respect to Genbank Accession No. M18533.
[2]DB: denotes whether the mutation or polymorphism is reported in the dystrophin database (http://www.dmd.nl). Con: denotes whether the mutation or polymorphism was detected in 141 control samples.
[3]1L: intron 1 of lymphocyte dystrophin isoform (Dp4271).
[4]Gln in Genbank, but Lys in most of our samples. Gln form found in 28/141 controls.

As dystrophin mutations are associated with clinical or subclinical skeletal myopathy, it is possible that the muscle fatigue seen chronically in many patients with DCM could be due to primary skeletal muscle disease and not due primarily to chronic heart failure. Interestingly, the genes identified to not be apparent, especially if genetic heterogeneity and phenocopies exist. Three examples illustrate the paradigm.

Cystic fibrosis, the most common lethal Mendelian recessive disease in Western Europeans, arises from mutations in the CFTR gene. Some patients with cystic fibrosis develop a specific form of pancreatitis and boys often have congenital bilateral absence of the vas deferens (CBAVD). Subsequently it was discovered that a subset of healthy individuals who present with either idiopathic chronic pancreatitis or infertility were found to be compound heterozygotes for a cystic fibrosis causing CFTR mutation and a mild mutation (Cohn et al., 1998; Sharer et al., 1998; Claustres et al., 2000). Compound heterozygotes with idiopathic chronic pancreatitis have a different histopathology than is found in cystic fibrosis patients with pancreatitis (Cohn et al., 1998).

Ataxia telangiectasia is a multi-system recessive disorder due to mutations in the ATM gene. About ⅓ of A-T parents develop malignancy, mostly of the lymphoid type, including T-cell prolymphocytic leukemia (T-PLL). Subsequently, ATM somatic mutations were found to occur frequently in sporadic T-PLL (Vorechovsky et al., 1997) and B cell chronic lymphocytic leukemia (Stankovic et al., 1999; Bullrich et al., 1999; Schaffner et al., 1999) in adults.

These examples hint that "Mendel leaping" may be a general strategy for chipping away at complex disease. Carriers for the Mendelian disease may be predisposed to a forme fruste but the relative risk will be lower than for compound heterozygotes. Depending on the frequencies in the population of Mendelian disease-causing alleles relative to mild alleles, the carriers may provide the higher attributable risk even though relative risk may be much higher for compound heterozygotes.

The promising of findings generated by the laboratories first attempt at Mendel leaping is intriguing. More work is needed to assess the general utility of this approach for selecting candidate genes for complex disease.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

What is claimed is:

1. An isolated nucleic acid which is a mutated version of a wild-type human dystrophin gene, wherein the mutated version is a DNA molecule comprising nucleotides 209 to 11263 of SEQ ID NO:1, wherein A at nucleotide position 7104 is substituted with C, or the full complement thereof.

2. A nucleic acid probe hybridizable to a human mutated dystrophin and not hybridizable to wild-type human DNA, wherein said wild-type human DNA is a DNA molecule comprising nucleotides 209 to 11263 of SEQ ID NO:1 or the full complement thereof, said probe comprises at least 12 consecutive nucleotides of said human mutated dystrophin and said human mutated dystrophin consists of the nucleic acid of claim 1, and wherein said probe encompasses a C at position 7104 of SEQ ID NO:1 or its complement.

* * * * *

UNITED STATES PATENT AND TRADEMARK OFFICE
CERTIFICATE OF CORRECTION

| | | |
|---|---|---|
| PATENT NO. | : 7,449,561 B1 | Page 1 of 9 |
| APPLICATION NO. | : 10/371222 | |
| DATED | : November 11, 2008 | |
| INVENTOR(S) | : Steve S. Sommer et al. | |

It is certified that error appears in the above-identified patent and that said Letters Patent is hereby corrected as shown below:

Title Page item 56 - line 8 in "Other Publications"

Page 1, col. 2, Mendell reference, second line, "Muations" should read "Mutations"

In the Specification

Col. 2, line 44, "susceptability" should read "susceptibility"

Col. 2, line 48, "susceptability" should read "susceptibility"

Col. 10, line 23, delete parenthesis before "substantial"

Col. 14, line 4, delete "in" before "herein"

Col. 18, line 41, delete comma after "calcium"

Col. 21, line 62, insert parenthesis before "which"

Bibliography

Col. 28, after line 20, before sequence listing, please insert the entire "Bibliography," pages 146-151 of original application, as follows:

BIBLIOGRAPHY

Altschul, S.F. *et al.* (1990). Basic local alignment search tool. *J. Mol. Biol.* 215:403-410.

Altschul, S.F. *et al.* (1997). Gapped BLAST and PSI-BLAST: a new generation of protein database search programs. *Nucl. Acids Res.* 25:3389-3402.

Anand, R. (1992). *Techniques for the Analysis of Complex Genomes*, (Academic Press).

Arbustini, E. et al. (2000). Prevalence and characteristics of dystrophin defects in adult male patients with dilated cardiomyopathy. *J Am Coll Cardiol* 35:1760-1768.

Ausubel, F.M., *et al.* (1992). *Current Protocols in Molecular Biology*, (J. Wiley and Sons, NY).

UNITED STATES PATENT AND TRADEMARK OFFICE
CERTIFICATE OF CORRECTION

PATENT NO.        : 7,449,561 B1
APPLICATION NO.   : 10/371222
DATED             : November 11, 2008
INVENTOR(S)       : Steve S. Sommer et al.

It is certified that error appears in the above-identified patent and that said Letters Patent is hereby corrected as shown below:

BIBLIOGRAPHY (cont'd)

Bartel, P.L., *et al.* (1993). "Using the 2-hybrid system to detect protein-protein interactions." *In: Cellular Interactions in Development: A Practical Approach,* Oxford University Press, pp. 153-179.

Beggs, A.H. et al. (1991). Exploring the molecular basis for variability among patients with Becker muscular dystrophy: dystrophin gene and protein studies. *Am J Hum Genet* 49:54-67.

Borman S (1996). *Chemical & Engineering News*, December 9 issue, pp. 42-43.

Botstein, *et al.* (1980). *Am. J. Hum. Genet.* 32:314-331.

Bowles, N.E. et al. (2000). The "final common pathway" hypothesis and inherited cardiovascular disease. The role of cytoskeletal proteins in dilated cardiomyopathy. *Herz* 25:168-175.

Bullrich, F. et al. (1999). ATM mutations in B-Cell chronic lymphocytic leukemia. *Cancer Res.* 59:24-27.

Buzin, C.H. et al. (2000). Scanning by DOVAM-S detects all unique sequence changes in blinded analyses: evidence that the scanning conditions are generic. *BioTechniques* 28:746-753.

Capecchi, M.R. (1989). *Science* 244:1288.

Cariello (1988). *Human Genetics* 42:726.

Chee M, et al. (1996). *Science* 274:610-614.

Chevray, P.M. and Nathans, D.N. (1992). *Proc. Natl. Acad. Sci. USA* 89:5789-5793.

Claustres, M. et al. (2000). Spectrum of CFTR mutations in cystic fibrosis and in congenital absence of the vas deferens in France. *Hum Mutat* 16:143-156.

Cohn, J.A. et al. (1998). Relation between mutations of the cystic fibrosis gene and idiopathic pancreatitis [see comments]. *N Engl J Med* 339:653-658.

UNITED STATES PATENT AND TRADEMARK OFFICE
CERTIFICATE OF CORRECTION

PATENT NO. : 7,449,561 B1
APPLICATION NO. : 10/371222
DATED : November 11, 2008
INVENTOR(S) : Steve S. Sommer et al.

It is certified that error appears in the above-identified patent and that said Letters Patent is hereby corrected as shown below:

BIBLIOGRAPHY (cont'd)

Conner, B.J., et al. (1983). *Proc. Natl. Acad. Sci. USA* 80:278-282.

Cotton, et al. (1988). *Proc. Natl. Acad. Sci. USA* 85:4397-4401.

DeRisi J, et al. (1996). *Nat. Genet.* 14:457-460.

Donehower, L.A., et al. (1992). *Nature* 356:215.

Erickson, J. et al., (1990). *Science* 249:527-533.

Feil et al., (1996). *Proc. Natl. Acad. Sci. USA* 93:10887-10890.

Fields, S. and Song, O-K. (1989). *Nature* 340:245-246.

Ferlini, A. et al. (1998). A novel Alu-like element rearranged in the dystrophin gene causes a splicing mutation in a family with X-linked dilated cardiomyopathy. *Am J Hum Genet* 63:436-446.

Finkelstein, J., et al. (1990). *Genomics* 7:167-172.

Fodor, S.P.A. (1997). DNA Sequencing. Massively Parallel Genomics. *Science* 277:393-395.

Gagneten et al. (1997). *Nucl. Acids Res.* 25:3326-3331.

Glover, D. (1985). *DNA Cloning*, I and II (Oxford Press).

Gold, R. et al. (1992). Becker muscular dystrophy: detection of unusual disease courses by combined approach to dystrophin analysis. *Muscle Nerve* 15:214-218.

Grompe, M., (1993). *Nature Genetics* 5:111-117.

Grompe, M., et al., (1989). *Proc. Natl. Acad. Sci. USA* 86:5855-5892.

Guthrie, G. and Fink, G.R. (1991). *Guide to Yeast Genetics and Molecular Biology* (Academic Press).

UNITED STATES PATENT AND TRADEMARK OFFICE
CERTIFICATE OF CORRECTION

PATENT NO. : 7,449,561 B1
APPLICATION NO. : 10/371222
DATED : November 11, 2008
INVENTOR(S) : Steve S. Sommer et al.

It is certified that error appears in the above-identified patent and that said Letters Patent is hereby corrected as shown below:

BIBLIOGRAPHY (cont'd)

Hacia JG, et al. (1996). *Nature Genetics* 14:441-447.

Harlow and Lane (1988). *Antibodies: A Laboratory Manual* (Cold Spring Harbor Laboratory, Cold Spring Harbor, NY.

Hasty, P., K., *et al.* (1991). *Nature* 350:243.

Hodgson, J. (1991). *Bio/Technology* 9:19-21. Hogan et al. (eds) (1994). *Manipulating the Mouse Embryo: A Laboratory Manual*, 2nd Edition, Cold Spring Harbor Laboratory Press, Cold Spring Harbor, NY.

Hunsaker, R.H. et al., (1982). Cardiac function in Duchenne's muscular dystrophy. Results of 10-year follow-up study and noninvasive tests. *Am J Med* 73:235-238.

Jablonski, E., *et al.* (1986). *Nuc. Acids Res.* 14:6115-6128.

Jakoby, W.B. and Pastan, I.H. (eds.) (1979). *Cell Culture. Methods in Enzymology*, Vol. 58 (Academic Press, Inc., Harcourt Brace Jovanovich (NY).

Jeffreys, *et al.* (1985). *Nature* 314:67-73.

Kinszler, K.W., *et al.* (1991). *Science* 251:1366-1370.

Kinzler, K.W. and Vogelstein, B. 1997. *Nature* 386: 761-763.

Landegren, *et al.* (1988). *Science* 242:229.

Lee, J.E., *et al.* (1995). *Science* 268:836-844.

Lipshutz RJ, et al. (1995). *BioTechniques* 19:442-447.

Litt, *et al.* (1989). *Am. J. Hum. Genet.* 44:397-401.

Liu, Q. et al. (1999). Detection of virtually all mutations-SSCP (DOVAM-S): A rapid method for mutation scanning with virtually 100% sensitivity. *BioTechniques* 26:932-942.

UNITED STATES PATENT AND TRADEMARK OFFICE
CERTIFICATE OF CORRECTION

PATENT NO. : 7,449,561 B1
APPLICATION NO. : 10/371222
DATED : November 11, 2008
INVENTOR(S) : Steve S. Sommer et al.

It is certified that error appears in the above-identified patent and that said Letters Patent is hereby corrected as shown below:

BIBLIOGRAPHY (cont'd)

Lobe and Nagy (1998). *Bioessays* 20:200-208.

Lockhart DJ, et al. (1996). *Nature Biotechnology* 14:1675-1680.

Maniatis. T., *et al.* (1982). *Molecular Cloning: A Laboratory Manual* (Cold Spring Harbor Laboratory, Cold Spring Harbor, NY).

Matthews and Kricka (1988). *Anal. Biochem.* 169:1.

Mendell, J.R. et al. (2001). Diagnosis of Duchenne Dystrophy by Enhanced Detection of Small Mutations. *Neurology* 57:645-650.

Milasin, J. et al. (1996). A point mutation in the 5' splice site of the dystrophin gene first intron responsible for X-linked dilated cardiomyopathy. *Hum Mol Genet* 5:73-79.

Mittlin (1989). *Clinical Chem.* 35:1819.

Modrich, P. (1991). *Ann. Rev. Genet.* 25:229-253.

Mombaerts, P., *et al.* (1992). *Cell* 68:869.

Muntoni, F. et al. (1993). Brief report: deletion of the dystrophin muscle-promoter region associated with X-linked dilated cardiomyopathy. *N Engl J Med* 329:921-925.

Muntoni, F. et al. (1995a). A mutation in the dystrophin gene selectively affecting dystrophin expression in the heart. *J Clin Invest* 96:693-699.

Muntoni, F. et al. (1995b). Transcription of the dystrophin gene in normal tissues and in skeletal muscle of a family with X-linked dilated cardiomyopathy. *Am J Hum Genet* 56:151-157.

Muntoni, F. et al. (1997). Dystrophin gene abnormalities in two patients with idiopathic dilated cardiomyopathy. *Heart* 78:608-612.

Nakamura, *et al.* (1987). *Science* 235:1616-1622.

UNITED STATES PATENT AND TRADEMARK OFFICE
CERTIFICATE OF CORRECTION

PATENT NO. : 7,449,561 B1
APPLICATION NO. : 10/371222
DATED : November 11, 2008
INVENTOR(S) : Steve S. Sommer et al.

It is certified that error appears in the above-identified patent and that said Letters Patent is hereby corrected as shown below:

BIBLIOGRAPHY (cont'd)

Newton, C.R., et al. (1989). *Nucl. Acids Res.* 17:2503-2516.

Nguyen, Q., et al. (1992). *BioTechniques* 13:116-123.

Novack, et al. (1986). *Proc. Natl. Acad. Sci. USA* 83:586.

Orita, et al. (1989). *Proc. Natl. Acad. Sci. USA* 86:2776-2770.

Ortiz-Lopez, R. et al. (1997). Evidence for a dystrophin missense mutation as a cause of X-linked dilated cardiomyopathy [see comments]. *Circulation* 95:2434-2440.

Osterrieder and Wolf (1998). *Rev. Sci. Tech.* 17:351-364.

Perloff, J.K. et al. (1996). The cardiomyopathy of progressive muscular dystrophy. *Circulation* 33:625-648.

Philpott, K.L., et al. (1992). *Science* 256:1448.

Rano and Kidd (1989). *Nucl. Acids Res.* 17:8392.

Rigby, P.W.J., et al. (1977). *J. Mol. Biol.* 113:237-251.

Sambrook, J., et al. (1989). *Molecular Cloning: A Laboratory Manual*, 2nd Ed. (Cold Spring Harbor Laboratory, Cold Spring Harbor, NY).

Schaffner, C. et al. (1999). Stilgenbauer S, Rappold GA, et al: Somatic ATM mutations indicate a pathogenic role of ATM in B-cell chronic lymphocytic leukemia. *Blood* 94:748-753.

Sharer, N. et al. (1998). Mutations of the cystic fibrosis gene in patients with chronic pancreatitis [see comments]. *N Engl J Med* 339:645-652.

Shastry et al. (1995). *Experientia* 51:1028-1039.

Shastry et al. (1998). *Mol. Cell. Biochem.* 181:163-179.

Sheffield, V.C., et al. (1989). *Proc. Natl. Acad. Sci. USA* 86:232-236.

UNITED STATES PATENT AND TRADEMARK OFFICE
CERTIFICATE OF CORRECTION

PATENT NO. : 7,449,561 B1
APPLICATION NO. : 10/371222
DATED : November 11, 2008
INVENTOR(S) : Steve S. Sommer et al.

It is certified that error appears in the above-identified patent and that said Letters Patent is hereby corrected as shown below:

BIBLIOGRAPHY (cont'd)

Sheffield, V.C., et al. (1991). *Am. J. Hum. Genet.* 49:699-706.

Shenk, et al. (1975). *Proc. Natl. Acad. Sci. USA* 72:989.

Shinkai, Y., et al. (1992). *Cell* 68:855.

Shoemaker DD, et al. (1996). *Nature Genetics* 14:450-456.

Skolnick, M.H. and Wallace, B.R. (1988). *Genomics* 2:273-279.

Snouwaert, J.N., et al. (1992). *Science* 257:1083.

Stankovic, T. et al. (1999). Inactivation of ataxia telangiectasia mutated gene in B-cell chronic lymphocytic leukaemia. *Early Reports* 353:26-29.

Tavtigian, S., et al. (1996). *Nature Genetics* 12:333-337.

Vorechovsky, I. et al. (1997). Clustering of missense mutations in the ataxia-telangiectasia gene in a sporadic T-cell leukaemia. *Nature Genet.* 17:96-99.

Wartell, R.M., et al. (1990). *Nucl. Acids Res.* 18:2699-2705.

Weber and May (1989). *Am. J. Hum. Genet.* 44:388-396.

Weinshenker, B.G. and Sommer, S.S. (2001). VAPSE-based Analysis: a two-phased candidate gene approach for elucidating genetic predisposition to complex disorders. *Mutation Research* 458:7-17.

Wells, J.A. (1991). *Methods in Enzymol.* 202:390-411.

Wetmur, J.G. and Davidson, N. (1968). "Kinetics of renaturation of DNA." *J. Mol. Biol.* 31:349-370.

White, M.B., et al., (1992). *Genomics* 12:301-306.

UNITED STATES PATENT AND TRADEMARK OFFICE
CERTIFICATE OF CORRECTION

| | |
|---|---|
| PATENT NO. | : 7,449,561 B1 |
| APPLICATION NO. | : 10/371222 |
| DATED | : November 11, 2008 |
| INVENTOR(S) | : Steve S. Sommer et al. |

It is certified that error appears in the above-identified patent and that said Letters Patent is hereby corrected as shown below:

BIBLIOGRAPHY (cont'd)

White and Lalouel (1988). *Ann. Rev. Genet.* 22:259-279.

Winder, S.J. et al. (1995). Dystrophin and utrophin: the missing links! *FEBS Lett* 369:27-33.

Yoshida, K. et al. (1998). Insertional mutation by transposable element, L1, in the *DMD* gene results in X-linked dilated cardiomyopathy. *Hum.Molec.Genet.*7:1129-1132.

European Patent Application Publication No. 225,807

European Patent Application Publication No. 425,731A.

European Patent Application Publication No. 0332435

Geysen, H., PCT published application No. WO 84/03564, published 13 September 1984

UNITED STATES PATENT AND TRADEMARK OFFICE
CERTIFICATE OF CORRECTION

PATENT NO. : 7,449,561 B1
APPLICATION NO. : 10/371222
DATED : November 11, 2008
INVENTOR(S) : Steve S. Sommer et al.

It is certified that error appears in the above-identified patent and that said Letters Patent is hereby corrected as shown below:

BIBLIOGRAPHY (cont'd)

PCT published application No. WO 90/07936.

PCT published application No. WO 92/19195.

PCT published application No. WO 93/07282.

PCT published application No. WO 94/25503.

PCT published application No. WO 95/01203.

PCT published application No. WO 95/05452.

PCT published application No. WO 96/02286.

PCT published application No. WO 96/02646.

PCT published application No. WO 96/11698.

PCT published application No. WO 96/40871.

PCT published application No. WO 96/40959.

PCT published application No. WO 97/12635.

Signed and Sealed this

Third Day of March, 2009

JOHN DOLL
*Acting Director of the United States Patent and Trademark Office*